US011859080B2

United States Patent
Tenne et al.

(10) Patent No.: US 11,859,080 B2
(45) Date of Patent: Jan. 2, 2024

(54) HYDROXYAPATITE BASED COMPOSITES AND FILMS THEREOF

(71) Applicants: YEDA RESEARCH AND DEVELOPMENT CO. LTD., Rehovot (IL); HOLON ACADEMIC INSTITUTE OF TECHNOLOGY, Holon (IL)

(72) Inventors: Reshef Tenne, Rehovot (IL); Hila Shalom, Rehovot (IL); Lev Rapoport, Lod (IL); Ofek Golan, Rehovot (IL)

(73) Assignees: YEDA RESEARCH AND DEVELOPMENT CO. LTD., Rehovot (IL); HOLON ACADEMIC INSTITUTE OF TECHNOLOGY, Holon (IL)

( * ) Notice: Subject to any disclaimer, the term of this patent is extended or adjusted under 35 U.S.C. 154(b) by 131 days.

(21) Appl. No.: 17/515,890

(22) Filed: Nov. 1, 2021

(65) Prior Publication Data
US 2022/0049087 A1    Feb. 17, 2022

Related U.S. Application Data

(63) Continuation-in-part of application No. 16/970,958, filed as application No. PCT/IL2019/050203 on Feb. 21, 2019.

(30) Foreign Application Priority Data

Feb. 22, 2018  (IL) .......................................... 257697

(51) Int. Cl.
*C08L 67/04*     (2006.01)
*C08K 3/04*      (2006.01)
(Continued)

(52) U.S. Cl.
CPC ............... *C08L 67/04* (2013.01); *A61L 27/04* (2013.01); *A61L 27/34* (2013.01); *C08K 3/045* (2017.05);
(Continued)

(58) Field of Classification Search
CPC ........... C08L 67/04; C08K 3/045; C08K 3/30; C08K 3/32; A61L 27/04; A61L 27/34
See application file for complete search history.

(56) References Cited

U.S. PATENT DOCUMENTS 8,329,138 B2   12/2012   Tenne et al.
8,435,343 B2   5/2013    Yahav et al.
(Continued)

FOREIGN PATENT DOCUMENTS

CN   101949046   1/2011
CN   105274603   1/2016
(Continued)

OTHER PUBLICATIONS

Naffakh et al. Development of novel melt-processable biopolymer nanocomposites based on poly(L-lactic acid) and WS2 inorganic nanotubes. CrystEnglComm, 2014, 16, 5062 (Year: 2014).*
(Continued)

*Primary Examiner* — John E Uselding
(74) *Attorney, Agent, or Firm* — Mark S. Cohen; PEARL COHEN ZEDEK LATZER BARATZ LLP

(57) ABSTRACT

This invention is directed to composites and films comprising hydroxyapatite, biodegradable polymer, a biocompatible surfactant with inorganic fullerene-like (IF) nanoparticles or inorganic nanotubes (INT); methods of preparation and uses thereof.

20 Claims, 23 Drawing Sheets

(51) Int. Cl.
*C08K 3/32* (2006.01)
*A61L 27/34* (2006.01)
*A61L 27/04* (2006.01)
*C08K 3/30* (2006.01)

(52) U.S. Cl.
CPC .................. *C08K 3/30* (2013.01); *C08K 3/32* (2013.01); *C08K 2003/3009* (2013.01); *C08K 2003/325* (2013.01); *C08K 2201/005* (2013.01); *C08K 2201/011* (2013.01); *C08K 2201/018* (2013.01); *C08L 2201/06* (2013.01); *C08L 2203/16* (2013.01)

(56) References Cited

U.S. PATENT DOCUMENTS

| | | |
|---|---|---|
| 8,518,364 B2 | 8/2013 | Tenne et al. |
| 9,155,595 B2 | 10/2015 | Tenne et al. |
| 9,242,231 B2 | 1/2016 | Tenne et al. |
| 9,496,067 B2 | 11/2016 | Tenne et al. |
| 9,527,735 B2 | 12/2016 | Tenne et al. |
| 9,877,806 B2 | 1/2018 | Tenne et al. |
| 2007/0259101 A1 | 11/2007 | Kleiner et al. |
| 2012/0021014 A1 | 1/2012 | Chantalat et al. |
| 2014/0138319 A1 | 5/2014 | Fu-Giles |
| 2014/0287264 A1 | 9/2014 | Tenne et al. |
| 2015/0073560 A1 | 3/2015 | Shavit |
| 2016/0133925 A1 | 5/2016 | Tenne et al. |
| 2016/0331874 A1 | 11/2016 | Tenne et al. |
| 2018/0171435 A1 | 6/2018 | Tenne et al. |

FOREIGN PATENT DOCUMENTS

| | | |
|---|---|---|
| JP | 2015177096 | 10/2015 |
| KR | 2013-0053954 | 5/2013 |
| WO | WO 2006/123336 | 11/2006 |
| WO | WO 2009/034572 | 3/2009 |
| WO | WO 2011/111044 | 9/2011 |
| WO | WO 2011/161676 | 12/2011 |
| WO | WO 2013/057732 | 4/2013 |
| WO | WO 2014/033718 | 3/2014 |
| WO | WO 2014/203251 | 12/2014 |
| WO | WO 2015/102006 | 7/2015 |
| WO | WO 2015/170331 | 11/2015 |
| WO | WO 2016/193974 | 12/2016 |
| WO | WO 2017/163250 | 9/2017 |

OTHER PUBLICATIONS

Albano, C., et al. (2013). PLLA-HA vs. PLGA-HA characterization and comparative analysis. Polymer composites, 34(9), 1433-1442.
Alberdi et al.(2011)—Tribological behavior of nanocomposite coatings based on fullerene-like structures—Vacuum.Jun. 5;85(12):1087-92.
Andre et al.(2012)—Performance and tribofilm formation of a low-friction coating incorporating inorganic fullerene like nanoparticles—Surface and Coatings Technology. Jan. 15;206(8-9):2325-9.
Aninwene et al.(2008)—Enhanced osteoblast adhesion to drug-coated anodized nanotubular titanium surfaces—International journal of nanomedicine. Jun.;3(2):257.
Appel et al. (2016)—Low cytotoxicity and genotoxicity of two-dimensional MoS2 and WS2—Acs Biomaterials Science & Engineering. Mar. 3;2(3):361-7.
Assefpour-Dezfuly et al.(1984)—Oxide morphology and adhesive bonding on titanium surfaces—Journal of materials science. Nov. 1;19(11):3626-39.
Barber, A. H., et al. (2004). Interfacial fracture energy measurements for multi-walled carbon nanotubes pulled from a polymer matrix. Composites Science and Technology, 64(15), 2283-2289.
Basnyat et al.(2007)—Mechanical and tribological properties of CrAlN-Ag self-lubricating films—Surface and Coatings Technology. Dec. 15;202(4-7):1011-6.

Chen et al.(1998)—Calcium phosphate coating on titanium substrate by a modified electrocrystallization process—Journal of Materials Science: Materials in Medicine. May 1;9(5):297-300.
Chua, P. S., & Piggott, M. R. (1985). The glass fibre-polymer interface: I-theoretical consideration for single fibre pull-out tests. Composites Science and Technology, 22(1), 33-42.
Dos Santos, B. B., et al. (Dec. 2020). Characterization of Properties of Poly (vinylidene Fluoride) Using Instrumented Microindentation Test. In Macromolecular Symposia (vol. 394, No. 1, p. 2000136).
Dutrow, BL.(2016)—X-ray Powder Diffraction. Aug. 15, available at: https://serc.carleton.edu/research_education/geochemsheets/techniques/XRD.html
Farah, S., et al. (2016). Physical and mechanical properties of PLA, and their functions in widespread applications—A comprehensive review. Advanced drug delivery reviews, 107, 367-392.
Fojtů, M., et al. (2017). Environmental impact and potential health risks of 2D nanomaterials. Environmental Science: Nano, 4(8), 1617-1633.
Fusaro RL.(1990)—Self-lubricating polymer composites and polymer transfer film lubrication for space applications—Tribology International. Apr. 1;23(2):105-22.
Ghosh, S., et al . (2021). Reinforcement of poly (methyl methacrylate) by WS2 nanotubes towards antiballistic applications. Composites Science and Technology, 207, 108736.
Goldman et al.(2014)—Biocompatibility of tungsten disulfide inorganic nanotubes and fullerene-like nanoparticles with salivary gland cells—Tissue Engineering Part A. Dec. 18;21(5-6):1013-23.
Gong et al.(2001)—Titanium oxide nanotube arrays prepared by anodic oxidation—Journal of Materials Research. Dec.;16(12):3331-4.
International Search Report for PCT/IL2019/050203 dated May 6, 2019.
Jarząbek, D. M. (2018). The impact of weak interfacial bonding strength on mechanical properties of metal matrix—Ceramic reinforced composites. Composite Structures, 201, 352-362.
Johnsen, B. B., et al. (2007). Toughening mechanisms of nanoparticle-modified epoxy polymers. Polymer, 48(2), 530-541.
Kaplan-Ashiri, I., et al. (2006). On the mechanical behavior of WS2 nanotubes under axial tension and compression. Proceedings of the National Academy of Sciences, 103(3), 523-528.
Kazemzadeh-Narbat et al.(2010)—Antimicrobial peptides on calcium phosphate-coated titanium for the prevention of implant-associated infections—Biomaterials. Dec. 1;31(36):9519-26.
Ke, S., et al . (2018). Molybdenum disulfide nanoparticles resist oxidative stress-mediated impairment of autophagic flux and mitigate endothelial cell senescence and angiogenic dysfunctions. ACS Biomaterials Science & Engineering, 4(2), 663-674.
Kim, H. W., & Kim, H. E. (2006). Nanofiber generation of hydroxyapatite and fluor-hydroxyapatite bioceramics. Journal of Biomedical Materials Research Part B: Applied Biomaterials: An Official Journal of The Society for Biomaterials, The Japanese Society for Biomaterials, and The Australian Society for Biomaterials and the Korean Society for Biomaterials, 77(2), 323-328.
Kong, Y. M., et al. (2002). Hydroxyapatite-based composite for dental implants: An in vivo removal torque experiment. Journal of Biomedical Materials Research: An Official Journal of The Society for Biomaterials, The Japanese Society for Biomaterials, and The Australian Society for Biomaterials and the Korean Society for Biomaterials, 63(6), 714-721.
Lahiri et al.(2010)—Carbon nanotube toughened hydroxyapatite by spark plasma sintering: microstructural evolution and multiscale tribological properties—Carbon. Sep. 1;48(11):3103-20.
Lahiri et al.(2011)—Boron nitride nanotube reinforced hydroxyapatite composite: mechanical and tribological performance and in-vitro biocompatibility to osteoblasts—Journal of the mechanical behavior of biomedical materials.Jan. 1;4(1):44-56.
Legeros et al.(2003)—Biphasic calcium phosphate bioceramics: preparation, properties and applications—Journal of materials science: Materials in Medicine. Mar. 1;14(3):201-9.
Li et al.(2008)—Tribological properties of nickel-based self-lubricating composite at elevated temperature and counterface material selection—Wear. Jul. 31;265(3-4):533-9.

(56) References Cited

OTHER PUBLICATIONS

Lian et al.(2014)—Friction and wear behavior of WS 2/Zr self-lubricating soft coatings in dry sliding against 40Cr-hardened steel balls—Tribology Letters. Jan. 1;53(1):237-46.
Macak et al.(2005)—High-aspect-ratio TiO2 nanotubes by anodization of titanium—Angewandte Chemie International Edition. Mar. 29;44(14):2100-2.
Manzeli et al.(2017)—2D transition metal dichalcogenides—Nature Reviews Materials. Aug.:2(8):17033.
Moghadam et al.(2015)—Mechanical and tribological properties of self-lubricating metal matrix nanocomposites reinforced by carbon nanotubes (CNTs) and graphene—a review—Composites Part B: Engineering. Aug. 1;77:402-20.
Molitor et al.(2001)—Surface treatment of titanium for adhesive bonding to polymer composites: a review—International Journal of Adhesion and Adhesives.Jan. 1;21(2):129-36.
Naffakh, M., & Díez-Pascual, A. M. (2015). WS 2 inorganic nanotubes reinforced poly (I-lactic acid)/hydroxyapatite hybrid composite biomaterials. RSC advances, 5(80), 65514-65525.
Naffakh, M., & Marco, C. (2015). Isothermal crystallization kinetics and melting behavior of poly (I-lactic acid)/WS 2 inorganic nanotube nanocomposites. Journal of materials science, 50(18), 6066-6074.
Naffakh, M., et al. (2014). Novel poly (3-hydroxybutyrate) nanocomposites containing WS2 inorganic nanotubes with improved thermal, mechanical and tribological properties. *Materials Chemistry and Physics*, 147(1-2), 273-284.
Pardo et al.(2014)—Low cytotoxicity of inorganic nanotubes and fullerene-like nanostructures in human bronchial epithelial cells: relation to inflammatory gene induction and antioxidant response—Environmental science & technology. Feb. 26;48(6):3457-66.
Pardo, M., et al. (2014). Low cytotoxicity of inorganic nanotubes and fullerene-like nanostructures in human bronchial epithelial cells: relation to inflammatory gene induction and antioxidant response. Environmental science & technology, 48(6), 3457-3466.
Petit R.(1999)—The use of hydroxyapatite in orthopaedic surgery: a ten-year review—European Journal of Orthopaedic Surgery & Traumatology.Jun. 1;9(2):71-4.
Polcar et al.(2011)—Properties of nanocomposite film combining hard TIN matrix with embedded fullerene-like WS2 nanoclusters—Thin Solid Films.Mar. 1;519(10):3191-5.
Rapoport et al.(1997)—Hollow nanoparticles of WS 2 as potential solid-state lubricants—Nature. Jun.;387(6635):791.
Rashkow, J. T., et al. (2015). Interactions of 1D-and 2D-layered inorganic nanoparticles with fibroblasts and human mesenchymal stem cells. Nanomedicine, 10(11), 1693-1706.
Rey et al.(2007)—Nanocrystalline apatites in biological systems: characterisation, structure and properties—Materialwissenschaft und Werkstofftechnik.Dec. 1;38(12):996-1002.
Rocher, L., et al. (2021). Interaction of Poly L-Lactide and Tungsten Disulfide Nanotubes Studied by in Situ X-ray Scattering during Expansion of PLLA/WS2NT Nanocomposite Tubes. Polymers, 13(11), 1764.
Rodricks, C. W., et al. (2021). Polymer beads as interfacial obstacles in fibre composites. Composites Science and Technology, 210, 108793.
Rodriguez-Lugo et al.(2005)—Synthesis And Structural Characterization Of Hydroxyapatite Obtained from CaO and CaHP04 by a Hydrothermal Method—Materials Research Innovations. Mar. 1;9(1):20-2.
Rosentsveig et al.(2009)—Fullerene-like MoS 2 nanoparticles and their tribological behavior—Tribology Letters.Nov. 1;36(2):175-82.
Rosentsveig et al.(2018)—Doping of Fullerene-Like MoS2 Nanoparticles with Minute Amounts of Niobium-Particle & Particle Systems Characterization.Mar.;35(3):1700165.
Roy et al.(2011)—TiO2 nanotubes: synthesis and applications—Angewandte Chemie International Edition. Mar. 21;50(13):2904-39.
Sedova, A. et al.(2015)—Re-doped fullerene-like MoS2 nanoparticles in relationship with soft lubrication—Nanomaterials and Energy, 4(1), 30-38.

Sedova, A., et al. (2017). Dielectric and electrical properties of WS2 nanotubes/epoxy composites and their use for stress monitoring of structures. Journal of Nanomaterials, 2017.
Shalom H.(2016)—Advanced coatings based on nanomaterials for medical and other industrial applications—Azrieli Coll.Eng. 1-33.
Shalom, H., et al. (2019). Nanocomposite of poly (L-lactic acid) with inorganic nanotubes of WS2. Lubricants, 7(3), 28.
Shalom, H.et al.(2018)—Electrophoretic Deposition of Hydroxyapatite Film Containing Re-Doped Mos2 Nanoparticles—International journal of molecular sciences, 19(3), 657.
Shikinami, Y., & Okuno, M. (1999). Bioresorbable devices made of forged composites of hydroxyapatite (HA) particles and poly-L-lactide (PLLA): Part I. Basic characteristics. Biomaterials, 20(9), 859-877.
Singh, I.et al.(2006)—Bioactive ceramic coatings containing carbon nanotubes on metallic substrates by electrophoretic deposition—Journal of materials science, 41(24), 8144-8151.
Skeldon et al.(1997)—Formation and characterization of self-lubricating Mos2 precursor films on anodized aluminium—Wear. May 1;206(1-2):187-96.
Sridhar, T. M. et al.(2002)—Electrophoretic deposition of hydroxyapatite coatings and corrosion aspects of metallic implants—Corrosion reviews, 20(4-5), 255-294.
Stares, S. L., et al. (2013). PLLA/HA composite laminates. Advanced Engineering Materials, 15(11), 1122-1124.
Starkweather Jr, H. W., et al. (1956). Effect of crystallinity on the properties of nylons. Journal of Polymer Science, 21(98), 189-204.
Stuart, B. H., & Briscoe, B. J. (1996). Scratch hardness studies of poly (ether ether ketone). Polymer, 37(17), 3819-3824.
Šupová, M. (2009). Problem of hydroxyapatite dispersion in polymer matrices: a review. Journal of Materials Science: Materials in Medicine, 20(6), 1201-1213.
Takayama, T., & Todo, M. (2009). Improvement of mechanical properties of hydroxyapatite particle-filled poly (I-lactide) biocomposites using lysine tri-isocyanate. Journal of materials science, 44(18), 5017-5020.
Tariq, U., et al. (May 2018). Calcium to phosphate ratio measurements in calcium phosphates using LIBS. In Journal of Physics: Conference Series (vol. 1027, No. 1, p. 012015). IOP Publishing.
Tenne R. (2006)—Inorganic nanotubes and fullerene-like nanoparticles—Journal of materials research. Nov.;21(11):2726-43.
Tenne R.(2003)—Advances in the synthesis of inorganic nanotubes and fullerene-like nanoparticles—Angewandte Chemie International Edition. Nov. 3;42(42):5124-32.
Weizmann(2016)—Chemical Research Support—electron-microscopy-Weizmann Oct. 11,available at: https://www.weizmann.ac.il/ChemicalResearchSupport/electron- microscopy/instrumentation.
Weizmann(2016)—Chemical Research Support—x-ray-diffraction-Weizmann Aug. 15, available at: https://www.weizmann.ac.il/ChemicalResearchSupport/x-ray-diffraction/about-the-service.
Wichmann, M. H., et al. (2008). On nanocomposite toughness. Composites Science and Technology, 68(1), 329-331.
Yadgarov et al.(2012)—Controlled Doping of MS2 (M=W, Mo) Nanotubes and Fullerene-like Nanoparticles—Angewandte Chemie International Edition.Jan. 27;51(5):1148-51.
Yadgarov et al.(2012)—Investigation of Rhenium-Doped MoS2 Nanoparticles with Fullerene-Like Structure—Zeitschrift für anorganische und allgemeine Chemie. Dec. 1;638(15):2610-6.
Yadgarov et al.(2013)—Tribological studies of rhenium doped fullerene-like Mos2 nanoparticles in boundary, mixed and elasto-hydrodynamic lubrication conditions—Wear. Jan. 15;297(1-2):1103-10.
Yadgarov et al.(2014)—Dependence of the absorption and optical surface plasmon scattering of mos2 nanoparticles on aspect ratio, size, and media—ACS nano. Apr. 2;8(4):3575-83.
Yao et al.(2006)—Anodization: a promising nano-modification technique of titanium implants for orthopedic applications—Journal of nanoscience and nanotechnology.Sep. 1;6(9-10):2682-92.
Zohar, E., et al. (2011). The effect of WS2 nanotubes on the properties of epoxy-based nanocomposites. Journal of Adhesion Science and Technology, 25(13), 1603-1617.

(56) References Cited

OTHER PUBLICATIONS

U.S. Appl. No. 16/970,958 Office Action dated Aug. 2, 2023.

* cited by examiner

HYDROXYAPATITE BASED COMPOSITES AND FILMS THEREOF

CROSS-REFERENCE TO RELATED APPLICATIONS

This application is a Continuation-in-Part application from U.S. application Ser. No. 16/970,958 filed Aug. 19, 2020 which is a National Phase Application of PCT International Application No. PCT/IL2019/050203, International Filing Date Feb. 21, 2019, claiming the benefit of IL. Patent Application No. 257697, filed Feb. 22, 2018 which are hereby incorporated by reference.

FIELD OF THE INVENTION

This invention is directed to composites and films comprising hydroxyapatite, biodegradable polymer, a biocompatible surfactant with inorganic fullerene-like (IF) nanoparticles or inorganic nanotubes (INT); methods of preparation and uses thereof.

BACKGROUND OF THE INVENTION

Self-lubricating solid-state films are used for a variety of applications including the automotive, medical devices, power generation, machining, shipping, aerospace industries as well as many others. Often such films are a nanocomposite made of hard matrix containing a minority phase of a soft metal like copper or silver, or impregnated nanoparticles with good tribological performance [Basnyat, P.; et al. Mechanical and tribological properties of CrAlN—Ag self-lubricating films. *Surf. Coat. Technol.* 2007, 202, 1011-1016].

More recently, self-lubricating films containing carbon nanotubes [Moghadam, A. D.; et al. Mechanical and tribological properties of self-lubricating metal matrix nanocomposites reinforced by carbon nanotubes (CNTs) and graphene-A review. *Compos. Part B* 2015, 77, 402-420], $MoS_2$ [Liu, E. Y.; Wang, W. Z.; Gao, Y. M.; Jia, J. H. Tribological properties of Ni-based self-lubricating composites with addition of silver and molybdenum disulfide. *Tribol. Int.* 2013, 57, 235-241.] and $WS_2$ nanoparticles [Lian, Y.; et al. Friction and wear behavior of $WS_2$/Zr self-lubricating soft coatings in dry sliding against 40Cr-hardened steel balls. *Tribol. Lett.* 2014, 53, 237-246] have been described.

Hydroxyapatite $(Ca_{10}(PO_4)(OH))_2$ is the major component of natural bone. Hydroxyapatite (HA) has many stoichiometric phases, called calcium phosphate phases, with their Ca/P ratio varying between 1.67 and 1.5. Hydroxyapatite (HA, $Ca_{10}(PO_4)_6(OH)_2$) is used as a bone replacement material in a variety of orthopedic implants and artificial prostheses [Petit, R. The use of hydroxyapatite in orthopaedic surgery: A ten-year review. *Eur. J. Orthop. Surg. Traumatol.* 1999, 9, 71-74]. Given the fact that already 15% of the population is above 65 and increasing, artificial orthopedic implants have become a major health issue. However, this material suffers from high wear and poor fracture toughness and is very brittle.

To alleviate these problems various methods were conceived including incorporation of nanoparticles (NP) into the HA films. In particular, HA films containing carbon [Lahiri, D.; et al. Carbon nanotube toughened hydroxyapatite by spark plasma sintering: Microstructural evolution and multiscale tribological properties. *Carbon* 2010, 48, 3103-3120] and boron nitride nanotubes [Lahiri, D.; et al. Boron nitride nanotube reinforced hydroxyapatite composite: Mechanical and tribological performance and in-vitro biocompatibility to osteoblasts. *J. Mech. Behav. Biomed* 2011, 4, 44-56] were prepared by spark plasma sintering technique.

Frequently, HA phase also contains associated minerals and materials, including brushite and portlandite. Brushite—$(CaH(PO_4)\cdot 2H_2O)$ is a metastable compound in physiological conditions and therefore it transforms into hydroxyapatite after implantation of a prostheses [Theiss, F.; Apelt, D.; Brand, B.; Kutter, A.; Zlinszky, K.; Bohner, M. Biocompatibility and resorption of a brushite calcium phosphate cement. *Biomaterials* 2005, 26, 4383-4394].

HA can be synthesized via a hydrothermal reaction of CaO and monetite $(CaHPO_4)$. High concentration of calcium oxide in the reaction leads to the formation of excess portlandite—$Ca(OH)_2$, while low concentration of calcium oxide results in hydroxyapatite [Rodriguez-Lugo, V.; et al. Synthesis and structural characterization of hydroxyapatite obtained from CaO and $CaHPO_4$ by a hydrothermal method. *Mater. Res. Innov.* 2005, 9, 20-22]. Biphasic calcium phosphate (BCP) is an intimate mixture of two phases of HA and β-TCP $(Ca_3(PO_4)_2)$ in variety of ratios, which appears after annealing of HA above 700° C. [Kuo, M. C.; Yen, S. K. The process of electrochemical deposited hydroxyapatite coatings on biomedical titanium at room temperature. *Mater. Sci. Eng. C* 2002, 20, 153-160.].

Poly(L-lactic acid) (PLLA) is a biocompatible, degradable and semi-crystalline polymer. It is one of the most investigated polymers for biodegradable/biocompatible applications including food packaging, medical implants, tissue engineering scaffolds and many more. PLLA can be processed by various techniques, including extrusion, solvent casting, 3D printing, electrospinning, etc.

Nanoslabs (graphene-like) of $MoS_2$ and numerous other layered materials are currently studied intensively for variety of optoelectronic as well as for energy harvesting and energy-storage devices [Manzeli, S.; et al. 2D transition metal dichalcogenides. *Nat. Rev. Mater.* 2 2017, 44, 16399-16404]. $WS_2$ and $MoS_2$ nanoparticles with fullerene-like (IF) structure were found to perform well as solid lubricants [Rapoport, L.; et al. Hollow nanoparticles of $WS_2$ as potential solid-state lubricants. *Nature* 1997, 387, 791-793; (ii) Rosentsveig, R; et al. Fullerene-like $MoS_2$ nanoparticles and their tribological behavior. *Tribol. Lett.* 2009, 36, 175-182]. They are presently used in various commercial products, mostly as additives to lubricating fluids, greases, metal working fluids and in high performance bearings.

Recently, doping of IF-$MoS_2$ nanoparticles with minute amounts (<200 ppm) of rhenium atoms (Re:IF-$MoS_2$) was demonstrated [Yadgarov, L.; et al. Tribological studies of rhenium doped fullerene-like $MoS_2$ nanoparticles in boundary, mixed and elasto-hydrodynamic lubrication conditions. *Wear* 2013, 297, 1103-1110].

One of the most critical aspects of the usage of nanomaterials is their toxicity and biocompatibility. In contrast to various other nanoparticles, the IF NP were found to be non-toxic in general, up to a high dosage (>20 μg/mL). These findings are beneficial for the development of medical technologies based on such nanoparticles.

In the present invention, HA based films are impregnated with doped inorganic fullerene-like (IF) nanoparticles (such as: Re:IF-$WS_2$, Nb:IF-$WS_2$, Re:IF-$MoS_2$, Nb:IF-$MoS_2$) or with doped inorganic nanotubes (INT) (such as: Re:INT-$WS_2$, Nb:NT-$WS_2$, Re:INT-$MoS_2$, Nb:INT-$MoS_2$) leading to substantial improvement in their tribological behavior.

In another aspect, the present invention provides films of PLLA and HA with small amount of inorganic fullerene-like (IF) nanoparticles or inorganic nanotubes (INT) such as: IF-WS$_2$, IF-WS$_2$. IF-MoS$_2$, IF-MoS$_2$ or INT-WS$_2$, INT-WS$_2$, INT-MoS$_2$, INT-MoS$_2$.

SUMMARY OF THE INVENTION

In some embodiments, this invention provides a composite comprising a biodegradable polymer, hydroxyapatite [Ca$_{10}$(PO$_4$)$_6$(OH)$_2$)] nanoparticles, a biocompatible surfactant and inorganic fullerene-like nanoparticles or inorganic nanotubes; wherein the inorganic fullerene-like nanoparticles or inorganic nanotubes is A$_{1-x}$B$_x$-chalcogenide where A is a metal or transition metal or an alloy of one metals or transition metals including at least one of the following: Mo, W, Re, Ti, Zr, Hf, Nb, Ta, Pt, Ru, Rh, In, Ga, InS, InSe, GaS, GaSe, WMo, TiW; and B (dopant) is a metal transition metal selected from the following: Si, Nb, Ta, W, Mo, Sc, Y, La, Hf, Ir, Mn, Ru, Re, Os, V, Au, Rh, Pd, Cr, Co, Fe, Ni; x is between 0 to 0.003; and the chalcogenide is selected from the S, Se, Te. In other embodiments, the biodegradable polymer is poly(lactic acid) (PLA), Poly(L-lactide) (PLLA) or poly-D-lactide (PDLA). In other embodiment the biocompatible surfactant is a fatty acid having between 12-24 carbons. In other embodiments, the biocompatible surfactant is oleic acid (C$_{18}$H$_{34}$O$_2$).

In some embodiments, the composite comprises PLLA (Poly(L-lactic acid), hydroxyapatite [Ca$_{10}$((PO$_4$)$_6$(OH)$_2$)] nanoparticles, oleic acid, and inorganic fullerene-like nanoparticles or inorganic nanotubes; wherein the inorganic fullerene-like nanoparticles or inorganic nanotubes is A$_{1-x}$B$_x$-chalcogenide where A is a metal or transition metal or an alloy of one metals or transition metals including at least one of the following: Mo, W, Re, Ti, Zr, Hf, Nb, Ta, Pt, Ru, Rh, In, Ga, InS, InSe, GaS, GaSe, WMo, TiW; and B (dopant) is a metal transition metal selected from the following: Si, Nb, Ta, W, Mo, Sc, Y, La, Hf, Ir, Mn, Ru, Re, Os, V, Au, Rh, Pd, Cr, Co, Fe, Ni; x is between 0 to 0.003; and the chalcogenide is selected from the S, Se, Te.

In some embodiments, the composite described herein is deposited on a substrate forming a film. In other embodiments, the film is formed by solvent casting. In other embodiments, the film described herein exhibits improved mechanical and thermal properties compared to the films prepared from the PLLA and HA alone, which is advantageous for medical applications. In some other applications the film is used for extruding filaments.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 1A: shows high-resolution scanning electron microscope (HRSEM) micrograph of the Re-doped IF NP powder in In-lens detector 5 kV. The oblate shape of the nanoparticles with smooth surfaces is clearly delineated. The size range of the nanoparticles is 70-170 nm with a minor content (<10%) of NP larger than 200 nm. FIG. 1B shows high-resolution transmission electron microscopy (HRTEM) image of one such nanoparticle made of some 20 closed and nested layers of MoS$_2$. The crystalline perfection and atomically smooth (sulfur-terminated) surface of the IF NP contributes to their excellent mechanical and tribological performance. FIG. 1C shows SEM view of an agglomerate of Re:IF-MoS$_2$ nanoparticles. The synthesized nanoparticles are highly agglomerated and must be deagglomerated before use. Light sonication suffices to disperse them well in aqueous or ethanolic suspensions.

(FIG. 2A) 100 μm; (FIG. 2B) 2 μm. The film is continuous but visibly is heavily cracked.

FIG. 4A presents zeta-potential vs pH for Re:IF-MoS$_2$ nanoparticles in solutions A, B and C. The (positive) zeta-potential of the solutions used for EPD of the HA+IF film are marked by enlarged symbols.

FIG. 4B presents zeta-potential vs pH for Re:IF-MoS$_2$ nanoparticles in different solutions.

FIG. 5A presents the XRD patterns of the different coatings obtained from solution A (1), solution B (2) and solution C (3). FIG. 5B presents XRD pattern of the film obtained from solution A (3 h) after annealing (700° C. for 1 h). Here, a strong crystalline peak associated with calcium pyrophosphate phase (Ca$_2$(P$_2$O$_7$)) is observed. This phase is obtained through water evaporation from the HA (Ca$_{10}$(PO$_4$)$_6$(OH)$_2$) film. The presence of the Re:IF-MoS$_2$ nanoparticles did not change appreciably upon annealing, suggesting that these NPs are thermally stable at the annealing conditions.

(FIG. 14B) and 1 µm, the arrows point to pits formed by pull-out of the HA agglomerates during breaking of the film (FIG. 14C).

Figure 1A:
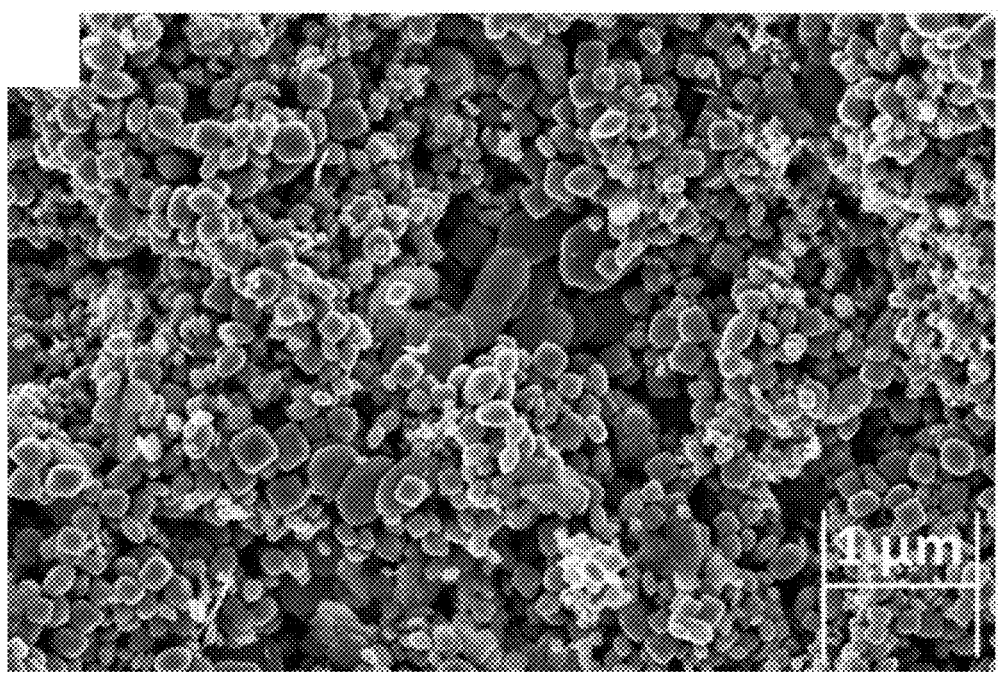
FIGS. 1A-1C present SEM images of Re:IF-MoS$_2$ nanoparticles.
Figure 1B:
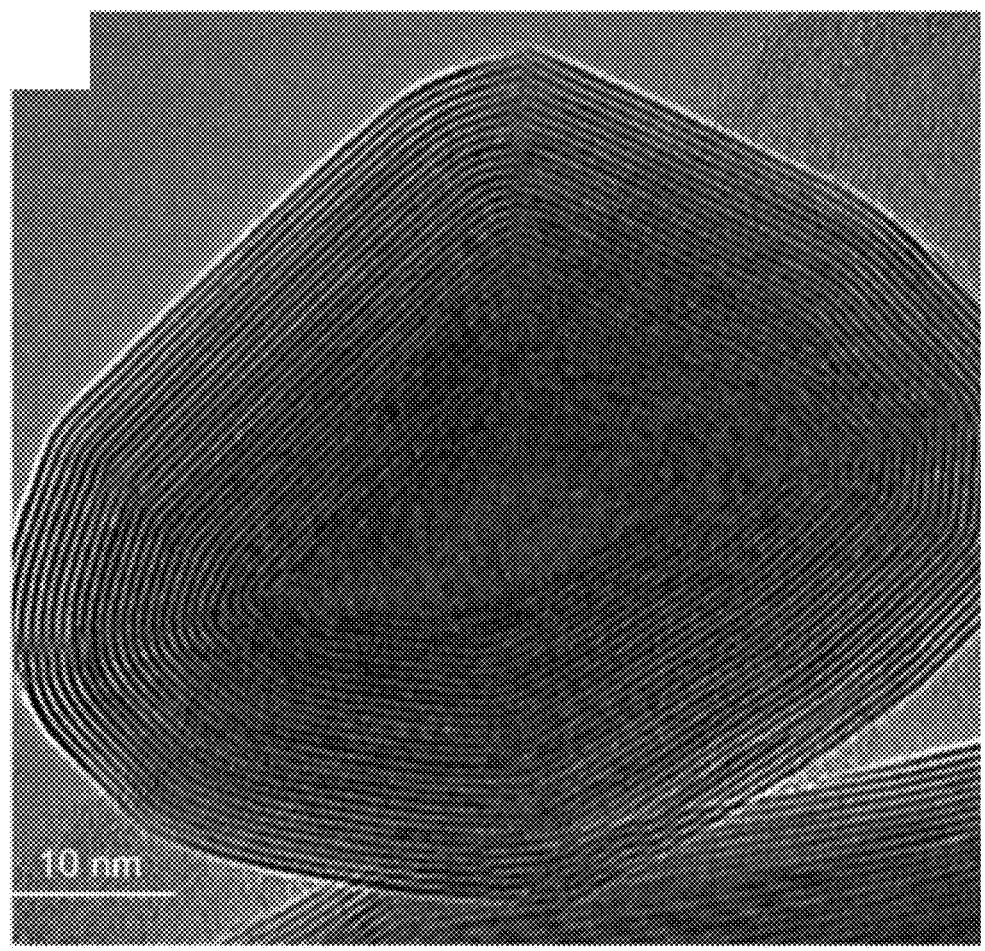

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In some embodiments, this invention is directed to a composition comprising hydroxyapatite [$Ca_{10}(PO_4)_6(OH)_2$] and doped inorganic fullerene-like nanoparticles (IF-NPs) or doped inorganic nanotubes (INT).

In some embodiments, this invention is directed to a film comprising hydroxyapatite [$Ca_{10}(PO_4)_6(OH)_2$] and doped inorganic fullerene-like nanoparticles (IF-NPs) or doped inorganic nanotubes (INTs).

In some embodiments, this invention provides a composite comprising PLLA (Poly(L-lactic acid), hydroxyapatite [$Ca_{10}(PO_4)_6(OH)_2$] nanoparticles and inorganic fullerene-like nanoparticles or inorganic nanotubes; wherein the inorganic fullerene-like nanoparticles or inorganic nanotubes is $A_{1-x}B_x$-chalcogenide where A is a metal or transition metal or an alloy of one metals or transition metals including at least one of the following: Mo, W, Re, Ti, Zr, Hf, Nb, Ta, Pt, Ru, Rh, In, Ga, InS, InSe, GaS, GaSe, WMo, TiW; and B(dopant) is a metal transition metal selected from the following: Si, Nb, Ta, W, Mo, Sc, Y, La, Hf, Ir, Mn, Ru, Re, Os, V, Au, Rh, Pd, Cr, Co, Fe, Ni; x is between 0 to 0.003; and the chalcogenide is selected from the S, Se, Te.

In some embodiments, this invention provides a composite comprising a biodegradable polymer, hydroxyapatite [$Ca_{10}(PO_4)_6(OH)_2$] nanoparticles, a biocompatible surfactant and inorganic fullerene-like nanoparticles or inorganic nanotubes; wherein the inorganic fullerene-like nanoparticles or inorganic nanotubes is $A_{1-x}B_x$-chalcogenide where A is a metal or transition metal or an alloy of one metals or transition metals including at least one of the following: Mo, W, Re, Ti, Zr, Hf, Nb, Ta, Pt, Ru, Rh, In, Ga, InS, InSe, GaS, GaSe, WMo, TiW; and B (dopant) is a metal transition metal selected from the following: Si, Nb, Ta, W, Mo, Sc, Y, La, Hf, Ir, Mn, Ru, Re, Os, V, Au, Rh, Pd, Cr, Co, Fe, Ni; x is between 0 to 0.003; and the chalcogenide is selected from the S, Se, Te. In other embodiments, the biodegradable polymer is poly(lactic acid) (PLA), Poly(L-lactide) (PLLA) or poly-D-lactide (PDLA). In other embodiment the biocompatible surfactant is a fatty acid having between 12-24 carbons. In other embodiments, the biocompatible surfactant is oleic acid ($C_{18}H_{34}O_2$).

In some embodiments, the biocompatible surfactants refer to surface active group of amphiphilic molecules which are manufactured by chemical processes or purified from natural sources or processes. These can be anionic, cationic, non-ionic, and zwitterionic.

A variety of biocompatible surfactants include a fatty acid, arabic gum, poloxamer, poloxamines, pluronic acid, PEG, Tween-80, gelatin, dextran, pluronic L-63, PVA, methylcellulose, lecithin and DMAB, vitamin E TPGS (D-α-tocopheryl polyethylene glycol 1000 succinate), phospholipid compounds or phospholipid mixtures (phospholipid choline (lecithin), such as lecithin of soy or egg), sorbitan, such as fatty acid-substituted sorbus, a sugar alcohol surfactant (available commercially under the name of SPAN® or ARLACEL®), a fatty acid ester of polyethoxylated sorbitol (TWEEN®), a polyethylene glycol derived from fatty acids such as castor oil Ester (EMULFOR): polyethoxylated fatty acids (for example, stearic acid available under SIMULSOL M-53), polyethoxylated isooctylphenol/formaldehyde polymer (TYLOXAPOL), polyoxyethylene fat Alcohol ethers (BRIJ®); polyoxyethylene phenyl ether (TRITON®); polyoxyethylene isooctyl phenyl ether (TRITON® X).

In some embodiments, the composite comprises PLLA (Poly(L-lactic acid), hydroxyapatite [$Ca_{10}(PO_4)_6(OH)_2$] nanoparticles, oleic acid, and inorganic fullerene-like nanoparticles or inorganic nanotubes; wherein the inorganic fullerene-like nanoparticles or inorganic nanotubes is $A_{1-x}B_x$-chalcogenide where A is a metal or transition metal or an alloy of one metals or transition metals including at least one of the following: Mo, W, Re, Ti, Zr, Hf, Nb, Ta, Pt, Ru, Rh, In, Ga, InS, InSe, GaS, GaSe, WMo, TiW; and B (dopant) is a metal transition metal selected from the following: Si, Nb, Ta, W, Mo, Sc, Y, La, Hf, Ir, Mn, Ru, Re, Os, V, Au, Rh, Pd, Cr, Co, Fe, Ni; x is between 0 to 0.003; and the chalcogenide is selected from the S, Se, Te.

Incorporated hydroxyapatite in the PLLA matrix improves the flexibility of the bioceramic HA and consequently, produce biodegradable ceramic-polymer composites, which is an alternative to the traditional materials used for implants or bone repair and for tissue engineering. However, both PLLA and HA and their composites, suffer from low toughness, which limit their application in the human body. Reinforcing the PLLA/HA composite with inorganic fullerene-like nanoparticles (IF-NPs) or inorganic nanotubes (INT) (such as INT-WS$_2$) can remedy this disadvantage. The INT-WS$_2$ are multiwall nanostructures 1-20 µm long with diameter of 30-150 nm (aspect ratio of 50-100 and even larger). They are nontoxic with very good mechanical properties (Young's modulus 150-170 GPa, bending modulus of 217 GPa, tensile strength between 10-22 GPa, and strain ε>10%).

HA does not disperse well in the PLLA matrix and tend to agglomerate as secondary particles a few micrometers in size. This is because HA is hydrophilic, while the organic solvents used to dissolve the polymers are mostly hydrophobic. However, a biocompatible surfactant such as oleic acid (OA), which is an amphiphilic surfactant, used to mediate the interaction between the HA (hydrophilic ceramic) and hydrophobic polymer, like PLLA. Therefore, oleic acid induces a homogeneous dispersion of the HA in the PLLA matrix.

In some embodiments, this invention is directed to a film comprising the composition/composite of this invention.

In some embodiments, this invention is directed to a film comprising hydroxyapatite [$Ca_{10}(PO_4)_6(OH)_2$)] and doped inorganic fullerene-like nanoparticles (IF-NPs) or doped inorganic nanotubes (INT), wherein the film is coated on a solid substrate.

In some embodiments, this invention is directed to a film comprising a biodegradable polymer, hydroxyapatite [$Ca_{10}(PO_4)_6(OH)_2$)] nanoparticles, a biocompatible surfactant, and inorganic fullerene-like nanoparticles or inorganic nanotubes; wherein the inorganic fullerene-like nanoparticles or inorganic nanotubes is $A_{1-x}B_x$-chalcogenide where A is a metal or transition metal or an alloy of one metals or transition metals including at least one of the following: Mo, W, Re, Ti, Zr, Hf, Nb, Ta, Pt, Ru, Rh, In, Ga, InS, InSe, GaS, GaSe, WMo, TiW; and B (dopant) is a metal transition metal selected from the following: Si, Nb, Ta, W, Mo, Sc, Y, La, Hf, Ir, Mn, Ru, Re, Os, V, Au, Rh, Pd, Cr, Co, Fe, Ni; x is between 0 to 0.003; and the chalcogenide is selected from the S, Se, Te.

In some embodiments, this invention is directed to a film comprising PLLA (Poly(L-lactic acid), hydroxyapatite [$Ca_{10}(PO_4)_6(OH)_2$)] nanoparticles, oleic acid, and inorganic fullerene-like nanoparticles or inorganic nanotubes; wherein the inorganic fullerene-like nanoparticles or inorganic nanotubes is $A_{1-x}B_x$-chalcogenide where A is a metal or transition metal or an alloy of one metals or transition metals including at least one of the following: Mo, W, Re, Ti, Zr, Hf, Nb, Ta, Pt, Ru, Rh, In, Ga, InS, InSe, GaS, GaSe, WMo, TiW; and B (dopant) is a metal transition metal selected from the following: Si, Nb, Ta, W, Mo, Sc, Y, La, Hf, Ir, Mn, Ru, Re, Os, V, Au, Rh, Pd, Cr, Co, Fe, Ni; x is between 0 to 0.003; and the chalcogenide is selected from the S, Se, Te.

In other embodiments, the inorganic nanotubes (INT) are WS$_2$.

In other embodiments, the inorganic fullerene-like nanoparticles (IF-NPs) or the inorganic nanotubes (INT) are doped by rhenium and niobium.

Inorganic Fullerene-like (IF) nanoparticles and/or inorganic nanotubes (INT) of this invention each having the formula $A_{1-x}B_x$-chalcogenide wherein A is a metal or transition metal or an alloy of one metals or transition metals including at least one of the following: Mo, W, Re, Ti, Zr, Hf, Nb, Ta, Pt, Ru, Rh, In, Ga, InS, InSe, GaS, GaSe, WMo, TiW; and B (dopant) is a metal transition metal selected from the following: Si, Nb, Ta, W, Mo, Sc, Y, La, Hf, Ir, Mn, Ru, Re, Os, V, Au, Rh, Pd, Cr, Co, Fe, Ni; and x is below or equal 0.003, and the chalcogenide is selected from the S, Se, Te. In other embodiments, x is below or equal 0.001.

For example, doped IF-NP or doped INT of the invention may be IF-Mo$_{1-x}$Nb$_x$S$_2$, IF-Mo$_{1-x}$Re$_x$S$_2$, INT-Mo$_{1-x}$Nb$_x$S$_2$, INT-Mo$_{1-x}$Re$_x$S$_2$, IF-W$_{1-x}$Nb$_x$S$_2$, IF-W$_{1-x}$Re$_x$S$_2$, INT-W$_{1-x}$Nb$_x$S$_2$, INT-W$_{1-x}$Re$_x$S$_2$ or the alloys of WMoS$_2$, WMoSe$_2$, TiWS$_2$, TiWSe$_2$, where Nb or Re are doped therein. Within the alloys of the invention, taking WMo, TiW for example, the ratio between W and Mo or Ti and W may be 0.65-0.75 of one metal or transition metal and 0.25-0.35 of the other metal or transition metal, e.g. $W_{0.7}Mo_{0.29}Nb_{0.01}S_2$ (given with the percentage of the Nb dopant).

In one embodiment, the rhenium or niobium atoms serve as dopants in the lattice of the IF-NPs/INTs. The dopants substitute for the molybdenum or tungsten atoms, which lead to an excess of negative charge carriers being trapped on the IF-NPs/NT surfaces.

In other embodiments, the concentration of the dopants is below or equal to 0.3 at %. In other embodiments, the concentration of the dopants is between 0.01 to 0.1 at %. In other embodiments, the concentration of the dopants is between 0.01 to 0.07 at/o. In other embodiments, the concentration of the dopants is between 0.01 to 0.05 at %.

The doped IF-nanoparticles/inorganic nanotubes behave like charged colloids, which do not agglomerate and form stable suspensions in oils and various fluids. This is in contrast to the undoped IF-NPs/INTs, as their structure allows rolling. Additionally, the doped IF-NPs and doped INTs have higher conductivity, higher carrier density, lower activation energy, and lower resistance than the undoped ones.

In some embodiments, this invention is directed to a composition/composite or a film comprising hydroxyapatite [$Ca_{10}(PO_4)_6(OH)_2$), HA] and doped IF-NPs/doped INTs. In other embodiment, the composition of the film further comprises brushite, portlandite, other HA minerals or combination thereof.

In some embodiments, this invention is directed to a composition/composite and/or a film comprising hydroxyapatite [$Ca_{10}(PO_4)_6(OH)_2$), HA] and doped IF-NPs or doped INTs. In other embodiment, the concentration of the doped IF-NPs or doped INTs is between 0.2 wt % to 5 wt % of the composition and/or film. In other embodiment, the concentration of the doped IF-NPs or doped INTs is between 0.2 wt % to 2 wt % of the composition and/or film. In other embodiment, the concentration of the doped IF-NPs or doped INTs is between 0.2 wt % to 1 wt %. In other embodiment, the concentration of doped IF-NPs or doped INTs is between 0.2 wt % to 1.5 wt %. In other embodiment, the concentration of the doped IF-NPs or doped INTs is between 0.5 wt % to 1.5 wt %. In other embodiment, the concentration of the doped IF-NPs or doped INTs is between 0.5 wt % to 2 wt %. In other embodiment, the concentration of the doped IF-NPs or doped INTs is between 1 wt % to 5 wt %. In other embodiment, the concentration of the doped IF-NPs or doped INTs is between 0.5 wt % to 3 wt %. In other embodiment, the concentration of the doped IF-NPs or doped INTs is between 1.5 wt % to 5 wt %.

In some embodiments, this invention is directed to a composition/composite and/or a film comprising PLLA (Poly(L-lactic acid), hydroxyapatite [$Ca_{10}(PO_4)_6(OH)_2$)] nanoparticles, and inorganic fullerene-like nanoparticles or inorganic nanotubes; wherein the inorganic fullerene-like nanoparticles or inorganic nanotubes is $A_{1-x}B_x$-chalcogenide where A is a metal or transition metal or an alloy of one metals or transition metals including at least one of the following: Mo, W, Re, Ti, Zr, Hf, Nb, Ta, Pt, Ru, Rh, In, Ga, InS, InSe, GaS, GaSe, WMo, TiW; and B (dopant) is a metal transition metal selected from the following: Si, Nb, Ta, W, Mo, Sc, Y, La, Hf, Ir, Mn, Ru, Re, Os, V, Au, Rh, Pd, Cr, Co, Fe, Ni; x is between 0 to 0.003; and the chalcogenide is selected from the S, Se, Te; wherein the concentration of inorganic fullerene-like nanoparticles or inorganic nanotubes is between 0.1 wt % to 5 wt % of the composition. In other embodiments, the concentration of HA is between 20 wt % to 60 wt % of the composition.

In some embodiments, this invention is directed to a composition/composite and/or a film comprising PLLA (Poly(L-lactic acid), hydroxyapatite $[Ca_{10}(PO_4)_6(OH)_2)]$ nanoparticles, oleic acid and inorganic fullerene-like nanoparticles or inorganic nanotubes; wherein the inorganic fullerene-like nanoparticles or inorganic nanotubes is $A_{1-x}B_x$-chalcogenide where A is a metal or transition metal or an alloy of one metals or transition metals including at least one of the following: Mo, W, Re, Ti, Zr, Hf, Nb, Ta, Pt, Ru, Rh, In, Ga, InS, InSe, GaS, GaSe, WMo, TiW; and B (dopant) is a metal transition metal selected from the following: Si, Nb, Ta, W, Mo, Sc, Y, La, Hf, Ir, Mn, Ru, Re, Os, V, Au, Rh, Pd, Cr, Co, Fe, Ni; x is between 0 to 0.003; and the chalcogenide is selected from the S, Se, Te; wherein the concentration of inorganic fullerene-like nanoparticles or inorganic nanotubes is between 0.1 wt % to 5 wt % of the composition. In other embodiments, the concentration of HA is between 20 wt % to 60 wt % of the composition.

In some embodiments, this invention is directed to a composite and/or a film comprising a biodegradable polymer, a biocompatible surfactant, hydroxyapatite $[Ca_{10}(PO_4)_6(OH)_2)]$ nanoparticles, and inorganic fullerene-like nanoparticles or inorganic nanotubes; wherein the inorganic fullerene-like nanoparticles or inorganic nanotubes is $A_{1-x}B_x$-chalcogenide where A is a metal or transition metal or an alloy of one metals or transition metals including at least one of the following: Mo, W, Re, Ti, Zr, Hf, Nb, Ta, Pt, Ru, Rh, In, Ga, InS, InSe, GaS, GaSe, WMo, TiW, and B (dopant) is a metal transition metal selected from the following: Si, Nb, Ta, W, Mo, Sc, Y, La, Hf, Ir, Mn, Ru, Re, Os, V, Au, Rh, Pd, Cr, Co, Fe, Ni; x is between 0 to 0.003; and the chalcogenide is selected from the S, Se, Te; wherein the concentration of inorganic fullerene-like nanoparticles or inorganic nanotubes is between 0.1 wt % to 5 wt % of the composition. In another embodiment between 0.1 wt % to 1 wt %. In another embodiment between 0.2 wt % to 1 wt %. In another embodiment between 0.1 wt % to 2 wt %. In another embodiment between 0.1 wt % to 3 wt %. In another embodiment between 0.5 wt % to 3 wt %. In another embodiment between 0.5 wt % to 2 wt %. In another embodiment between 1 wt % to 5 wt %. In another embodiment, the biodegradable polymer is PLLA. In another embodiment, the biocompatible surfactant is oleic acid.

In some embodiments, this invention is directed to a composition and/or a film comprising a biodegradable polymer, a biocompatible surfactant, hydroxyapatite $[Ca_{10}(PO_4)_6(OH)_2)]$ nanoparticles, and inorganic fullerene-like nanoparticles or inorganic nanotubes; wherein the inorganic fullerene-like nanoparticles or inorganic nanotubes is $A_{1-x}B_x$-chalcogenide where A is a metal or transition metal or an alloy of one metals or transition metals including at least one of the following: Mo, W, Re, Ti, Zr, Hf, Nb, Ta, Pt, Ru, Rh, In, Ga, InS, InSe, GaS, GaSe, WMo, TiW; and B (dopant) is a metal transition metal selected from the following: Si, Nb, Ta, W, Mo, Sc, Y, La, Hf, Ir, Mn, Ru, Re, Os, V, Au, Rh, Pd, Cr, Co, Fe, Ni; x is between 0 to 0.003; and the chalcogenide is selected from the S, Se, Te; wherein the concentration of HA is between 20 wt % to 60 wt % of the composition. In another embodiment between 20 wt % to 30 wt %. In another embodiment between 20 wt % to 40 wt %. In another embodiment between 20 wt % to 50 wt %. In another embodiment between 30 wt % to 40 wt %. In another embodiment between 30 wt % to 50 wt %/o. In another embodiment between 30 wt % to 60 wt %. In another embodiment, the biodegradable polymer is PLLA. In another embodiment, the biocompatible surfactant is oleic acid.

The term "composite" or "composition" is used herein interchangeably referring to hydroxyapatite is embedded in different matrices (biodegradable polymers), such as the PLLA. The composite/composition of this invention further comprises inorganic particles such as inorganic fullerene-like nanoparticles or inorganic nanotubes and a biocompatible surfactant (i.e. oleic acid)

In some embodiments, this invention is directed to a film comprising PLLA (Poly(L-lactic acid), hydroxyapatite $[Ca_{10}(PO_4)_6(OH)_2)]$ nanoparticles, oleic acid and inorganic fullerene-like nanoparticles or inorganic nanotubes; wherein the inorganic fullerene-like nanoparticles or inorganic nanotubes is $A_{1-x}B_x$-chalcogenide where A is a metal or transition metal or an alloy of one metals or transition metals including at least one of the following: Mo, W, Re, Ti, Zr, Hf, Nb, Ta, Pt, Ru, Rh, In, Ga, InS, InSe, GaS, GaSe, WMo, TiW; and B (dopant) is a metal transition metal selected from the following: Si, Nb, Ta, W, Mo, Sc, Y, La, Hf, Ir, Mn, Ru, Re, Os, V, Au, Rh, Pd, Cr, Co, Fe, Ni; x is between 0 to 0.003; and the chalcogenide is selected from the S, Se, Te; wherein the film is prepared by solvent casting on a solid surface, wherein the film HA nanoparticles and the organic fullerene-like nanoparticles or inorganic nanotubes within the film are dispersed in the PLLA.

In other embodiments, the film provides Young's modulus being 1.5 to 3 times higher compared to a film comprising PLLA and HA. In other embodiments, the film provides a toughness being 2 to 10 times higher compared to a film comprising PLLA and HA. In other embodiments, the film provides a hardness being 1.5 to 3 times higher compared to PLLA film. In other embodiment, the film provides higher thermal stability compared to a PLLA film or a film comprising PLLA and HA. In other embodiment, there is no chemical bonding between each of the PLLA, HA and the inorganic fullerene-like nanoparticles or inorganic nanotubes.

In some embodiments the composite described herein The composite of claim 6, wherein the film provides an improved hardness by 1.2 to 3, Young Modules by 1.5 to 3, Toughness by 2 to 5, Yield Strength by 1.2 to 3 and Strain at failure by 1.1 to 3 compared to PLLA film.

In other embodiments, the film is formed by mixing each of PPLA, HA and INT or IF in an organic solvent followed solvent casting on a solid substrate and drying the formed film. In another embodiment, the organic solvent is chloroform, THF or mixtures thereof. In other embodiment, the oleic acid is used to homogenize the mixture between the HA phase and the other two components (PLLA and INT/IF). In other embodiments, minute amounts of a solvent remain in the film. In other embodiments, no solvent remains in the film. In other embodiments, other means of film formation include hot-pressing, or extrusion and subsequent 3D printing.

The control of the interfacial interaction between the two majority phases, i.e. PLLA and HA and the minority phase—INT-$WS_2$ has major implications on the mechanical stability of the nanocomposite subdued to different stress and environmental conditions. The oleic acid, which is used for compatelizing HA in different polymer phases, was found to be indispensable. First, both oleic acid and HA nanoparticles are non-toxic and biocompatible phases. The FTIR, XRD and Raman measurements as presented in Example 6 do not reveal any specific chemical bonding between each of the four components (PLLA, HA, OA and INT) or a new phase forming during the preparation of the film.

It remains to be seen if other specific functionalization processes of the nanotubes surface could further improve their interfacial interaction with the matrix and influence the mechanical behavior of the nanocomposite without sacrificing its biocompatibility. The INT and IF within the compositions described herein have no specific interaction with the polymer-HA, their large surface area and aspect ratio (50-100) as well as their mechanical strength (10-22 GPa), large strain (10%), non-toxic nature and their facile dispersion make the INT/IF suited for reinforcing biodegradable polymer, even if added in minute amounts (~0.1 wt %~5 wt %).

In some embodiment, the film of this invention is coated on a solid substrate. In other embodiments, the film described herein is formed by solvent casting. In other embodiment, the solid substrate is biocompatible. In other embodiments, the solid substrate is metallic biocompatible. In other embodiments the solid and biocompatible substrate is titanium, alloys of titanium, $Ti_6Al_4V$, Co—Cr alloys, magnesium, stainless steel, shape memory alloys of nickel-titanium, silver, tantalum, zirconium, novel ceramics such as alumina or zirconia or any other electrical-conductive substrate.

In other embodiment, the titanium is porous.

In other embodiment, to improve the coating of the film onto the solid substrate the composition and/or film further comprises a cationic surfactant. In other embodiment a cationic surfactant comprises an ammonium group. Non limiting examples of cationic surfactant include: alkyltrimethylammonium salts: cetyl trimethylammonium bromide (CTAB) and cetyl trimethylammonium chloride (CTAC); benzalkonium chloride (BAC); cetylpyridinium chloride (CPC) or benzethonium chloride (BZT).

In other embodiment, to improve the coating of the film to the solid substrate the composition and/or film further comprises a polymeric binder. In other embodiments a non-limiting example of a polymer binder include a poly (lactic acid) (PLAs) based polymer.

In some embodiments this invention provides methods for coating a solid substrate with the composition of this invention to form a film on a solid substrate. In other embodiments, the methods of coating include; (i) electrophoretic deposition (solution); (ii) plasma spray (in vacuum); (iii) ion beam coating (in vacuum); (iv) e-beam evaporation [Cen Chen et al. Biomimetic apatite formation on calcium phosphate-coated titanium in Dulbecco's phosphate-buffered saline solution containing $CaCl_2$) with and without fibronectin, *Acta Biomaterialia*, (2010) 6, 2274-2281]; (v) thermal deposition; vacuum deposition [D. Predoi et al. Characteristics of hydroxyapatite thin films, *J. Optoelect and Adv. Mat.*, (2007), 9(12), 3827-3831]; (vi) physical vapor deposition (PVD) [Ohad Goldbart et al. New Deposition Technique for Metal Films Containing Inorganic Fullerene-Like (IF) Nanoparticles, *Chem Phys Chem*, (2013), 14, 2125-2131; Olga Elianov MSc thesis submitted to the Faculty of Dental Medicine, Hadassah-Hebrew University, Jerusalem 91120, Israel (March 2018); (vii) aerosol deposition [C. Piccirillo, et al. Aerosol assisted chemical vapour deposition of hydroxyapatite-embedded titanium dioxide composite thin films, *J. of photochem. And photobiol. A: Chemistry* (2017), 332, 45-53]; (viii) sol gel deposition (ix) dip coating; or (x) solvent casting. Each represents a separate embodiment of this invention.

Electrophoretic Deposition:

The electrophoresis coating technique is an inexpensive process capable of a high deposition rate while maintaining control of the coating thickness and morphology on the metal. In addition, this technique has a wide range of materials permitting coating of variety of shapes and sizes, all resulting in a quality surface with uniform thickness. The electrophoresis coating technique also has high material efficiency and can perform at low temperatures. The electrophoresis coating technique requires several steps, including surface treatments, which are used to clean the electrode from contaminants, improve the mechanical properties to create a uniform coating, and achieve better adhesion deposition. Electrophoresis coating is performed by dipping two electrodes into a container of electrolyte solution. A constant power supply creates an electrical field in the solution, which moves the charging colloid toward the opposite electrode. The deposition is obtained by chemical oxidation and reduction. The final step is an annealing process, and is done to achieve a smooth and continuous coating characterized by good adhesion to the surface. The electrophoretic deposition for coating the composition of this invention on a porous solid substrate is conducted at a relatively low temperature using an aqueous electrolyte containing calcium and phosphate salts. In this method, the calcium phosphate is deposited on the cathode as a result of a pH increase in the vicinity of the cathode and by the reduction of the $H^+$ ion accompanying the generation of $H_2$ gas and $OH^-$ ions. The production of $H_2$ on the cathode's surface inhibits the nucleation or absorption of calcium phosphate on the cathode. Adding an alcohol such as ethanol to the electrolyte solution resolves this problem.

In some embodiment, this invention provides a method of coating a metal substrate with the composition of this invention, wherein the method comprises electrophoretic deposition having an electrolyte comprising a calcium salt, a phosphate salt and doped inorganic fullerene like nanoparticles, and thereby forming a film of desirable composition on the substrate.

The coating process of the film of this invention depends on achieving the proper pH solution that allows quality coatings, which in turn, relies on the nanoparticles' zeta potential measurement. In other embodiment, the composition has a positive zeta potential at pH below 6.5. In neutral pH (7) the nanoparticles are negatively charged, which reflects the extra negative charge induced by native defects in the lattice and chemisorbed negatively charged moieties, like OH— groups. This extra negative charge is neutralized in very low pH (up to pH=2) by positively charged chemical moieties, like protons, etc. In either very low and very high pH, the Debye screening radius is very small (few nm) leading to agglomeration of the nanoparticles and their precipitation. Thus, the electrophoresis coating process of the composition of this invention is performed at pH 6-7 to: 1) avoid damaging the surface of the nanoparticles; 2) provide a stable working solution; and 3) achieve a uniform coating of the substrate. Within this pH range, the nanoparticles gained a negative charge and the deposition was performed on the anode.

In some embodiments the methods for coating a metal substrate with the composition of this invention is performed by electrophoretic deposition. In another embodiment, the metal substrate is pretreated for example with carbon paper to obtain a smooth surface and then the metal substrate is anodized prior to the electrophoretic deposition. In other embodiment, the metal substrate is anodized in electrolyte solution containing a fluoride ion. In other embodiment, the electrophoretic deposition is conducted as presented in Example 1.

Anodization is an electrochemical method for producing a protective layer on metal by forming a metal oxide layer which makes the metal substrate biocompatible. The metal oxide layer is a few tens of microns thick with micro pores to maintain homogeneity. The anodization process creates a porous surface, which improves and increases osseointegration (the functional connection between the human bone and the implant), and thereby increase the osteoblast adhesion (bone cell).

In another embodiment the electrophoretic deposition (EPD) is conducted between 2 to 5 hours. In another embodiment the electrophoretic deposition is conducted for 2, 3, 4 or 5 hours. Each represents a separate embodiment of this invention.

In some embodiments, this invention provides HA coatings containing up to 5 wt % doped IF-NPs or doped INTs deposited on a porous metallic biocompatible substrate by electrophoretic deposition using DC bias. The major phase in each coating is hydroxyapatite which incorporates small amounts of doped IF-NPs or doped INTs. In other embodiments, the metal substrate was a titanium substrate. In other embodiments, the doped inorganic fullerene-like nanoparticle is Re:IF-$MoS_2$. In other embodiments, the doped inorganic fullerene-like nanoparticle is Re:IF-W $S_2$. In other embodiments, the doped inorganic fullerene-like nanoparticle is Nb:IF-$MoS_2$. In other embodiments, the doped inorganic fullerene-like nanoparticle is Nb:IF-$WS_2$. In other embodiments, the doped inorganic nanotube is Re:INT-$MoS_2$. In other embodiments, the doped inorganic nanotube is Re:INT-$WS_2$. In other embodiments, the doped inorganic nanotube is Nb:INT-$MoS_2$. In other embodiments, the doped inorganic nanotube is Nb:INT-$WS_2$.

In some embodiments, the film formed on the metal substrate has low friction coefficient of between 0.05 to 0.15. In another embodiment, the film formed by EPD on the metal substrate has low friction coefficient of between 0.05 to 0.1. In another embodiment, the low friction is maintained after annealing. In another embodiment, the film maintains its mechanical robustness.

Uses Thereof

Artificial bone implants became a major health concern. Hydroxyapatite ($Ca_{10}(PO_4)_6(OH)_2$; HA) is the main constituency of the bone. Hydroxyapatite, is chemically similar to the calcium phosphate mineral present in bone and biological hard tissue.

The composition/composite and film of this invention are bioceramic suitable for implants and bone repair, and for tissue engineering.

In some embodiments, this invention provides an implant, a bone repair or a tissue engineering comprising the composition/composite described herein.

The composition/composite and film of this invention are for use in dental and orthopedic implants having very low friction, good adhesion to the underlying rough substrate even under very high load (600 MPa). The composition and film of this invention have high biocompatibility, specifically as a bone substitute. The composition/film prepared by the methods of this invention form a homogeneous structure, having slow degradability rate and both osseointegration and osteoconductive characteristics, which improve bone growth.

In some embodiments, this invention provides a dental or orthopedic implant comprising the composition of this invention. In other embodiments, this invention provides a dental or orthopedic implant comprising a film on a biocompatible substrate, wherein the film comprises the composition of this invention.

In some embodiments, this invention provides a bone regeneration therapy comprising administering an artificial bone implant comprising the composition of this invention.

In some embodiments, this invention provides a method of osseointegration comprising contacting an artificial bone implant comprising the composition of this invention in a bone needs to be improved. In other embodiments, the artificial bone implant comprises a biocompatible substrate coated by a film, wherein the film comprises the composition of this invention.

The methods of this invention for osseointegration or for bone regeneration provide fast fixation and spontaneous binding of the HA to neighboring bone, having osteoconductive properties, resulting in deposition of biological apatite on the surface of the implant and thereby bone healing around the implant.

The following examples are presented in order to more fully illustrate the preferred embodiments of the invention. They should in no way be construed, however, as limiting the broad scope of the invention.

EXAMPLES

Example 1

Preparation of a Film of Hydroxyapatite (HA) and Rhenium Doped Fullerene Like $MoS_2$ (Re:IF-$MoS_2$) on Titanium Substrate A titanium electrode (30×5×0.3 mm, 97 wt % purity) was polished with silicon carbide paper to a mirror finish. It was subsequently cleaned by sonicating in a series of solvents, i.e., acetone, ethanol, methanol, isopropanol and finally distilled water, then dried under a nitrogen stream.

Figure 11A:
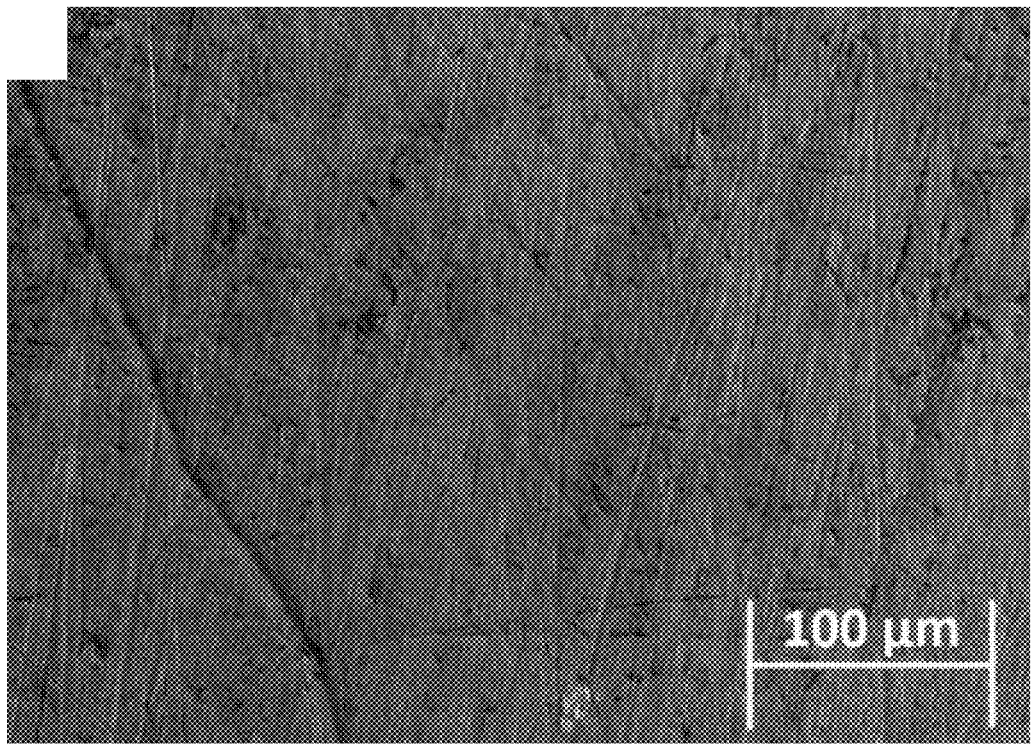
Figure 11B:
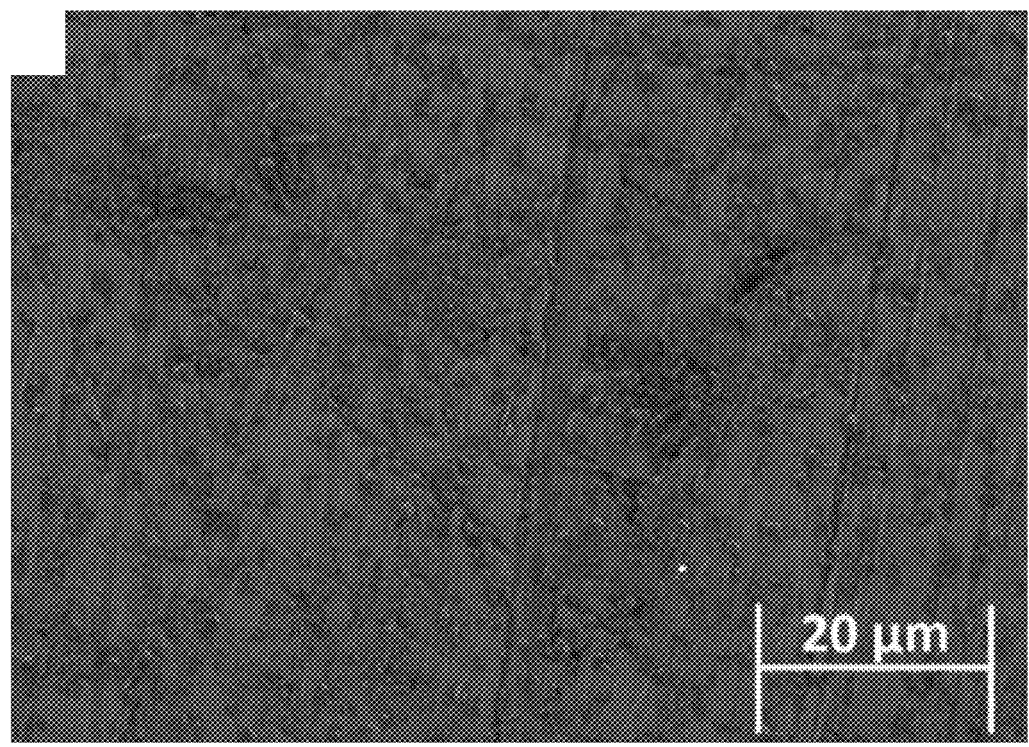
Figure 11C:
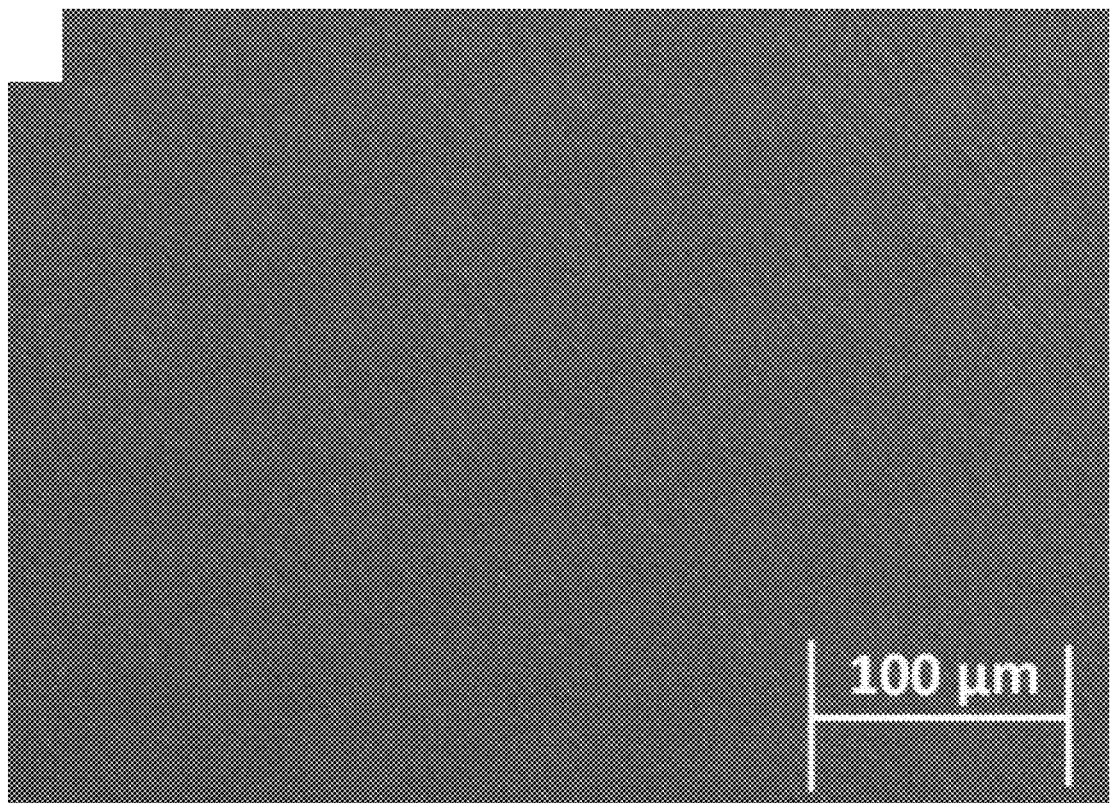
Figure 11D:
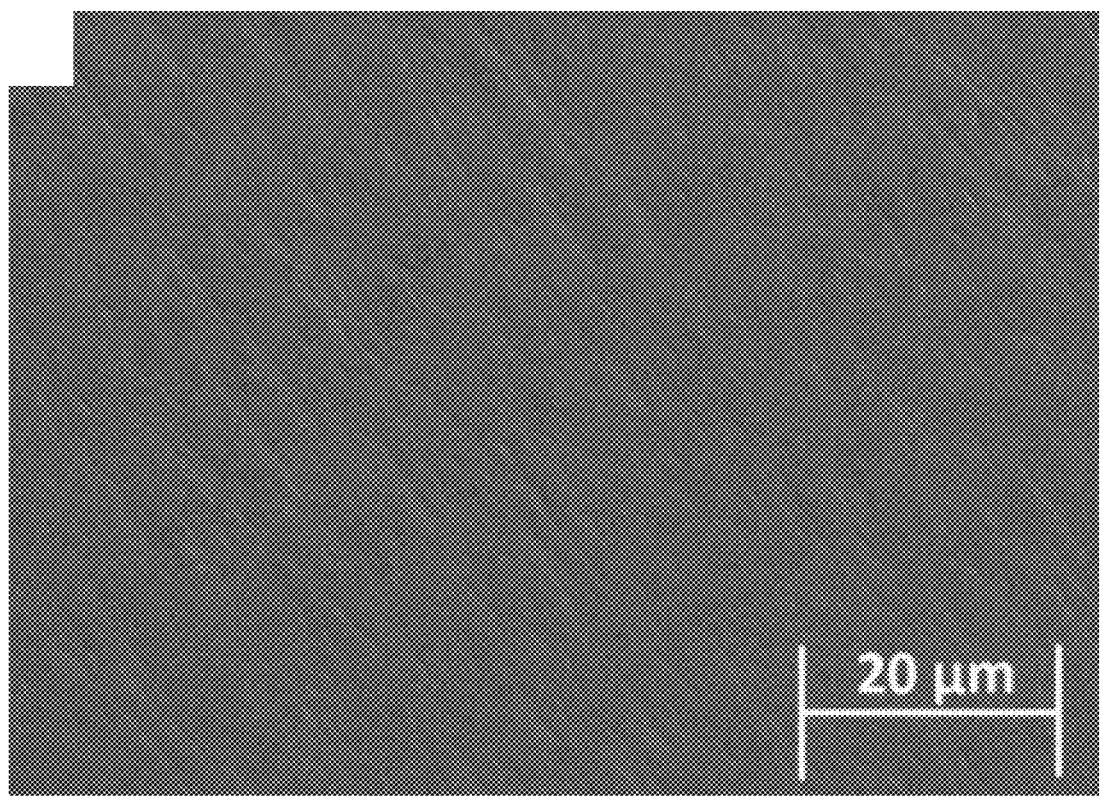

The surface morphology of the titanium before the pretreatment preceding the anodization is presented in FIGS. 11A-11B. Visibly, the fresh surface was heavily contaminated with a dense network of scratches. After treatment of the titanium with different solvents, a smooth surface with low density of scratches and clean from contaminants was obtained (FIGS. 11C-11D). The smooth surface was imperative for achieving reproducible tribological measurements.

Titanium Anodization

An electrochemical cell containing two-electrodes, i.e., platinum (cathode) and titanium (anode) was used. The electrolyte solution contained 1 M $(NH_4)_2SO_4$ and 0.5 wt % $NH_4F$. All electrolytes were prepared from reagent grade chemicals and deionized water. The electrochemical treatment was conducted with a DC power source operated at 2.5 V and 1.5 A, at room temperature for 2.5 h. After the electrochemical treatment, the samples were rinsed with deionized water and dried under nitrogen stream.

Figure 12A:
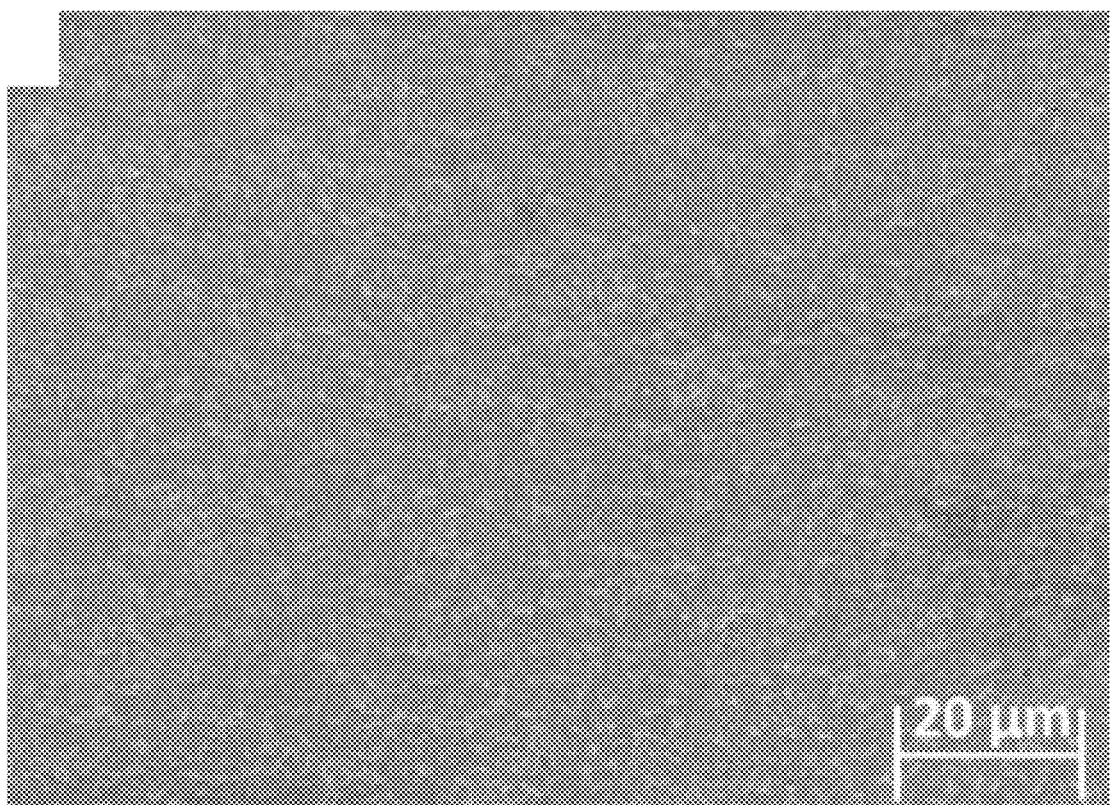
FIGS. 12A-12C SEM images of porous titanium after anodization in different magnifications, the average diameter of the pores (tubes) is 100 nm.
Figure 12B:
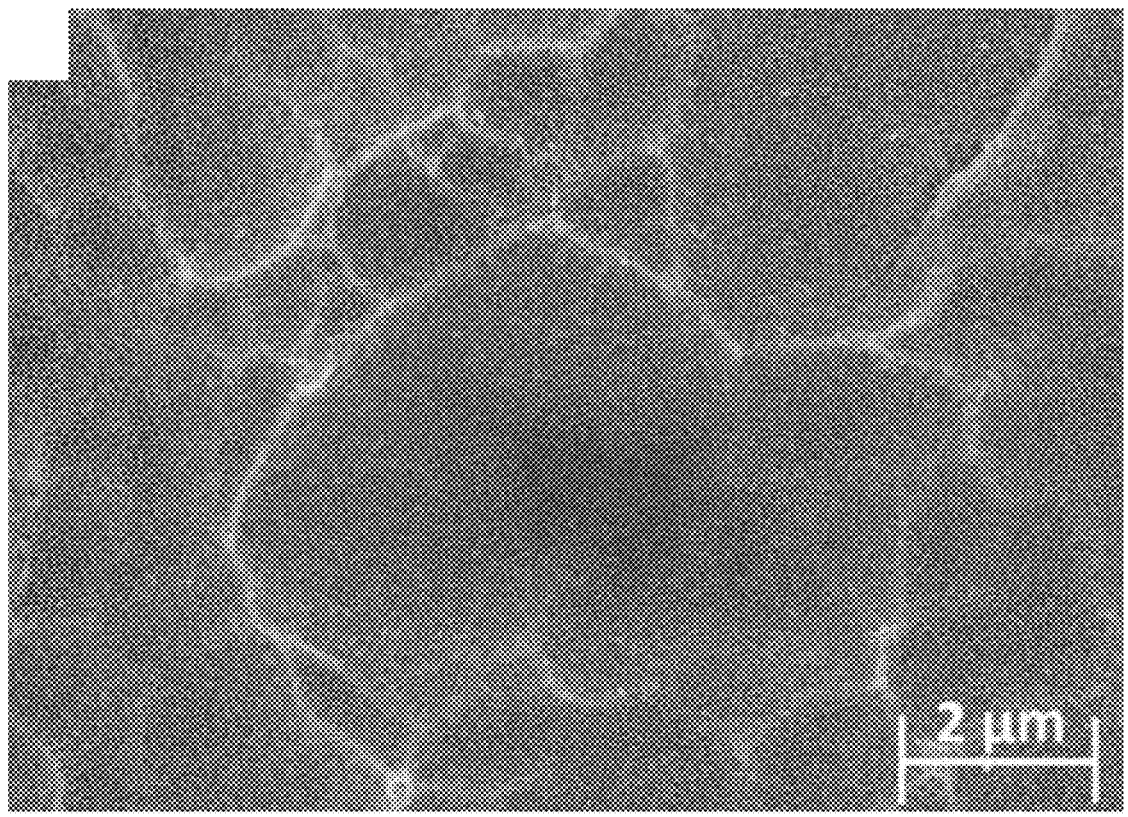
Figure 12C:
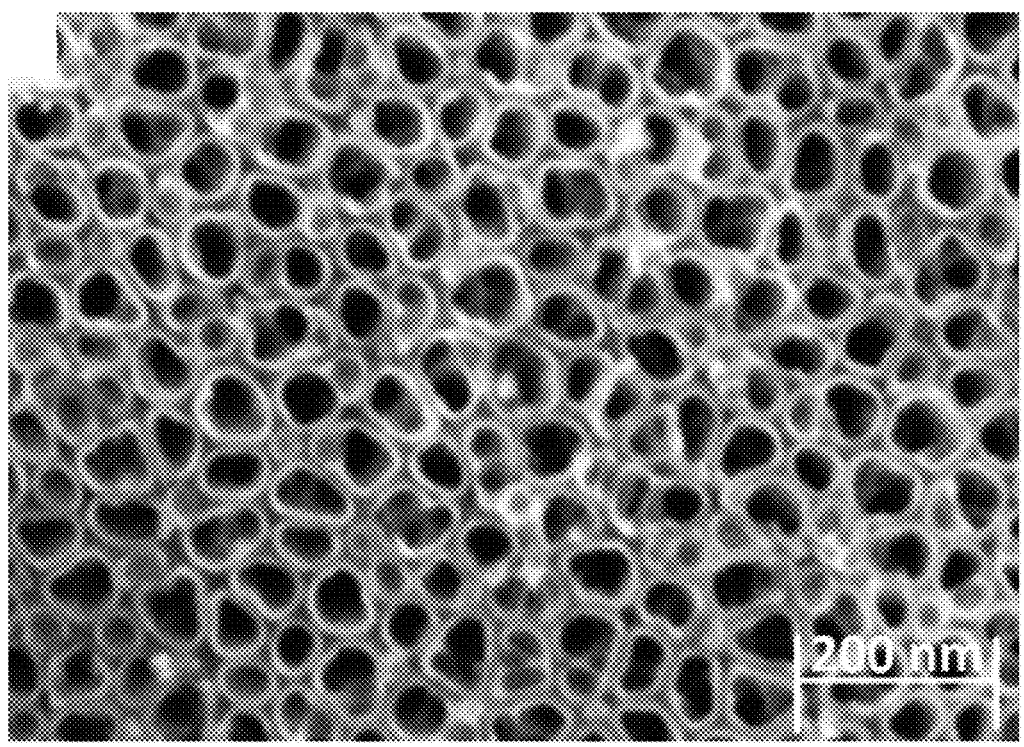

The surface of the titanium after anodization is displayed in FIGS. 12A-12C. Visibly the anodized titanium surface consists of a dense array of ($TiO_2$) nanotubes with the range of pore diameters between 50-130 nm, which form a highly organized, roughly hexagonal, pattern on the Ti surface.

Electrophoretic Deposition (EPD)

The detailed synthesis of the Re:IF-$MoS_2$ nanoparticles (Re content <0.1 at %), which were added to the coating processes, was reported before [Yadgarov, L.; et al. Investigation of Rhenium-Doped $MoS_2$ Nanoparticles with Fullerene-Like Structure. Z. Anorg. Allg. Chem. 2012, 638, 2610-2616]. Three different chemical baths were used for electrophoretic deposition of HA+IF NP on the porous titanium substrate. Titanium samples were used as the working electrode (cathode), while a platinum plate served as the anode. The final volume of all three electrolyte solutions containing 1 mg of the IF NP was 50 mL.

Solution A: The electrolyte solution consisted of 42 mM $Ca(NO_3)_2$ and 25 mM $NH_4H_2PO_4$, 1 mg Re:IF-$MoS_2$ sonicated in 3 mM cetyl trimethylammonium bromide (CTAB). Ethyl alcohol was added into the above solution in a 1:1 ratio in order to reduce the hydrogen evolution on the titanium electrode. The initial pH of the electrolyte solution was 4.5. The coating process was carried out at 40° C. with a DC power supply at 20 V bias and 0.11 A for 3 h. The samples were washed with deionized water and dried for 24 h at 100° C.

Solution B: The electrolyte solution consisted of 5.25 mM $Ca(NO_3)_2$, 10.5 mM $NH_4H_2PO_4$, and 150 mM NaCl. The initial pH of the solution was adjusted to 5.30 by adding NaOH. 1 mg Re:IF-$MoS_2$ was sonicated in distilled water for 15 min and added to the electrolyte solution. The coating process was conducted with a DC power source operated at 2.5 V and 0.11 A at room temperature for 3 h.

Solution C: The electrolyte solution consisted of 3 mM $Ca(NO_3)_2$ and 1.8 mM $KH_2PO_4$, 1 mg Re:IF-$MoS_2$ sonicated in 3 mM CTAB. The initial pH of the electrolyte solution was 5. The coating process was conducted with a DC power source operated at 6 V and 1 A at room temperature for 1 h. The resulting samples, after coating, were washed with deionized water and dried in room temperature.

The formal molar Ca/P ratio in HA is 5:3 (1.67). The Ca/P ratio in each coating was calculated based on semi-quantitative. Energy dispersive spectroscopy (EDS) analysis. For solution A, the ratio was found to be 2.6. The higher abundance of calcium in this coating could be attributed to the presence of portlandite ($Ca(OH)_2$). The Ca/P ratio of the coating obtained from solution B, which was highly crystalline and discontinuous was 1.5, which agrees well with the HA formula (1.66). The ratio is 1 for the coating obtained from solution C, which can be ascribed to the presence of calcium pyrophosphate phase ($Ca_2(P_2O_7)$) in the coating—see XRD analysis (Example 3).

The bath showing the most uniform coating and good adhesion (solution A) was then further studied by changing the deposition time to 2, 3 and 4 hours and subsequent annealing at 700° C. for 1 h.

Characterization

High-Resolution Scanning Electron Microscopy (HRSEM) and High-Resolution Transmission Electron Microcopy (HRTEM):

The surface morphology of the titanium samples was analyzed by (HRSEM) (Zeiss Ultra 55) after each step. For topographical information, the secondary electrons were recorded using the SE2 and In-lens detectors. For atomic number contrast the backscattering electron (BSE) detector was used. In order to avoid the sample charging during the analysis, the imaging was done under relatively low accelerating voltage (2-5 kV) and low current. Energy dispersive spectroscopy (EDS) analysis (EDS Bruker XFlash/60 mm) of the samples was undertaken as well. The reported results of the EDS were based on standard-less analysis and hence is semi-quantitative in nature.

TEM was performed with a JEOL 2100 microscope (JEOL Ltd., Tokyo, Japan) operating at 200 kV, equipped with a Thermo Fisher EDS analyzer. High-resolution TEM (HRTEM) images were recorded with a Tecnai F30 UT (FEI) microscope (FEI, Eindhoven, the Netherlands) operating a 300 kV. The TEM grids were prepared by dripping an ethanolic solution of the nanoparticles onto a collodion-coated Cu grids.

Figure 2A:
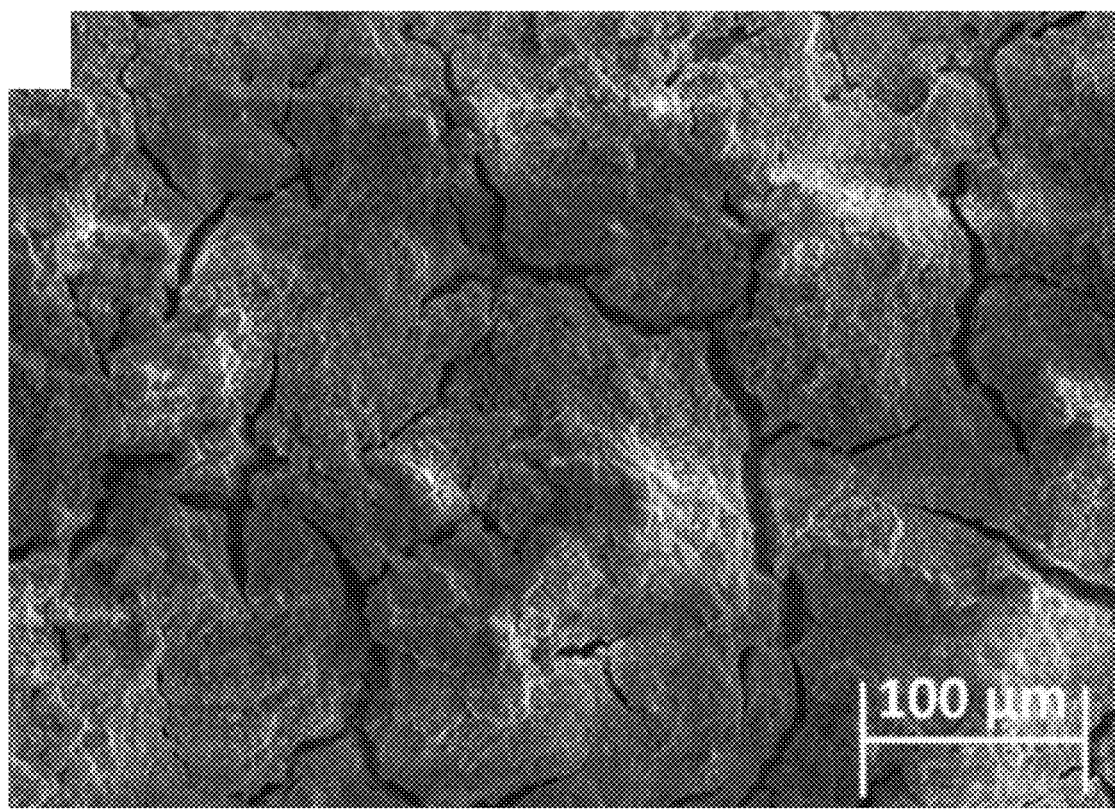
FIGS. 2A-2B present HRSEM pictures of HA with Re:IF-MoS$_2$ nanoparticles coating obtained from solution A on porous titanium substrate in two magnifications.
Figure 2B:
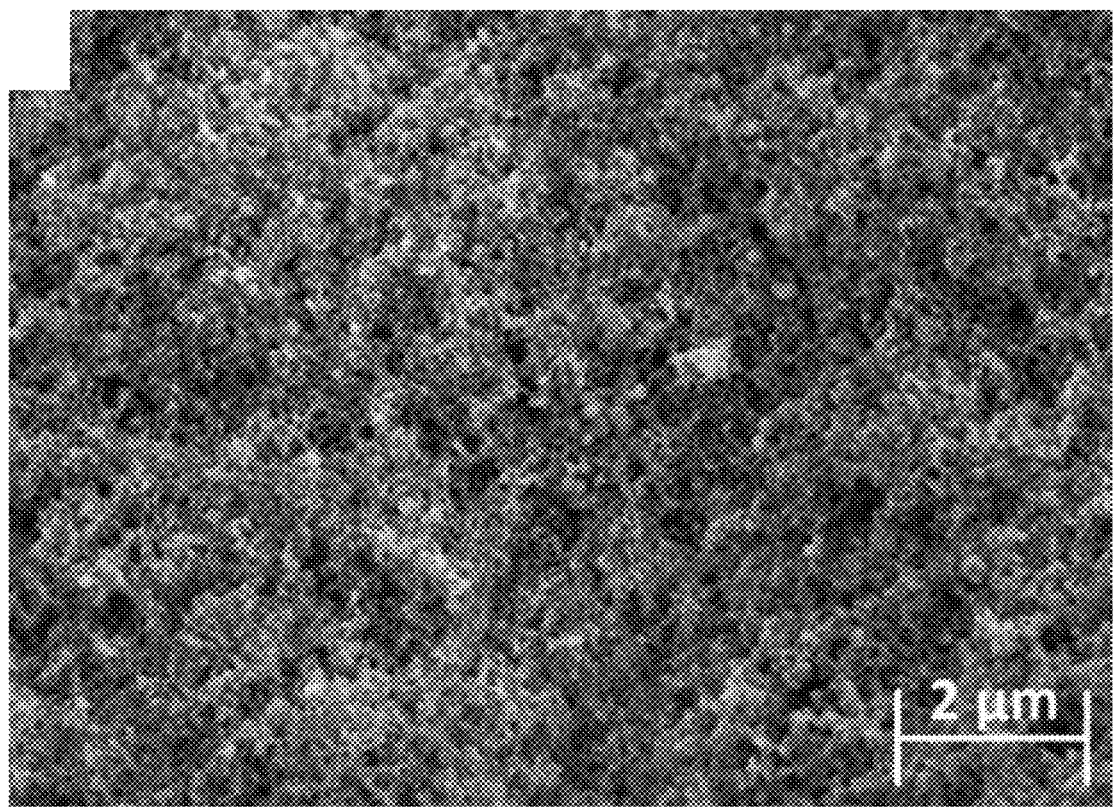

The surface morphology of the HA film prepared via solution A (FIGS. 2A-2B) and solution C was more homogeneous and could be successfully combined with the Re:IF-$MoS_2$ NP in the films as opposed to the film obtained from solution B, which was highly crystalline but non-uniform. The surface morphology of the film obtained from solutions B and C are shown in FIGS. 9A-9B and 10A-10B, respectively The SEM images of the surface of the HA films with Re:IF-$MoS_2$ nanoparticles obtained from solution A for different deposition periods are shown in FIGS. 3A-3D. The surface of the coated film shows defects, including the presence of cracks and pores with circular shape. Such pores can be probably attributed to the formation of $H_2(g)$ bubbles during the coating process.

Interestingly, the bias applied during EPD for solution B (and C) was appreciably smaller (2.5 V) compared to solution A (20 V). On the other hand, the film obtained by EPD from solution A was quasi-continuous. It was highly crystalline but less uniform in the case of solution B, i.e., the apparent current density was higher than that calculated on the basis of the formal electrode surface. The higher voltage used for the EPD from solution A implied a much higher rate of hydrogen production, which could explain the porous structure of this film. The density of the pores and their sizes could be possibly tuned by the bias applied on the cathode during the electrophoretic deposition. Furthermore, addition of surface active agents, like CTAB and others, could reduce the size of the pores.

Figure 3A:
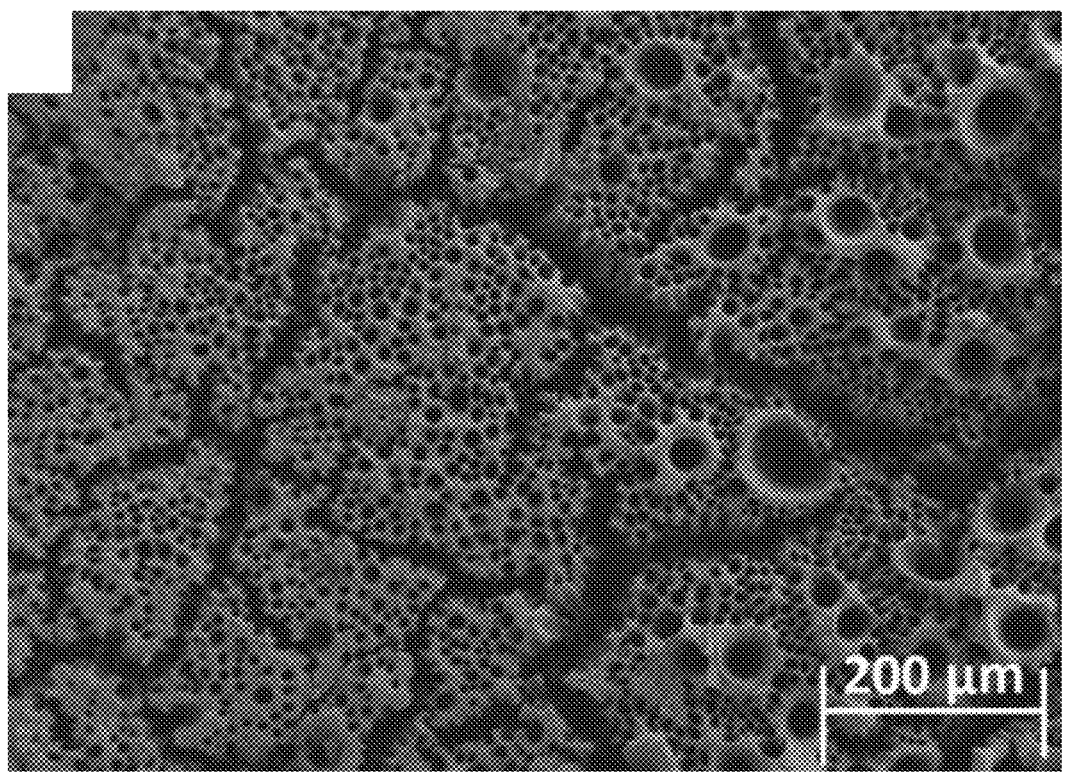
FIGS. 3A-3D present HRSEM images of the HA film with Re:IF-MoS$_2$ obtained from solution A after 2 hours (FIG. 3A), 3 hours (FIG. 3B), and 4 hours (FIG. 3C) deposition. The Re:IF-MoS$_2$ nanoparticles in the film (FIG. 3C) are observed in the backscattering electron (BSE) mode (FIG. 3D). The arrows in FIG. 3D point on the Re:IF-MoS$_2$ nanoparticles occluded in the HA film.
Figure 3B:
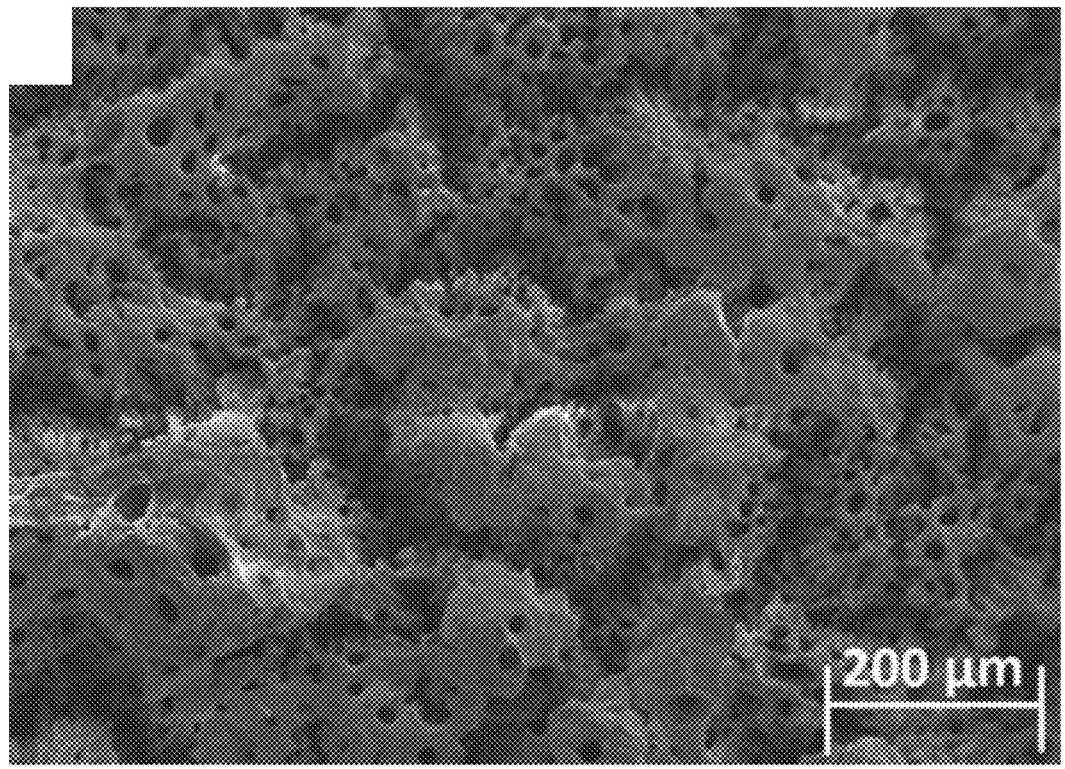
Figure 3C:
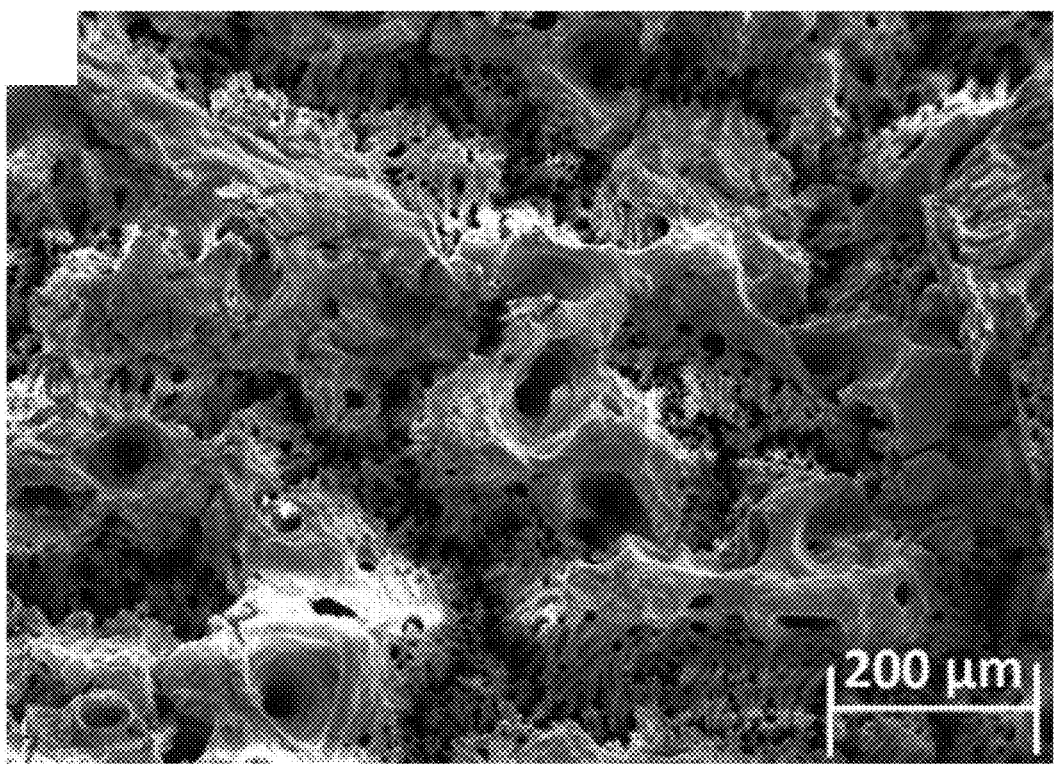
Figure 3D:
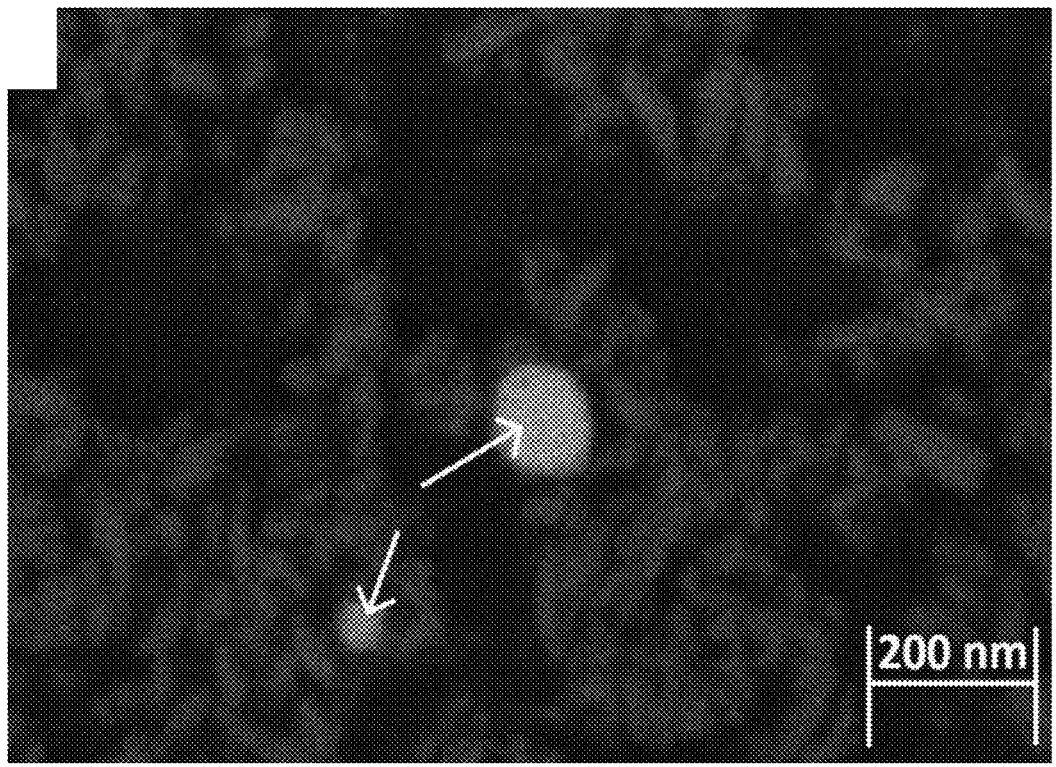

The large cracks are diminished, and the pore-size decreased as the coating time was prolonged. The thickness of the coating was a few microns, therefore the nanoparticles could have been buried under the film surface and even be closer to the titanium substrate. Using low energy beam (2 keV) in the BSE mode, the IF NP could be nevertheless observed (FIG. 3D).

Example 2

Figure 1C:
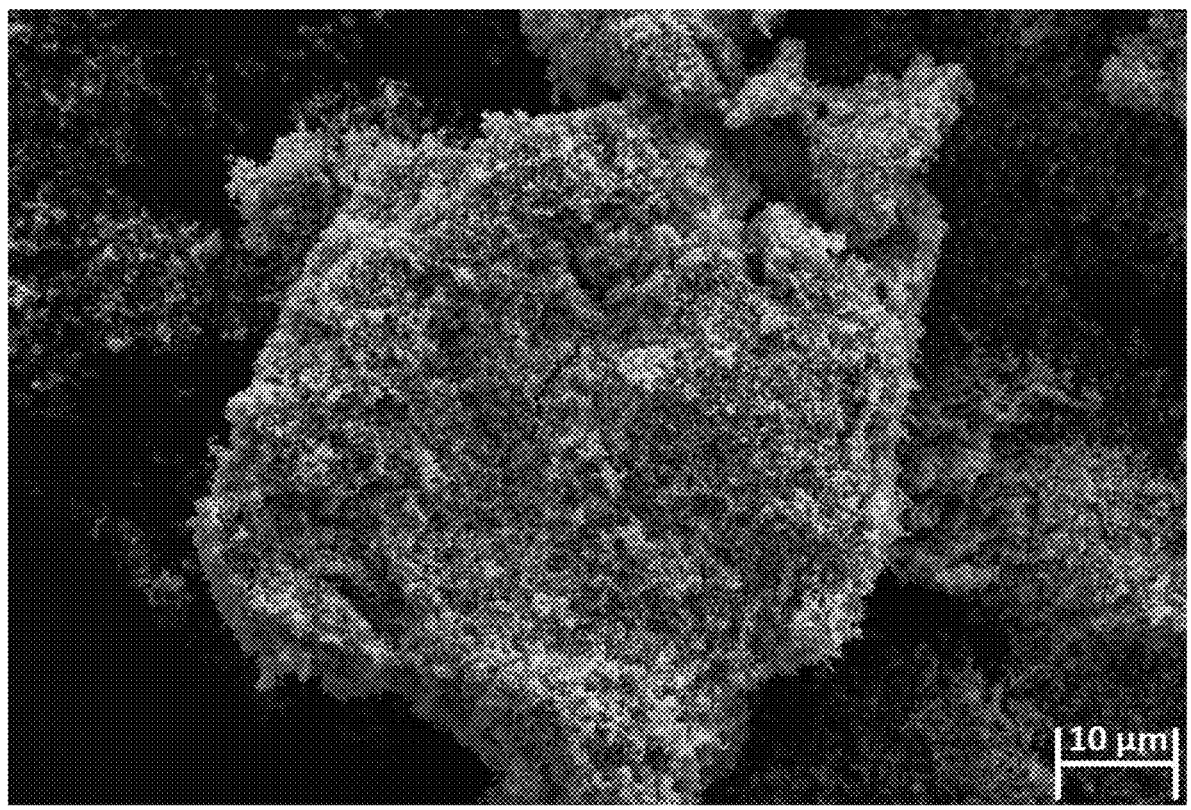

Zeta Potential Results of Hydroxyapatite (HA) and Rhenium Doped Fullerene Like $MoS_2$ (Re:IF-$MoS_2$) Film on Titanium Substrate The surface charge of the HA suspension with and without the nanoparticles was determined by zeta potential (ZP) measurements using ZetaSizer Nano ZS (Malvern Instruments Inc., Malvern, UK) with a He—Ne light source (632 nm). To prepare the samples for these measurements, IF (0.6 mg) NP were deagglomerated in 20 mL purified water by sonicating for 5-10 minutes using an ultrasonic bath (see FIG. 1C for a SEM image of such an agglomerate). Subsequently, 0.2 mL of the IF suspension was added to 1.5 mL aqueous solutions with pH varying from 1 to 12 and sonicated for an extra 5 min. Before the addition of the IF NP, the pH of each solution was adjusted using concentrated NaOH or HCl. The final concentration of the IF NP was 0.004 mg/mL. The ZP of the solutions was measured in a folded capillary cell (DTS1060) made from polycarbonate with gold plated beryllium/copper electrodes.

Figure 4A:
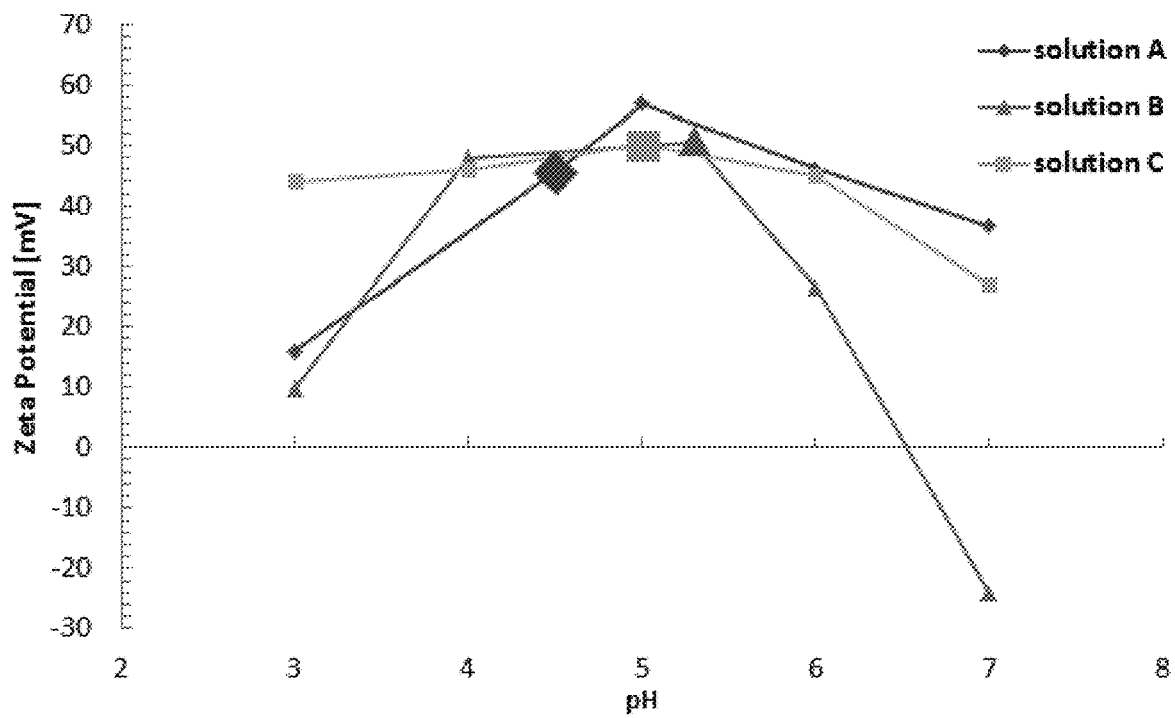
FIGS. 4A-4B present zeta-potential vs. pH for Re:IF-MoS$_2$ nanoparticles.
Figure 4B:
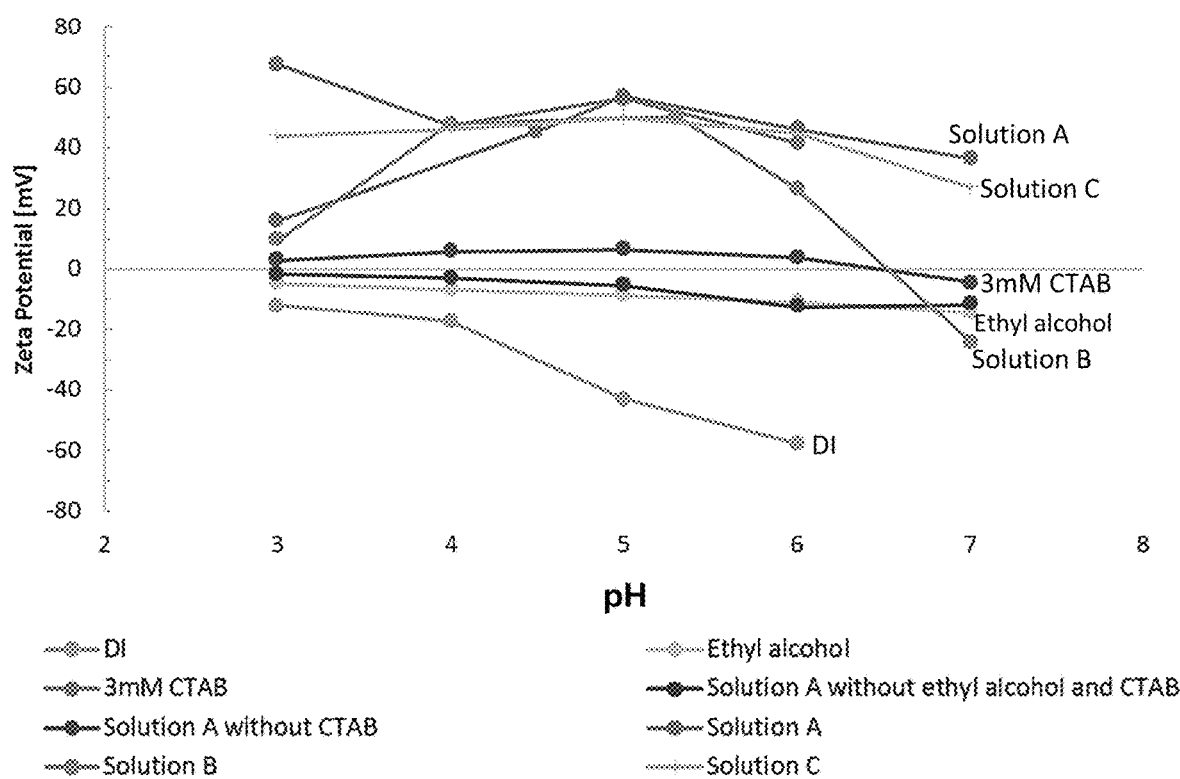

FIGS. 4A-4B show the results of the Zeta potential (ZP) measurements performed with the three solutions containing Re:IF-$MoS_2$ nanoparticles as a function of pH—up to pH=7. The ZP of all the solutions containing the nanoparticles was positive for pH below 6.5. At higher pH the ZP of solution B became negative, while that of solutions A and C remain positive. This difference can be attributed to the addition of the CTAB, which is a cationic surfactant, to solutions A and C. The (positive) ZP of the natural solutions used for EPD is marked on FIG. 4A for all three solutions.

The ZP measurements showed that the species in the HA solution containing the IF NP were positively charged and consequently, the HA film could be deposited on the negative electrode (Ti) during the EPD process. The ZP of the IF NP in pure water, ethanol solution, CTAB in water, and the three solutions used for the EPD (included also in FIG. 4A) are summarized in FIG. 4B, the errors of the ZP measurements were about 2%.

Example 3

X-Ray Diffraction (XRD) of Hydroxyapatite (HA) and Rhenium Doped Fullerene Like $MoS_2$ (Re:IF-$MoS_2$) Film The film was removed from the Ti substrate and carefully crushed into a powder. The powder was analyzed by X-ray powder diffraction (XRD) using TTRAX III (Rigaku, Tokyo, Japan) theta-theta diffractometer equipped with a rotating copper anode X-ray tube operating at 50 kV/200 mA. A scintillation detector aligned at the diffracted beam was used after a bent Graphite monochromator. The samples were scanned in specular diffraction mode ($\theta/2\theta$ scans) from 10 to 80 degrees ($2\theta$) with step size of 0.025 degrees and scan rate of 0.5 degree per minute. Phase identification and quantitative analysis were performed using the Jade 2010 software (MDI) and PDF-4+ (2016) database.

Figure 5A:
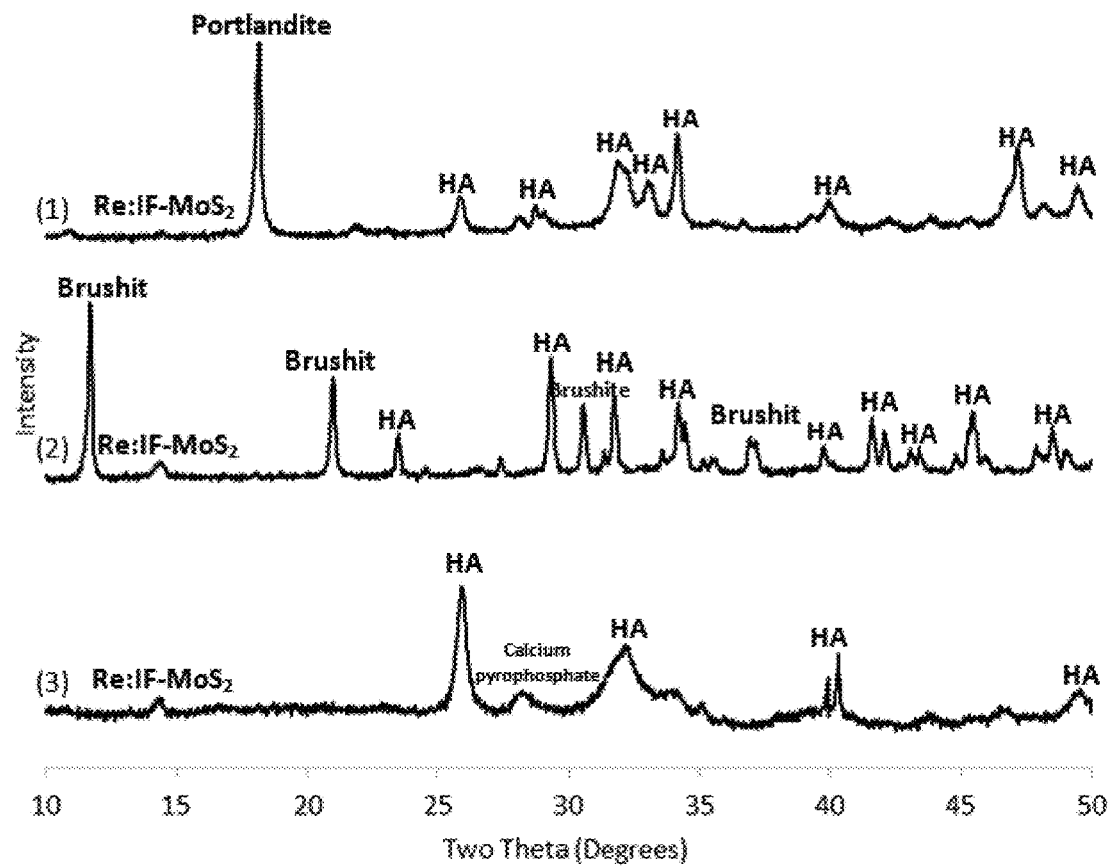
FIGS. 5A-5B present XRD patterns of the HA films incorporating Re:IF-MoS$_2$ nanoparticles.
Figure 5B:
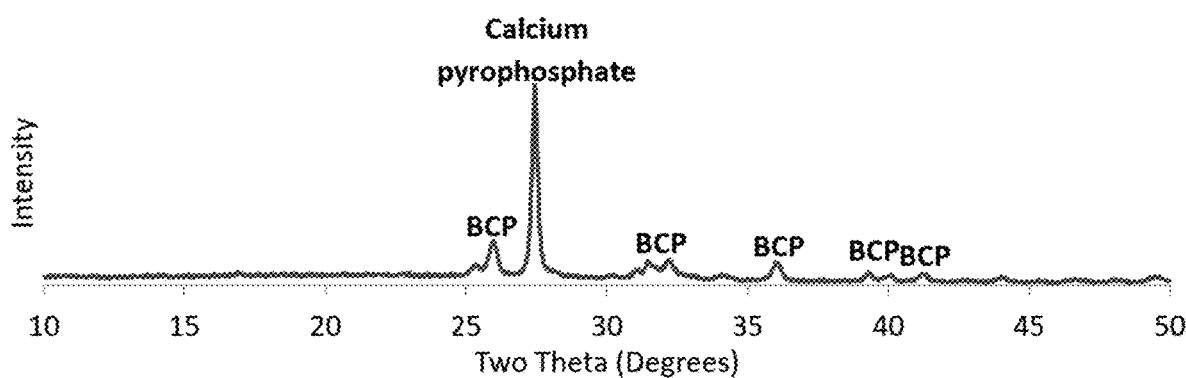

The results of the XRD analyses are summarized in FIGS. 5A-5B and in Table 1. The XRD patterns of the different coatings obtained from solutions A, B and C are shown in FIG. 5A. The major phase obtained by EPD of these solutions is HA. Nonetheless, the coating obtained from solution A contained appreciable amounts (25 wt %) of portlandite ($Ca(OH)_2$). Solution B, on the other hand, contained, in addition to the HA, also significant amounts of brushite-($CaHPO_4 \cdot 2H_2O$). The film obtained from solution C contained calcium pyrophosphate-($Ca_2(P_2O_7)$). The presence of the Re:IF-$MoS_2$ nanoparticles in the coatings is confirmed by the tiny peak at 14.3°. The content of the IF NP is calculated as 0.2 wt % for solution A, 1.5 wt % for solution B and 1.4 wt % for solution C. This amount is rather small but could nevertheless lead to major improvements of the tribological properties of the film without compromising its mechanical robustness.

Following the annealing of the film obtained from solution A (FIG. 5B), the HA became biphasic calcium phosphate (BCP), i.e., intimate mixture of two phases: HA (73.6 wt %) and $\beta$-TCP (5.9 wt %), and 0.1 wt % Re:IF-$MoS_2$ NP.

TABLE 1

Composition of the films deposited from different solutions determined from the XRD analysis.

| EPD films | HA | Portlandite | Brushite | Calcium Pyrophosphate | $\beta$-TCP | Re:IF-MoS2 |
|---|---|---|---|---|---|---|
| Film obtained from solution A | 74.8 wt % | 25 wt % | | | | 0.2 wt % |
| Film obtained from solution B | 17.2 wt % | | 81.3 wt % | | | 1.5 wt % |
| Film obtained from solution C | 81.1 wt % | | | 17.5 wt % | | 1.4 wt % |
| Film obtained from solution A after annealing | 73.6 wt % | | | 20.4 wt % | 5.9 wt % | 0.1 wt % |

Figure 6:
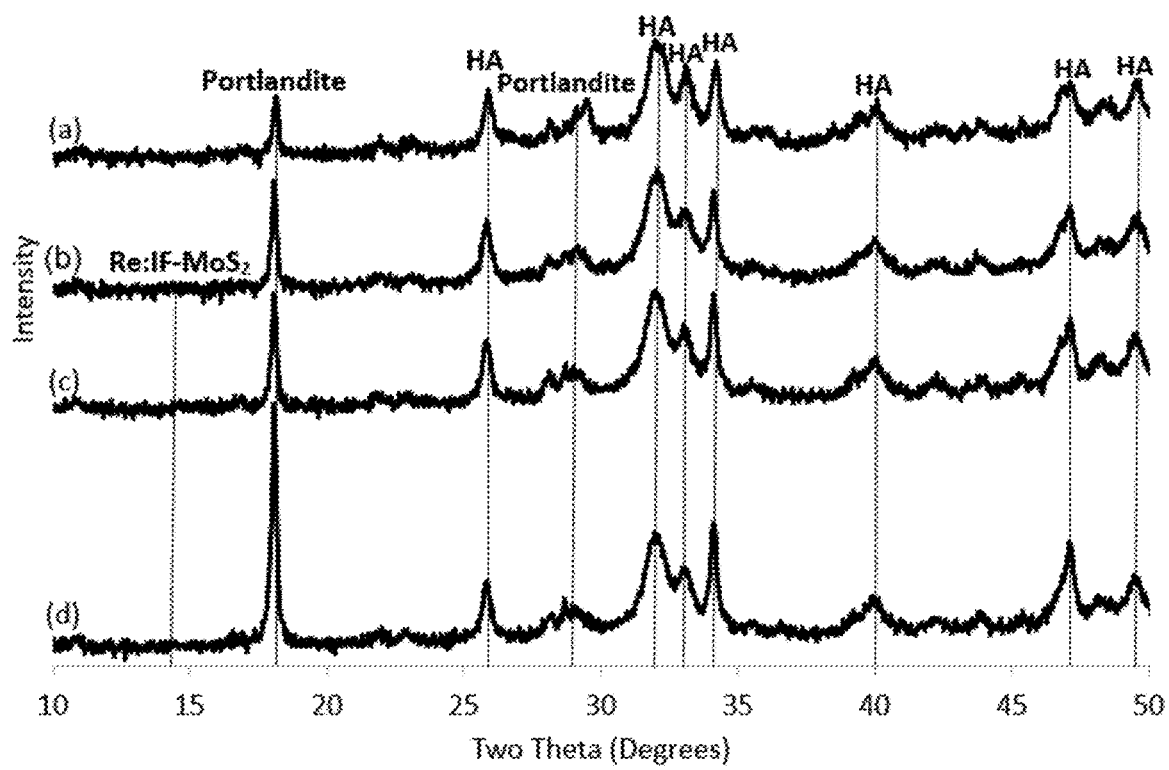
FIG. 6 presents XRD patterns of films obtained from solution A without the Re:IF-MoS$_2$ NP (a) and (with the IF NP) for different deposition periods: after 2 hours (b), 3 hours (c) and 4 hours (d).
Figure 7:
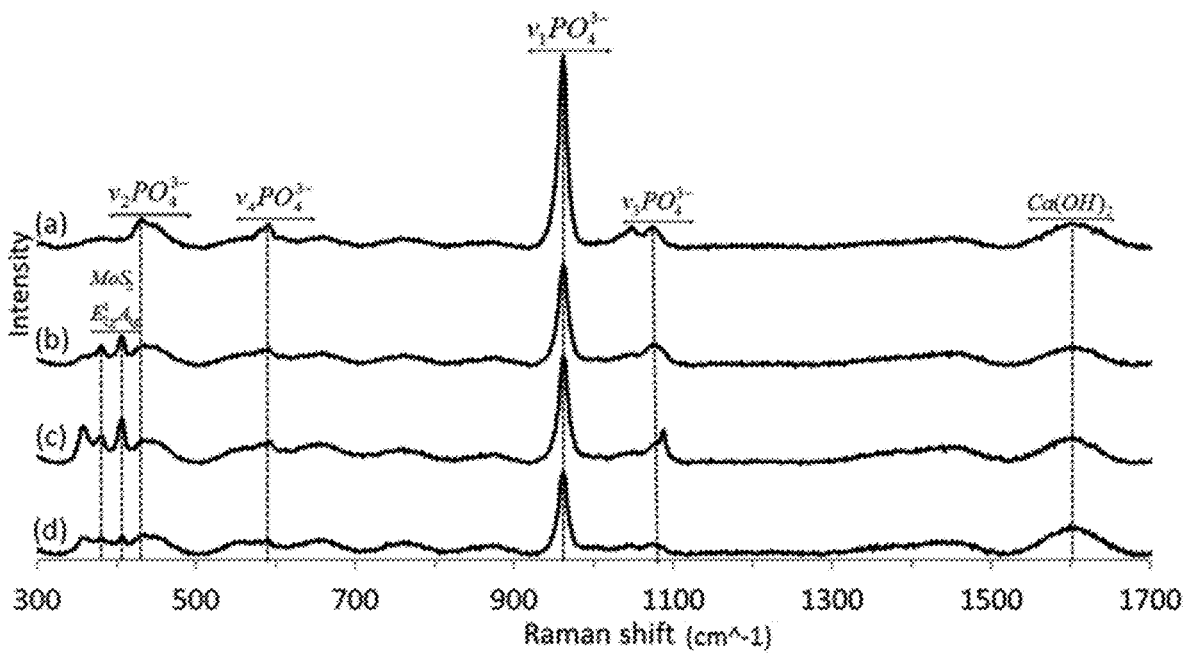
FIG. 7 presents Raman spectra of HA powder film without (a) and with the Re:IF-MoS$_2$ nanoparticles obtained from solution A for different EPD periods: after 2 hours (b), 3 hours (c) and 4 hours (d).
Figure 8A:
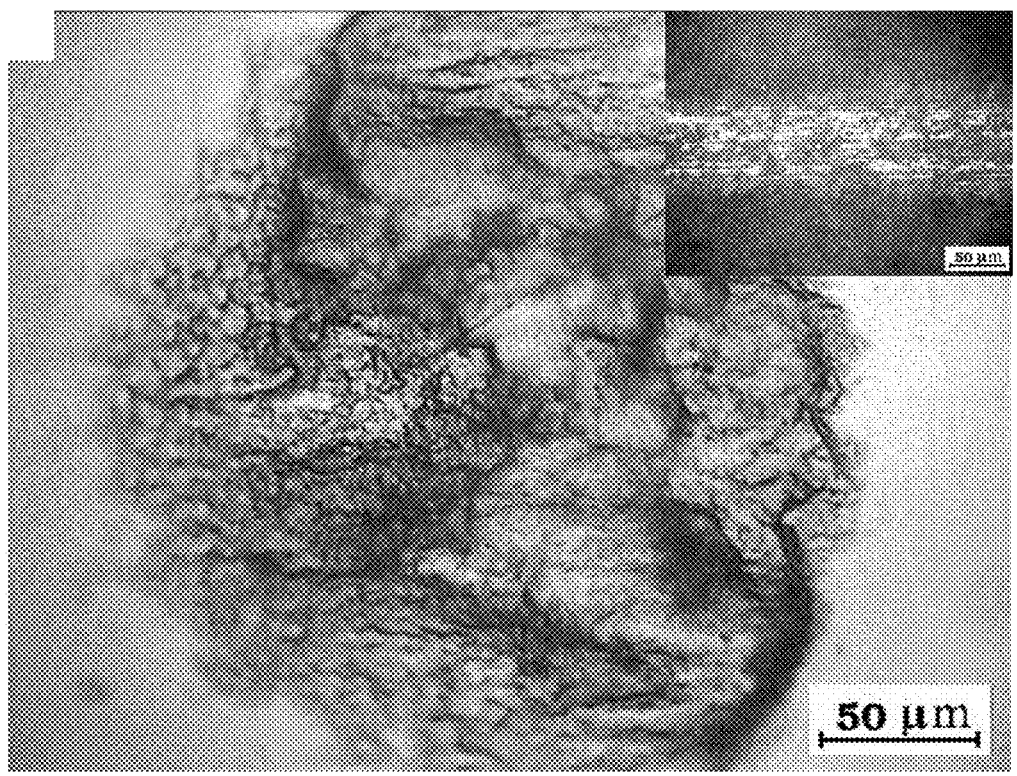
FIGS. 8A-8D present optical images of wear on the ball and inside the track of HA film without (FIG. 8A) and with the Re:IF-MoS$_2$ nanoparticles obtained from solution A for different periods: after 2 hours (FIG. 8B), 3 hours (FIG. 8C) and 4 hours (FIG. 8D) on anodized titanium.
Figure 8B:
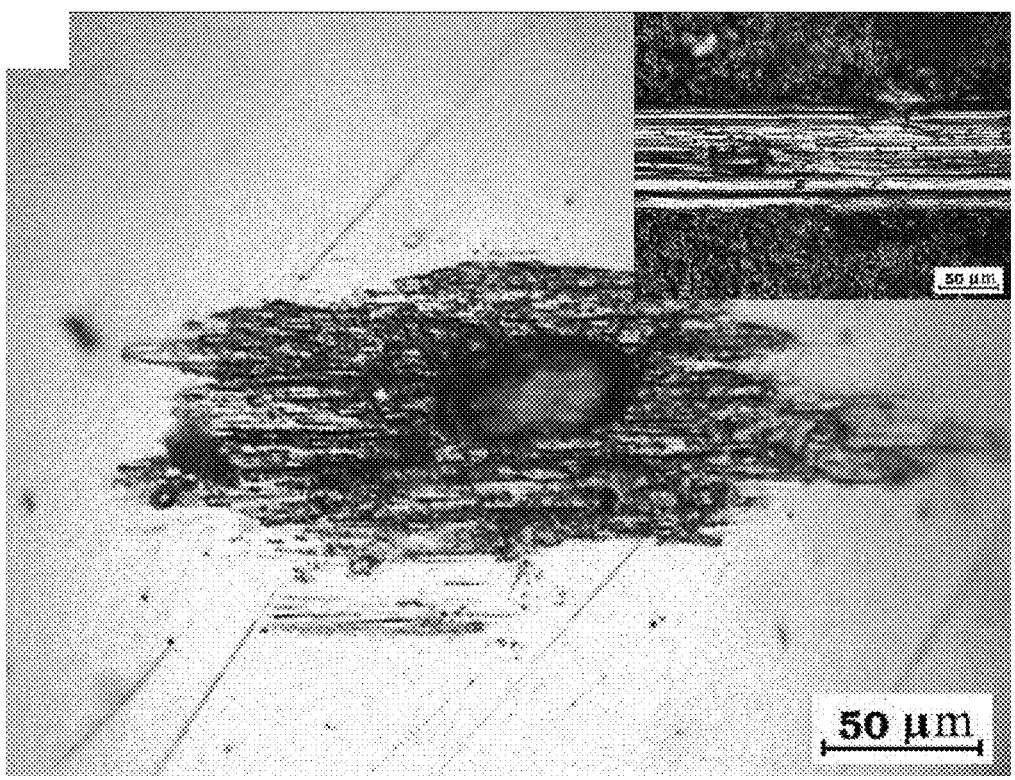
Figure 8C:
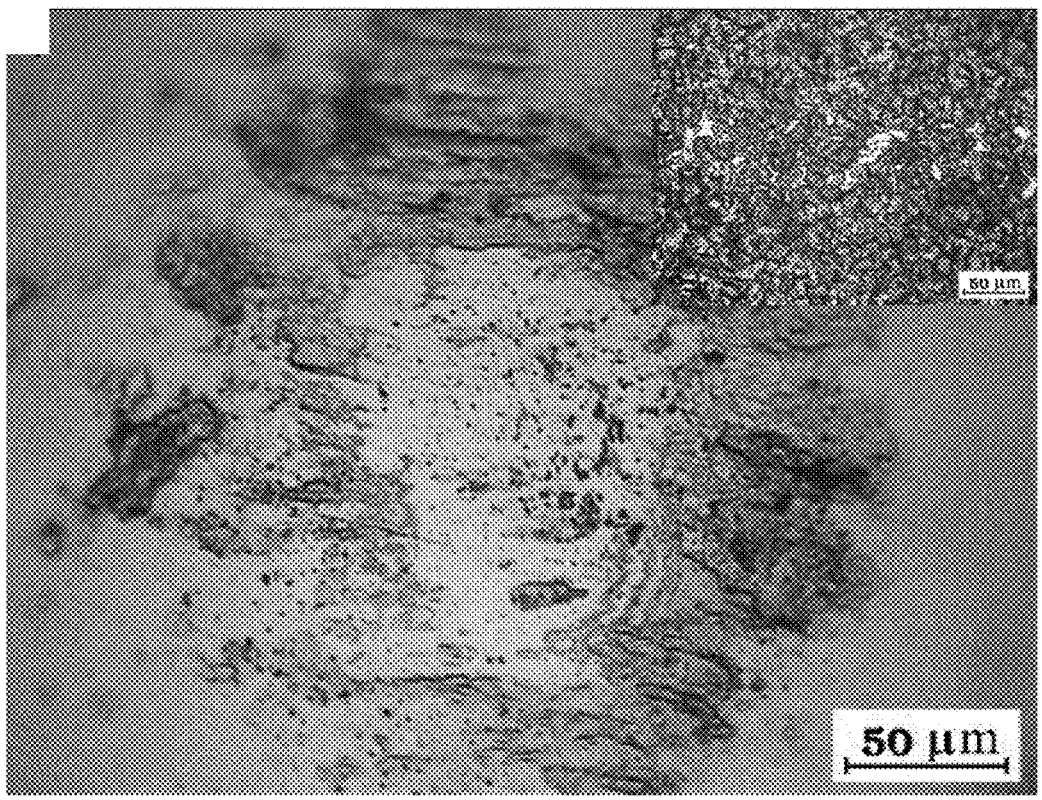
Figure 8D:
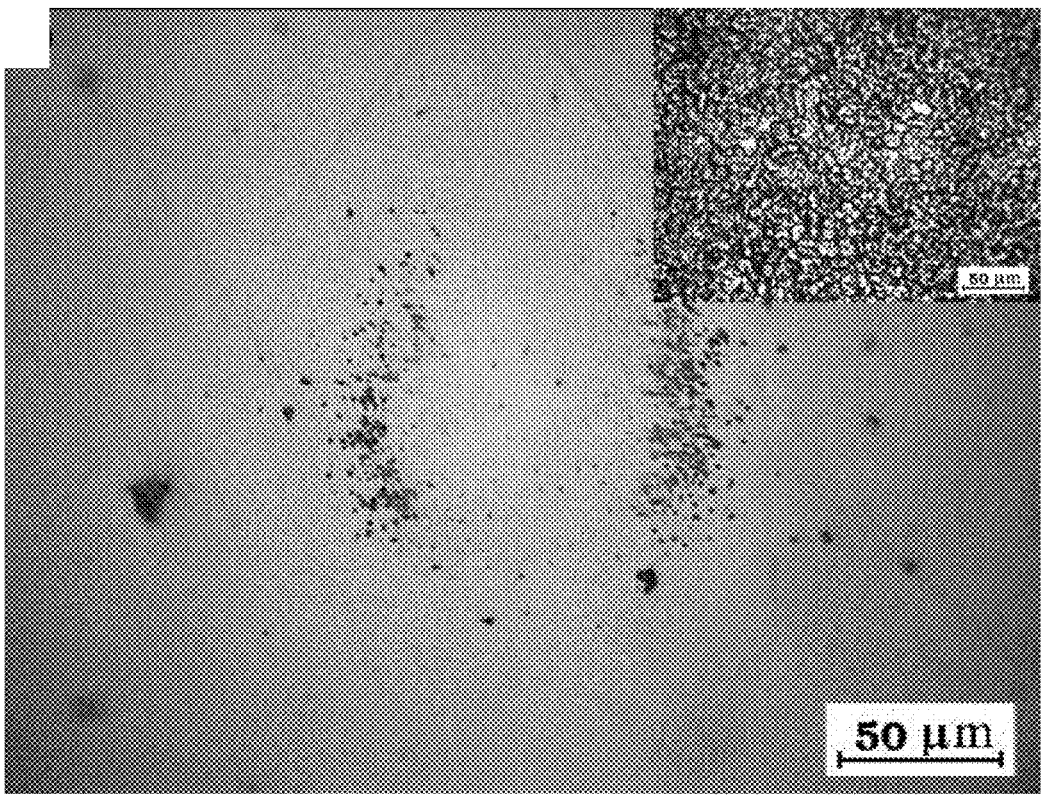
Figure 9A:
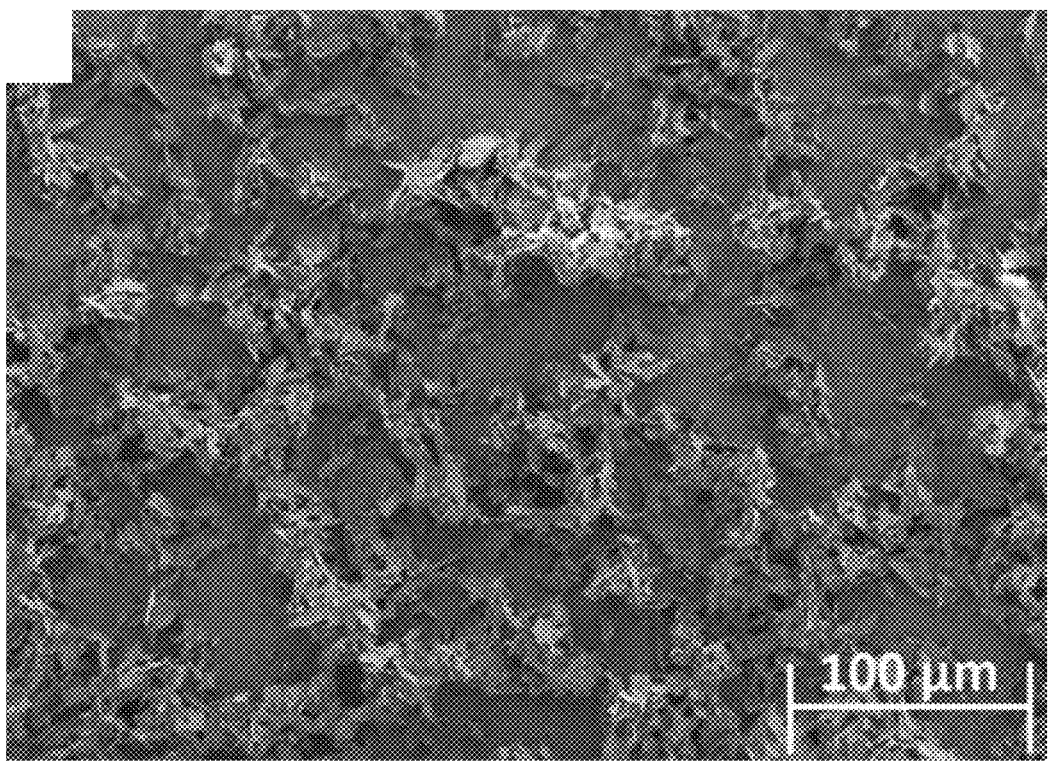
FIGS. 9A-9B present SEM images of HA with Re:IF-MoS$_2$ nanoparticles coating obtained from solution B (3 h deposition time) on porous titanium substrate in different magnifications.
Figure 9B:
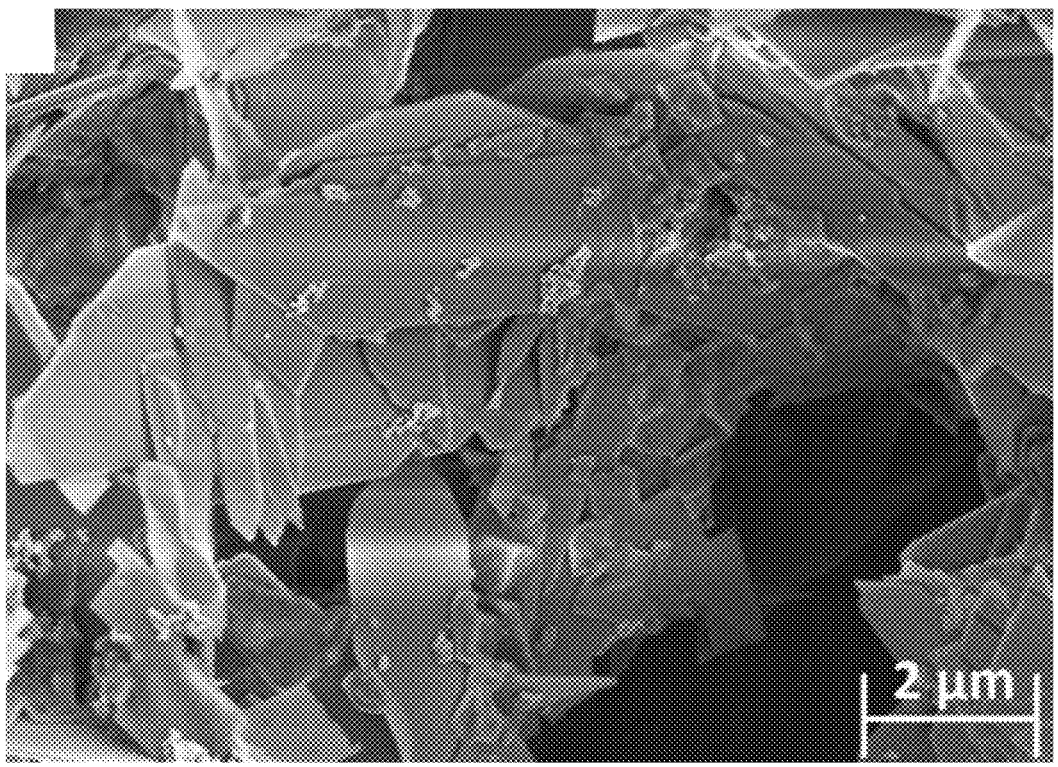
Figure 10A:
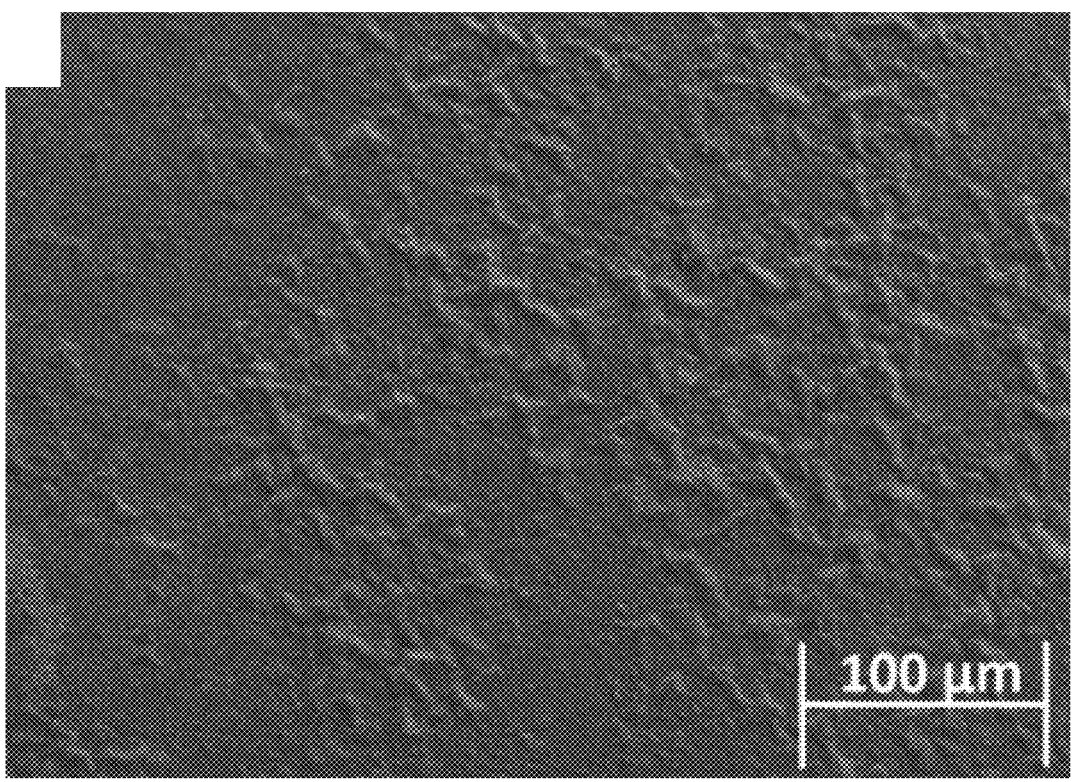
FIGS. 10A-10B present SEM pictures of HA with Re:IF-MoS$_2$ nanoparticles coating obtained from solution C (1 h deposition time) on porous titanium substrate in different magnifications FIGS. 11A-11D SEM images of titanium surface (a,b) before and (c,d) after surface treatment in different magnifications.
Figure 10B:
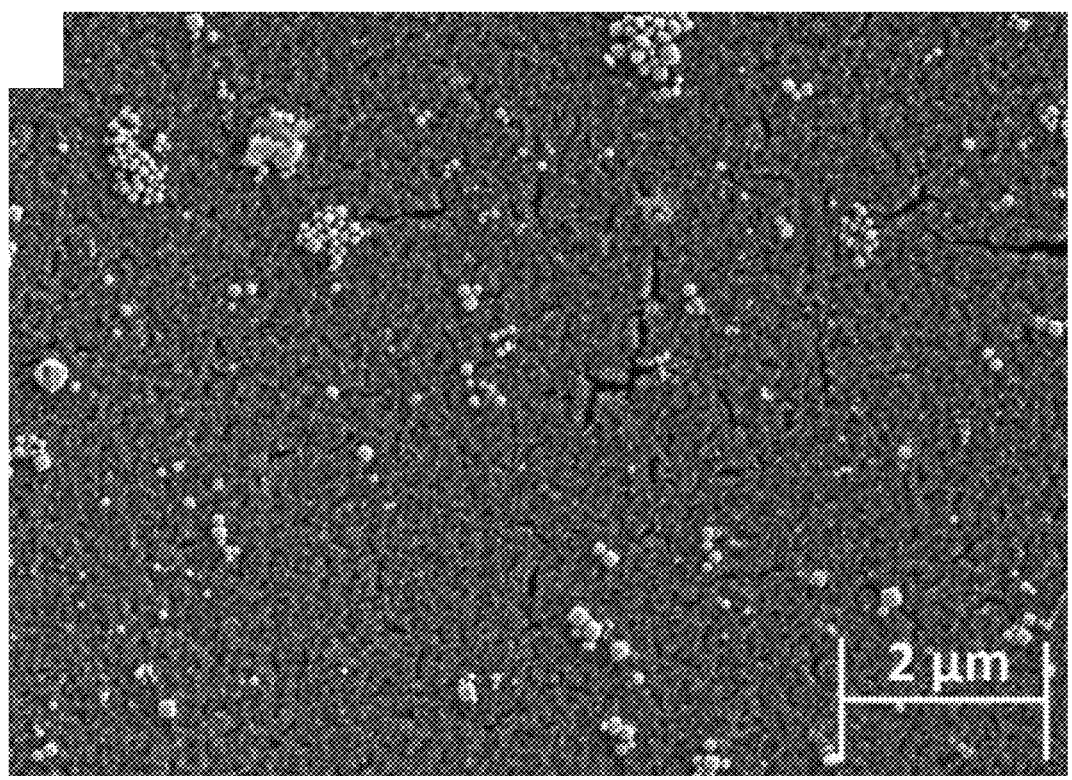

The XRD patterns of the films obtained from solution A without the NP (a) and with the IF NP for different deposition times (b-c) is shown in FIG. 6. The percentages of the compounds in each film is presented in Table 2. The major phase in the films was hydroxyapatite. The relative amount of the portlandite in the film increased with extending deposition times (FIG. 6). The relative amount of the calcium oxide didn't vary with the deposition time which was also true for the relative content of the IF NP. Although the signal of the IF NP was non-visible in FIG. 6, their presence is confirmed through both electron microscopy (FIGS. 3A-3D) and the Raman measurements (FIG. 7).

TABLE 2

Composition of the film determined via XRD analysis for different deposition times (from solution A).

| EPD films | HA | Portlandite | Calcium Oxide | Re:IF-$MoS_2$ |
|---|---|---|---|---|
| Film obtained from solution A without Re:IF-$MoS_2$ (3 h) | 87.8 wt % | 4.6 wt % | 7.6 wt % | |
| Film obtained from solution A (2 h) | 82.6 wt % | 7.4 wt % | 9.1 wt % | 0.3 wt % |
| Film obtained from solution A (3 h) | 80.4 wt % | 11.3 wt % | 8.0 wt % | 0.3 wt % |
| Film obtained from solution A (4 h) | 77.8 wt % | 13.6 wt % | 8.3 wt % | 0.3 wt % |

Example 4

Raman Spectroscopy of Hydroxyapatite (HA) and Rhenium Doped Fullerene Like $MoS_2$ (Re:IF-$MoS_2$) Film Raman spectra of the powders ground from the films were obtained with Horiba-Jobin Yivon (Lille, France) LabRAM HR Evolution set-up using solid state laser with a wavelength of 532 nm. The instrument was equipped with Olympus objectives MPlan N 100×NA 0.9. The measurements were conducted using a 600 grooves/mm grating. Each spectrum was acquired for 20 s and the spectra were averaged 100 times, which enabled using low excitation power thereby preserving the sample integrity. The spectral ranges collected were from 100 to 1800 $cm^{-1}$.

The Raman spectra of HA+IF films prepared from solution A for different deposition times (2, 3 and 4 hours) are shown in FIG. 7. The spectra showed the characteristic vibration bands of calcium hydroxide (wide peak at 1600 cm$^{-1}$) and poorly crystalline phosphoric moieties, especially phosphate $PO_4^{-3}$ bands at 469 ($v_2$), 562-603 ($v_4$), 962 ($v_1$) and 1000-1104 cm$^{-1}$ ($v_3$). These bands are typical of HA. The Raman spectra showed also the typical $MoS_2$ modes at 383 ($E_{2g}$) and 408 cm$^{-1}$ ($A_{1g}$). Interestingly, in contrast to the XRD pattern (FIG. 6), the Raman bands of the IF NP in the HA film are easily discerned here.

Example 5

Tribological Results of Hydroxyapatite (HA) and Rhenium Doped Fullerene Like $MoS_2$ (Re:IF-$MoS_2$) Film A home-made ball-on-flat rig was used for the tribological tests. The tests were carried-out at room temperature and humidity of ~40%. Each test was repeated 5-times. Tribological tests were performed on the titanium samples at every step of the experimental procedure. The tribological testing was done under dry friction conditions. This testing method utilizes flat lower samples and a ball-shaped upper specimen, which slides against the flat specimen. The two surfaces move relative to each other in a linear, back and forth sliding motion, under a prescribed set of conditions. In this testing method, the load is applied vertically downwards through the ball against the horizontally mounted flat specimen. Two measurements procedures were used in these series of tests. Sliding speed of 0.3 mm/s was common to both series. In one series of measurements the load was 10 g; the diameter of the ball (hard steel—AISI 301) was 10 mm and consequently a Hertzian pressure of 150 MPa was applied on the film (20 cycles). In another series, the load was 20 g, the diameter of the ball 2 mm, i.e., a Hertzian pressure of 600 MPa was applied, and the number of cycles was 100.

Table 3 summarizes the data for the friction coefficient and surface roughness of the different samples under dry conditions. In general, the friction coefficient was found to go down along with the stages of the experimental procedure of preparing the film. The low friction coefficient of the HA film obtained from solution A can be attributed to the IF nanoparticle structure. The nanoparticles exhibited facile rolling when released from the film surface. In addition, gradual peeling/crushing of the NP and material transfer from the film surface to the counter surface of the ball contributed to the facile shearing of the mating surfaces and low friction coefficients. Interestingly, the friction coefficient of the HA film obtained from solution A was maintained also after 700° C. annealing.

TABLE 3

Summary of the initial and final friction coefficients and the initial roughness for different stages of preparation of the composite HA + IF film. Measurement conditions: diameter of the test ball 10 mm; load = 10 g (Hertzian pressure—P = 150 MPa).

| Tested film | Initial Coefficient of Friction | Final Coefficient of Friction (after 20 Cycles) | Initial Roughness (μm) |
|---|---|---|---|
| Titanium after surface treatment | 0.50 ± 0.01 | 0.60 ± 0.02 | 0.23 ± 0.03 |
| Titanium after anodization | 0.15 ± 0.01 | 0.23 ± 0.03 | 0.50 ± 0.05 |
| Film of HA with Re:IF-$MoS_2$ NP obtained from solution A on anodized titanium | 0.11 ± 0.01 | 0.13 ± 0.01 | 0.45 ± 0.4 |
| Film of HA with Re:IF-$MoS_2$ NP obtained from solution B on anodized titanium | 0.21 ± 0.02 | 0.43 ± 0.08 | 0.37 ± 0.03 |
| Film of HA with Re:IF-$MoS_2$ NP obtained from solution C on anodized titanium | 0.37 ± 0.23 | 0.30 ± 0.18 | 0.57 ± 0.02 |
| Film of HA with Re:IF-$MoS_2$ NP obtained from solution A on anodized titanium after annealing | 0.12 ± 0.01 | 0.11 ± 0.02 | 0.49 ± 0.7 |

Table 4 shows the dry friction coefficient of the coatings obtained from solutions A without (3 h) and with the NP after 2, 3 and 4 h of deposition time on the anodized titanium substrate. A higher Hertzian pressure (600 MPa) was used for the tribological test. The dry friction coefficient was reduced with increasing coating-time of the film.

Following the 4 h deposition time the friction coefficient was very low (0.12) attesting to the quality of the composite film.

TABLE 4

The initial and final friction coefficients and the initial roughness of the coating on titanium substrate obtained from solution A for different periods of deposition. Measurement conditions: diameter of the test ball 2 mm; load 20 g and Hertzian pressure of P = 600 MPa.

| Tested film | Initial Coefficient of Friction | Final Coefficient of Friction (after 100 Cycles) | Initial Roughness (μm) |
|---|---|---|---|
| Pure HA film obtained from solution A without NP after 3 h deposition | 0.66 ± 0.08 | 0.78 ± 0.04 | 1.59 ± 0.28 |
| HA film with Re:IF-$MoS_2$ NP obtained from solution A after 2 h | 0.75 ± 0.05 | 0.63 ± 0.03 | 0.49 ± 0.05 |
| HA film with Re:IF-$MoS_2$ NP obtained from solution A after 3 h | 0.53 ± 0.03 | 0.55 ± 0.04 | 0.57 ± 0.17 |
| HA film with Re:IF-$MoS_2$ NP obtained from solution A after 4 h | 0.13 ± 0.01 | 0.12 ± 0.02 | 0.48 ± 0.02 |

Therefore, it is clear that the extended deposition of the composite film resulted in lower friction under very high load. However, the mechanical stability of the film might have been partially compromised. The surface roughness of the films was in the sub-micron range for all the films containing the NP.

FIGS. 8A-8D show optical micrographs of the wear of the ball and the wear track on the film (inset) after different periods of EPD (600 MPa) and 100 cycles. In analogy to the friction coefficient, the visible wear scar on the ball and the wear track on the film were markedly reduced with the deposition time of the HA+IF NP film.

Example 6

Methods for Film Formation

Sol-Gel Deposition:

A solution of 3M $(C_2H_5O)_3PO$ was hydrolyzed for 24 h in a sealed container under vigorous stirring, 3 M $Ca(NO_3)_2 \cdot 4H_2O$ was added dropwise with 1 mgr Re:IF-$MoS_2$ nanoparticles in anhydrous ethanol. The mixed sol solution agitated for additional 30 min and kept static at ambient duration time for 24 h. $Ti_6Al_4V$ substrate was dip coated in the sol solution, then dried at 80° C. and followed by annealing in vacuum at 900° C. for 5 h.

Dip Coating:

3 mM $Ca(NO_3)_2$, 1.8 mM $KH_2PO_4$ were dissolved in distilled water, then adding 1 mgr Re:IF-$MoS_2$ nanoparticles after dispersion. Immersing titanium substrate in the solution at 37° C. and sealed the container for 24 h, finally the substrate was drying at room temperature, followed by annealing at 700° C. for 3 h.

Casting Molding

PLLA was dissolved in dichloromethane and adding hydroxyapatite powder with Re:IF-$MoS_2$ nanoparticles to the polymer solution, split the solution to Teflon mold and drying at room temperature.

Example 7

Film Formation Including PLLA, HA and INT-$WS_2$

Materials

Poly L-lactic acid (PLLA) with an inherent viscosity midpoint of 2.4 dl/g was purchased from Corbion (Gorinchem, The Netherlands). Oleic acid (OA, ≥99%) and Hydroxyapatite (HA, nanopowder, <200 nm particle size (BET), ≥97%, synthetic) were purchased from Sigma Aldrich Chemical Company.

INT-$WS_2$ with diameter between 30-150 nm and length between 1-20 micrometer were synthesized using a published procedure [Chithaiah, P.; Ghosh, S.; Idelevich, A.; Rovinsky, L.; Livneh, T.; Zak, A. Solving the "$MoS_2$ nanotubes" synthetic enigma and elucidating the route for their catalyst-free and scalable production. ACS Nano 2020, 14, 3004-3016]. Briefly, the precursor nanoparticles of tungsten trioxide, grew into high aspect ratio tungsten suboxide nanowhiskers under mild reducing atmosphere at 840° C. Subsequently, sulfurization of the nanowhiskers result in hollow $WS_2$ nanotubes.

The PLLA/HA/INT films were prepared by the solvent casting method according to the following procedure.

PLLA neat films: 0.75 g of PLLA pellets was dissolved in 20 ml chloroform and mechanically mixed. Subsequently, the solution was poured onto a Teflon plate for drying in the hood with an aluminum foil cover punctuated with 10 holes.

PLLA films with 40 wt % hydroxyapatite: 0.75 g of PLLA pellets was dissolved in 15 ml chloroform; 300 mg of hydroxyapatite nanoparticles were mixed with 5 ml chloroform and 150 µl oleic acid for 30 min. The two solutions were mixed together using a magnetic stirrer for 5 min before pouring onto a Teflon plate and were then dried in the hood using aluminum foil cover punctuated with 10 holes.

PLLA fin with 0.5 wt % INT-$WS_2$: First, 3.8 mg INT-$WS_2$ powder was dispersed in 5 ml ethanol for 3 min and vacuum annealed for 1.5 h at 80° C. Next, 0.75 g of PLLA pellets was dissolved in 15 ml chloroform and mechanically mixed for 5 hours; then the annealed INT-$WS_2$ were dispersed in 5 ml chloroform for 3 min. Finally, the two solutions were mixed together using a magnetic stirrer for 5 min before pouring onto a Teflon plate for drying in the hood with an aluminum foil cover punctuated with 10 holes.

PLLA films with 40 wt % hydroxyapatite and 0.25, 0.5 and 0.75 wt % INT-$WS_2$: First, 1.9, 3.8 or 5.6 mg of INT-$WS_2$ powder were dispersed in 5 ml ethanol for 3 min and vacuum annealed for 1.5 h at 80° C. Next, 0.75 g PLLA pellets was dissolved in 10 ml chloroform, while 300 mg of hydroxyapatite nanoparticles were dispersed in 5 ml chloroform and 150 µl oleic acid for 30 min. Afterwards, the annealed INT-$WS_2$ were dispersed in 5 ml chloroform for 3 min. Finally, the three solutions were mixed together using a magnetic stirrer for 5 min before pouring onto a Teflon plate for drying in the hood with aluminum foil cover punctuated with 10 holes.

The dried samples were vacuum annealed for 5 days at 45° C. The thickness of the films was determined by caliper and was on the average 80 µm for pure PLLA; 113 µm for PLLA+HA; and 93 µm for PLLA+HA+INT. The densification of the films upon the addition of the nanotubes was attributed to alignment of the polymer molecules along the nanotubes surface. The texturing of the polymer molecules was an indirect evidence to the non-specific but nevertheless strong nanotube-polymer interfacial interaction and explained the mechanical reinforcement of the PLLA by the INT.

Example 8

Characterization of Films of this Invention Comprising PLLA, HA and INT-$WS_2$

X-Ray Diffraction

Figure 13:
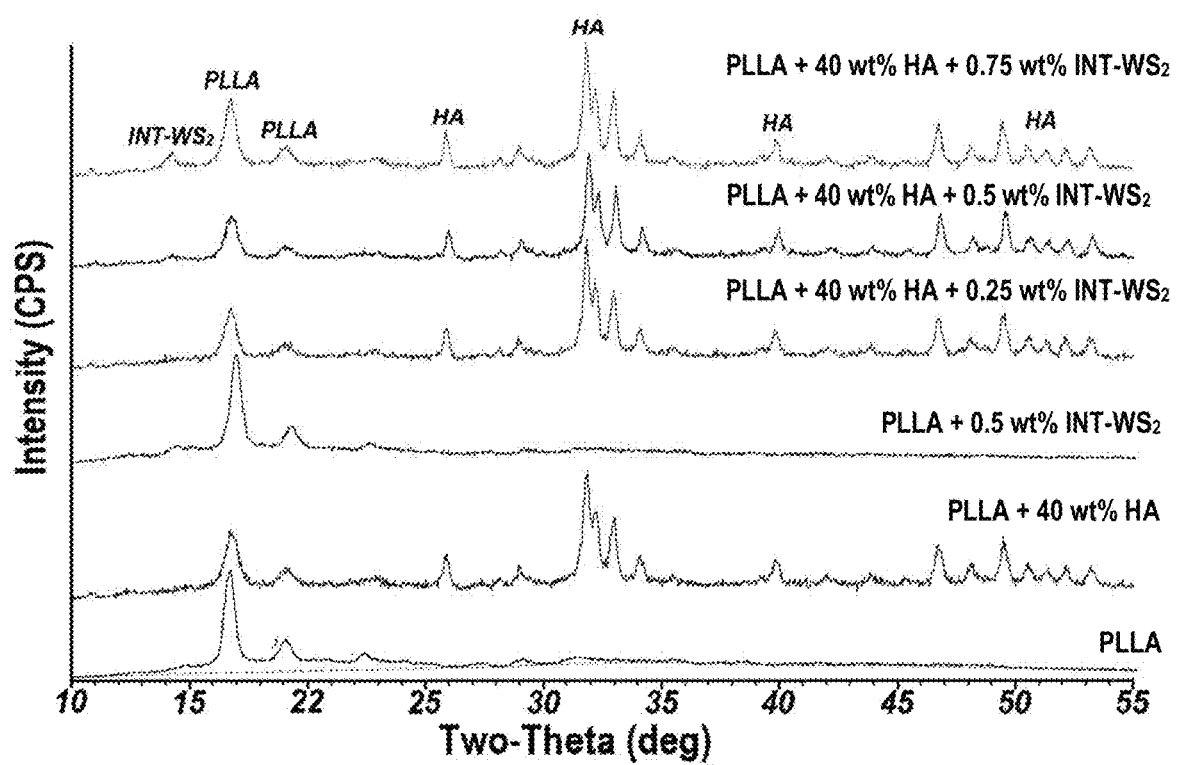
FIG. 13 depicts XRD patterns of PLLA film and HA/INT-WS$_2$/PLLA nanocomposites

Comparison between the XRD patterns of the nano composite films and HA (hydroxyapatite) powder is shown in FIG. 13. The XRD pattern of the composite PLLA and HA and INT-$WS_2$ film contains peaks of the different components, which indicates that the composition and structure of PLLA and HA and nanotubes were not affected by the fabrication process of the film.

Using the Pawley-based WPF analysis, the degree of crystallinity of the samples was calculated by comparing the total area under all the crystal peaks and the area under the amorphous halo. The results are presented in Table 1. The degree of crystallinity of the PLLA film was calculated to be 32.8%. After adding 0.5 wt % of INT-$WS_2$ the degree of crystallinity is slightly increased to 33.2%. However, after adding HA nanoparticles to the PLLA film, the degree of crystallinity increased significantly to 37.1% and remained essentially the same even after adding 0.25-0.75 wt % of INT-$WS_2$. The average crystallite size of the different compositions was estimated using the Williamson-Hall approach from the XRD peak widths fitted in the Pawley-based WPF analysis and the Scherrer equation using the main peak of the PLLA at 16.5° and is reported also in Table 5. The largest crystallite size (171 Å) occurred for the neat PLLA film. As expected, the foreign ingredients (HA and INT) served as crystallization nuclei for the PLLA and reduce its average crystallite size.

TABLE 5

The degree of crystallinity of PLLA film and HA/INT-WS$_2$/PLLA nanocomposites.

| Sample type | Degree of crystallinity [%] WPF | Scherrer | Average crystallite size [Å] WPF PLLA | HA |
|---|---|---|---|---|
| PLLA film | 32.8 ± 0.9 | 170 | 171 ± 2 | — |
| PLLA film with 40 wt % HA | 37.1 ± 3.0 | 130 | 128 ± 5 | 291 ± 18 |
| PLLA film with 0.5 wt % INT-WS$_2$ | 33.2 ± 1.6 | 165 | 162 ± 2 | — |
| PLLA film with 40 wt % HA and 0.25 wt % INT-WS$_2$ | 38.2 ± 2.5 | 145 | 145 ± 5 | 331 ± 20 |
| PLLA film with 40 wt % HA and 0.5 wt % INT-WS$_2$ | 42.7 ± 2.7 | 140 | 144 ± 4 | 353 ± 19 |
| PLLA film with 40 wt % HA and 0.75 wt % INT-WS$_2$ | 42.1 ± 2 s · 2 | 150 | 145 ± 4 | 342 ± 16 |

High-Resolution Scanning Electron Microscopy (HR-SEM)

Figure 14A:
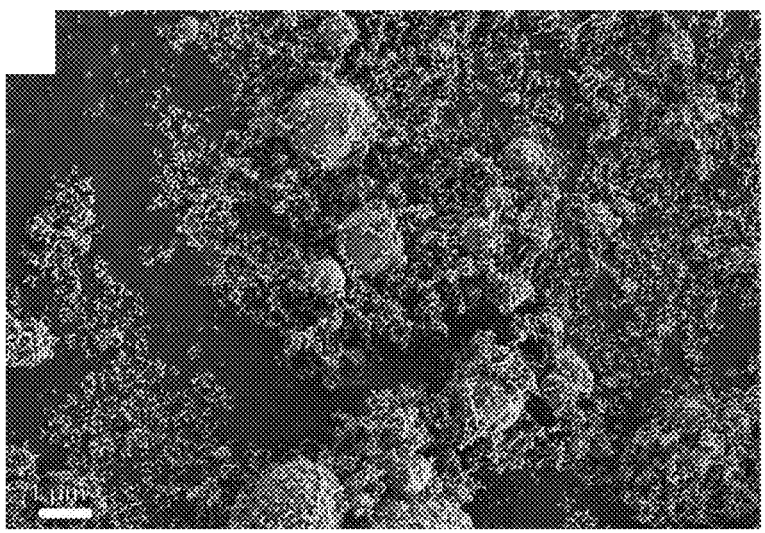
FIGS. 14A-14C depict HR-SEM images (secondary electrons—SE mode) of pure HA powder (FIG. 14A) and PLLA film reinforced with 40 wt % HA observed in the SE mode in two magnifications (scale bars) 2 µm, the arrows point to the spherical agglomerates of HA nanoparticles.
Figure 14B:
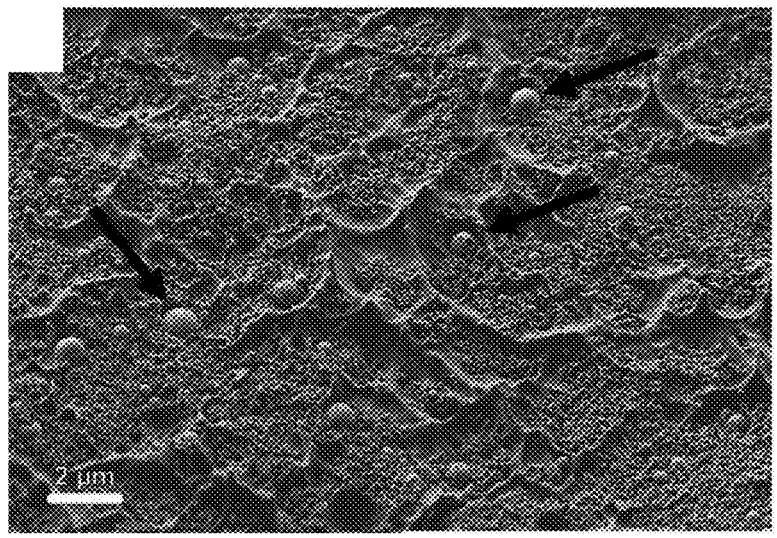
Figure 14C:
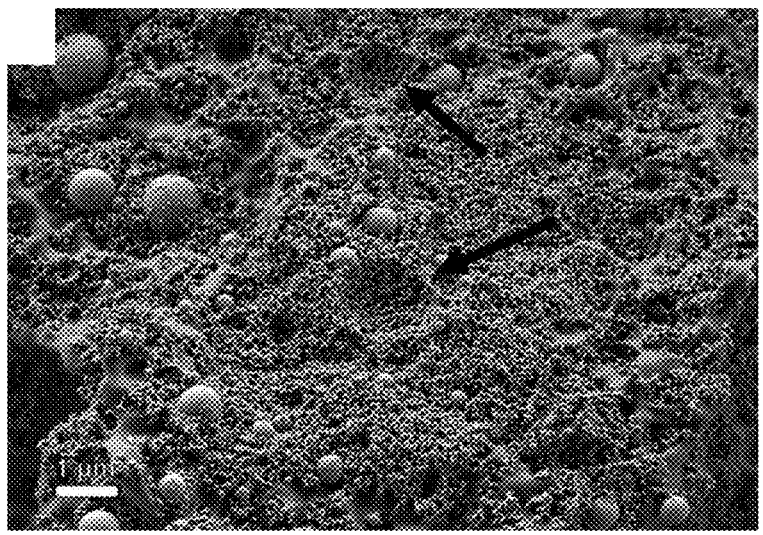

FIGS. 14A-14C show the SEM images of HA powder (FIG. 14A), and a cross-section of PLLA with 40 wt % HA film in secondary electrons (SE) mode (FIGS. 14B and 14C). Visibly (FIG. 14A), the HA particles constitute a bimodal size-distribution made of micron-size agglomerates and a majority phase of a well-dispersed HA nanoparticles (<50 nm). The surface of the large agglomerates is decorated with the small HA NPs. However, the same agglomerates appeared to have a smooth and uniform surface, i.e. free of the decorating HA NPs after being incorporated into the polymer (FIGS. 14B and 14C—marked with green arrows). To further understand this effect, the HA phase was washed in ultrasonic bath with the polymer-free solvent (chloroform) containing the oleic acid. It was found that the surface of the large spherical HA agglomerates became smooth and free of the HA NPs decoration after this washing procedure. Therefore, the solvent treatment seem to be responsible for the "cleaning" of the HA spherical agglomerates. These smooth spherical agglomerates of HA, are likely to impair the mechanical properties of the film.

FIGS. 14B, 14C show that the HA nanoparticles (NPs) were well dispersed in the polymer matrix, i.e. no phase separation or excessive additional agglomeration was observed, which was not the case in the absence of oleic acid. Furthermore, FIG. 14C shows that the HA agglomerates (>0.5 μm) were not damaged during the film breaking process, but were uprooted as a whole from the polymer matrix surface. Furthermore, the hemispherical depressions in FIG. 14C (red arrows) are indicative of entire HA agglomerates, which were uprooted from the polymer matrix during fracture, possibly being stuck to the other surface of the broken contact. Consequently, one can conclude that the strain was not well transferred to these agglomerates during fracture and hence they adversely affected the mechanical strength of the film.

Figure 15A:
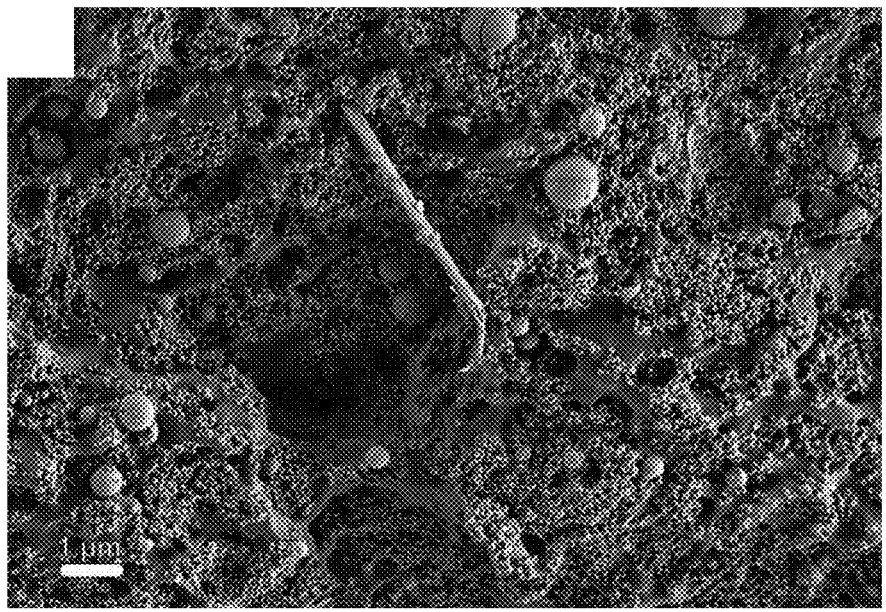
FIGS. 15A-15B depict HR-SEM images of PLLA film reinforced with 40 wt % HA and 0.75 wt % INT-WS$_2$ film in SE mode under 1 µm magnifications (scale bar) (FIG. 15A) and BSE mode in 500 nm (FIG. 15B).
Figure 15B:
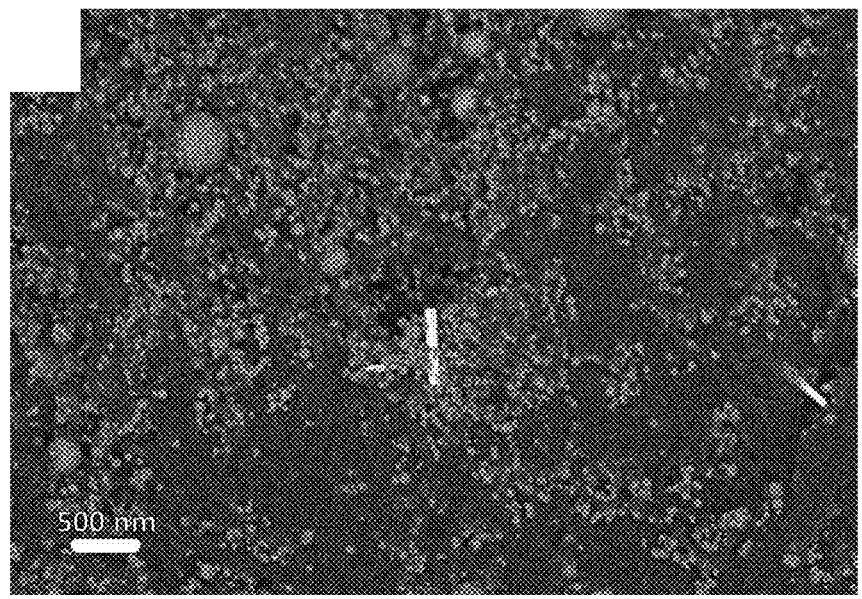

HR-SEM images of the cross section of PLLA reinforced with 40 wt % HA and 0.75 wt % INT-WS$_2$ are presented in FIGS. 15A-15B. It can be seen in FIG. 15A that there was no phase separation and consequently a very good compatibility between the nanotubes and the PLLA matrix and between the HA NPs and nanotubes. The nanotubes protrude from the broken surface, which indicates that they carry some of the applied stress transferred to them from the matrix. In addition, other similar scans show that the INT-WS$_2$, are fully dispersed in the PLLA matrix.

Visibly, the nanotubes protrude from the PLLA matrix, suggesting that they reinforce the polymer via a bridging and pullout mechanisms.

Figures 16A, 16B:
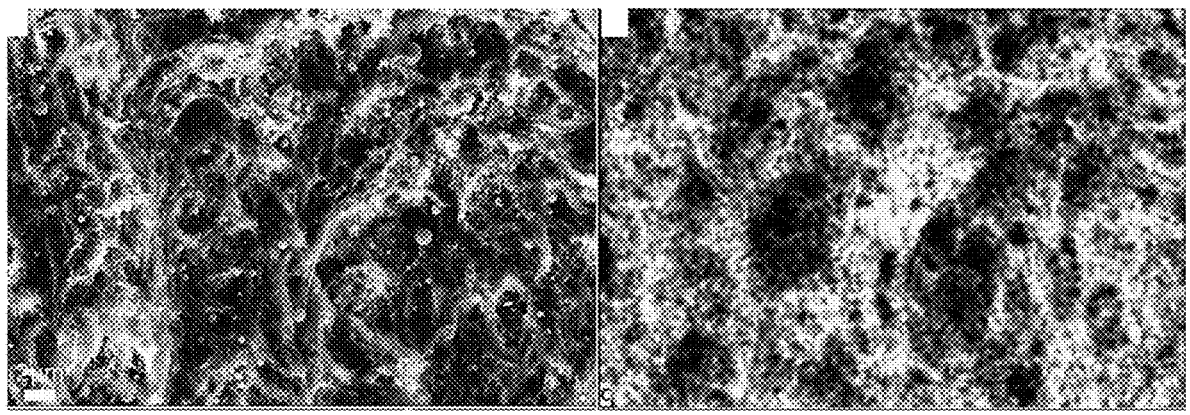
FIGS. 16A-16D depict HR-SEM image of PLLA film reinforced with 40 wt % HA and 0.75 wt % INT-WS$_2$ in SE mode (FIG. 16A) and EDS elemental mapping of the same area: carbon (FIG. 16B), phosphorus (FIG. 16C) and tungsten (FIG. 16D).
Figures 16C, 16D:
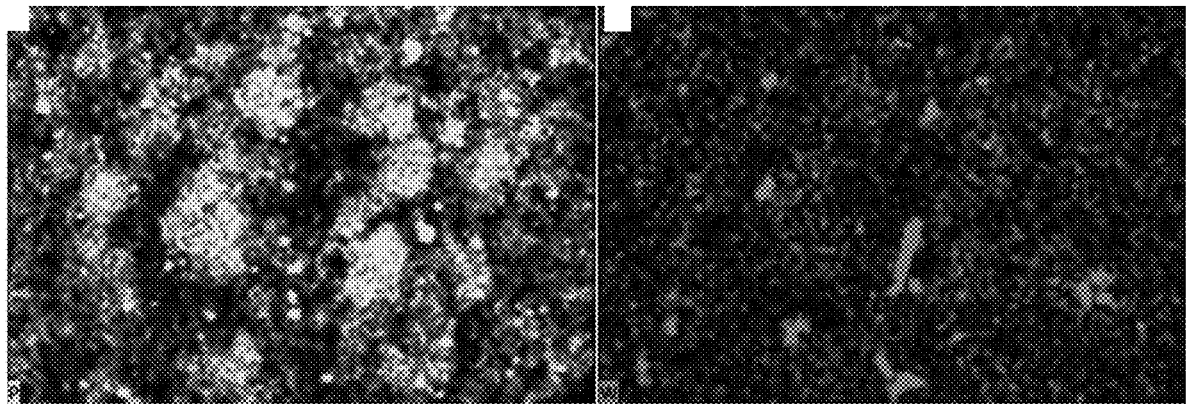

EDS elemental mappings of the PLLA film with 40 wt % HA and 0.75 wt % INT-WS$_2$ are presented in FIGS. 16A-16D. The carbon mapping, displayed in FIG. 16B, shows that the strong carbon signal was evenly distributed throughout the film. This observation reflects the fact that the matrix of the material was PLLA whose chemical composition was mostly carbon. FIG. 16C presents the phosphorus mapping, which was a major component of HA. It can be seen that the HA NPs were well dispersed throughout the film. However, the bimodal distribution with distinct micron and submicron-sized spherical agglomerated and evenly distributed HA nanoparticles was clearly discernable. The INT-WS$_2$ distribution are represented by the tungsten mapping in FIG. 16D, which showed that the nanotubes were well dispersed in the PLLA matrix.

Tensile Test

Figure 17:
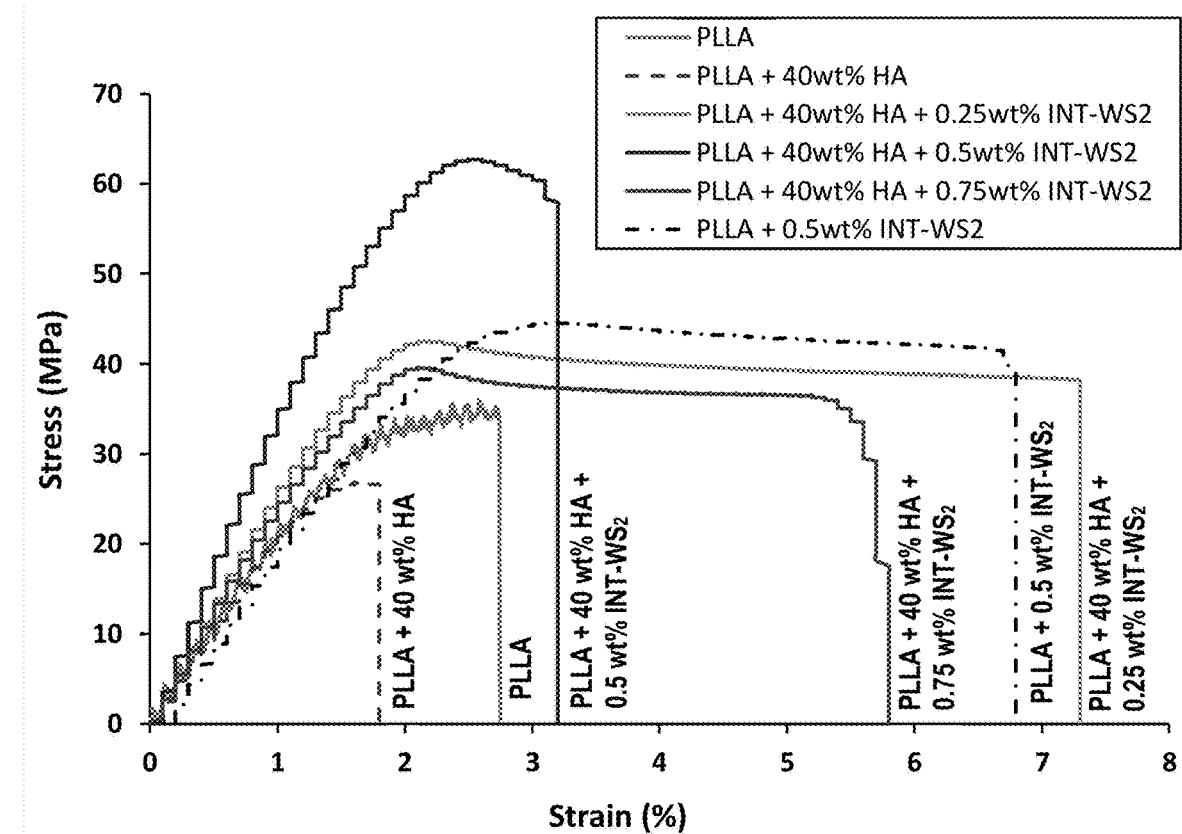
FIG. 17 depicts stress-strain curves of PLLA film and its HA/INT-WS$_2$/PLLA nanocomposites.

The mechanical properties derived from the stress-strain curves of the films are displayed in FIG. 17 and presented in Table 6.

The Young's modulus of PLLA film with 40 wt % HA (2.4 GPa) increased 1.5 times compared to the neat PLLA film (1.55 GPa), while the yield strength (26.7 MPa) and strain at failure (2.1%) of PLLA film with 40 wt % HA decreased to 0.85 and 0.75 of their values, respectively. Therefore, the toughness of PLLA film with 40 wt % HA (0.3 MPa) was reduced by half compared to that of neat PLLA film (0.6 MPa). This is not surprising, since the HA is an oxide with a small strain to failure. Also, the binding of the HA to the PLLA is not chemical in nature and is rather weak (mostly van der Waals and polar interactions). These two factors adversely affected the fracture toughness of the composite. However, the indentation hardness and modulus of the PLLA+HA composite was appreciably higher than that of pure PLLA (see below). Obviously, the most rational way to mediate between the HA and the PLLA phases and increase the mechanical properties of the nanocomposite would be through surface functionalization. The surface functionalization showed chemically versatility and biocompatibility in order to permit the three constituents (PLLA, HA and INT-WS$_2$) to optimally interact with each other and exhibit no biotoxicity effects.

The Young's modulus and yield strength of PLLA film with 0.5 wt %/o INT-WS$_2$ (2.25 GPa and 44.6 MPa, respectively) increased 1.45 times compared to the neat PLLA film, while the strain at failure of the film with 0.5 wt % INT-WS$_2$ (6.8%) increased 2.5 times. Therefore, the toughness of the PLLA film with 0.5 wt % INT-WS$_2$ (2.4 MPa) increased significantly by 4 times compared to the toughness of the neat PLLA film.

The Young's modulus of the PLLA film with 40 wt % HA and 0.5 wt % of INT-WS$_2$ (3.8 GPa) increased up to 1.7 times compared to the PLLA film with 40 wt % HA and to the PLLA film with 0.5 wt % INT-WS$_2$. The yield strength of the PLLA film with 40 wt % HA and 0.5 wt % of INT-WS$_2$ (62.7 MPa) increased by 2.35 and 1.4 times compared to the PLLA film with 40 wt % HA and to the PLLA film with 0.5 wt % INT-WS$_2$. The strain at failure of the PLLA film with 40 wt % HA and 0.5 wt % of INT-WS$_2$ (3.2%) increased 1.5 times compared to the PLLA film with 40 wt % HA. However, the PLLA film with 0.5 wt % INT-WS$_2$, had strain at failure only half the value of the PLLA film with 40 wt % HA and 0.5 wt % of INT-WS$_2$. Therefore, the toughness of the PLLA film with 40 wt % HA and 0.5 wt % INT-WS$_2$ (1.4 MPa) increased significantly by 4.7 times compared to the PLLA film with 40 wt % HA and decreased to 0.6 times the value of the PLLA film with 0.5 wt % INT-WS$_2$.

TABLE 6

The mechanical properties of PLLA film and HA/INT-WS$_2$/PLLA nanocomposites from tensile testing.

| Sample type | Young's Modulus (GPa) | Yield Strength (MPa) | Strain at failure (%) | Toughness (MPa) |
|---|---|---|---|---|
| PLLA film | 1.55 ± 0.15 | 31.0 ± 2.4 | 2.7 ± 1.3 | 0.6 ± 0.2 |
| PLLA film with 40 wt % HA | 2.4 ± 0.1 | 26.7 ± 1.1 | 2.1 ± 0.1 | 0.3 ± 0.1 |
| PLLA film with 0.5 wt % INT-WS$_2$ | 2.25 ± 0.2 | 44.6 ± 4.65 | 6.8 ± 1.0 | 2.4 ± 0.5 |
| PLLA film with 40 wt % HA and 0.25 wt % INT-WS$_2$ | 2.7 ± 0.4 | 42.5 ± 5.8 | 7.3 ± 1.0 | 2.6 ± 0.3 |
| PLLA film with 40 wt % HA and 0.5 wt % INT-WS$_2$ | 3.8 ± 0.5 | 62.7 ± 1.2 | 3.2 ± 1.6 | 1.4 ± 0.7 |
| PLLA film with 40 wt % HA and 0.75 wt % INT-WS$_2$ | 2.7 ± 0.35 | 39.6 ± 4.9 | 5.8 ± 0.7 | 1.8 ± 0.25 |

Micro Hardness Test

Figure 18:
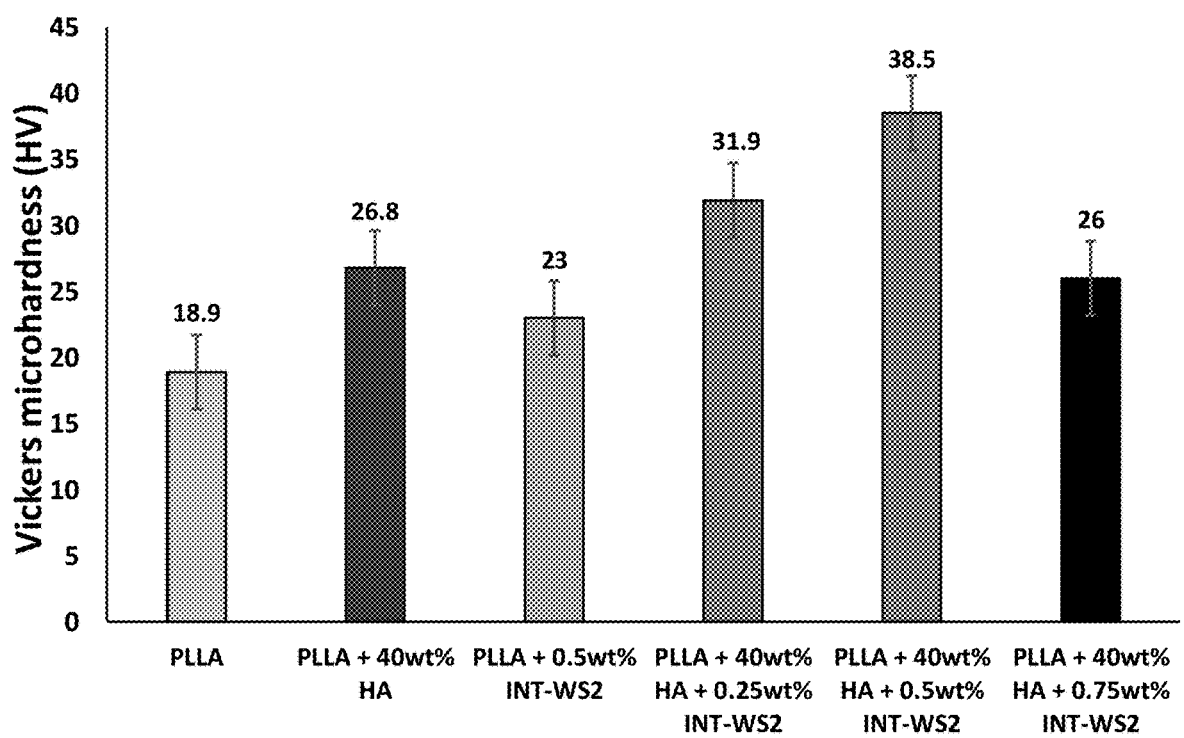
FIG. 18 depicts Micro Vickers hardness test of PLLA film and HA/INT-WS$_2$/PLLA nanocomposites.

FIG. 18 shows the results of the micro-hardness test of PLLA film and the PLLA/HA/INT-WS$_2$ nanocomposites.

The addition of HA nanoparticles to the PLLA film increased the hardness value (26.8 HV) by 1.4 times compared to the hardness value of the neat PLLA film (18.9 HV). In addition, the hardness of the PLLA film with 0.5 wt % INT-WS$_2$ (23 HV) increased 1.2 times compared to the hardness of the neat PLLA film.

Amore significant increase in the hardness was achieved with the combination of HA and INT-WS$_2$ in PLLA. The optimum hardness value was obtained for the films containing PLLA with 40 wt % HA NPs and 0.5 wt % INT-WS$_2$ with 38.5 HV, a value that is two-times higher than the hardness of the pure PLLA film. It can be deduced that a small amount of nanotubes added to the matrix bridges the gap between the HA nanoparticles creating a uniform network of hardening material. Beyond the optimal concentration of 0.5 wt %, the nanotubes have a deleterious effect on the hardness of the nanocomposite, likely due to agglomeration.

Nanomechanical Testing (Nanoindentation Tests)

While microhardness measurements provided an average hardness value, the domain size in the present nanocomposite call for a more local measurements, which will report on possible inhomogeneities in the film. The results from the nanoindentation analysis are presented in Table 7. The results of the nanoindentation experiments are consistent with the Vickers micro-hardness tests discussed above.

The addition of 0.5 wt % INT-WS$_2$ to the PLLA film caused almost no change in the Young's modulus (3.4 GPa) and hardness (0.18 GPa) values compared to the parameters of the neat PLLA film with Young's modulus of 3.3 GPa and harness of 0.16 GPa. However, the Young's modulus and hardness of the PLLA film with 40 wt % HA (4.9 GPa, 0.24 GPa) increased by 1.5 times each compared to the Young's modulus and hardness of the neat PLLA film. The addition of a small amount of nanotubes to the PLLA film with HA increased the Young's modulus and hardness significantly with the optimum being the addition of 0.25 wt % INT-WS$_2$. The Young's modulus and hardness of the PLLA film with 40 wt % HA and 0.25 wt % INT-WS$_2$ (5.6 GPa, 0.36 GPa) increased significantly by 1.7 and 2.25 times, respectively, compared with the values of the neat PLLA film and even the PLLA+HA. Notwithstanding the large fraction of the HA in the film (40 wt %), the hardness values measured here are more than an order of magnitude lower than those reported for a pure HA single crystal. It can be assumed that the difference between the value of hardness measured here and the value observed in the literature, originates from the presence of HA NP agglomerates, which degrade the mechanical properties of the material. Obviously also, the mechanical properties of the nanocomposite are compromised due to the weak links between the HA and the PLLA.

Larger statistical variations for some of the composite samples were consistent with local inhomogeneities in the nanoparticle distribution, as is supported by the EDS measurements and mapping, and the Raman studies (below). Nanoindentation results show relative uncertainties an order of magnitude higher in comparison with the microhardness data. This can be attributed to the scale of the inhomogeneities within the sample: EDS mappings in FIG. 16 show HA "pockets" of several μm extent, and WS$_2$ inhomogeneities on a smaller scale. The area of the microindentation imprint varies between 1000-2500 μm$^2$ (axial length of 30-50 μm) whereas for the nanoindentations the relevant indentation size is on the scale of the HA pockets, and INT length, 4-5 μm.

TABLE 7

Parameters determined from the nanoindentation of PLLA film and HA/INT-WS$_2$/PLLA nanocomposites.

| Sample type | Young's Modulus (GPa) | Hardness (GPa) |
|---|---|---|
| PLLA film | 3.3 ± 0.4 | 0.16 ± 0.05 |
| PLLA film with 40 wt % HA | 4.9 ± 0.7 | 0.24 ± 0.06 |
| PLLA film with 0.5 wt % INT-WS$_2$ | 3.4 ± 0.7 | 0.18 ± 0.08 |
| PLLA film with 40 wt % HA and 0.25 wt % INT-WS$_2$ | 5.6 ± 1.2 | 0.36 ± 0.15 |
| PLLA film with 40 wt % HA and 0.5 wt % INT-WS$_2$ | 4.6 ± 0.8 | 0.25 ± 0.08 |
| PLLA film with 40 wt % HA and 0.75 wt % INT-WS$_2$ | 4.3 ± 0.6 | 0.22 ± 0.07 |

Thermal Properties of PLLA Film and HA/NT-WS$_2$/PLLA nanocomposites by DSC

Figure 19A:
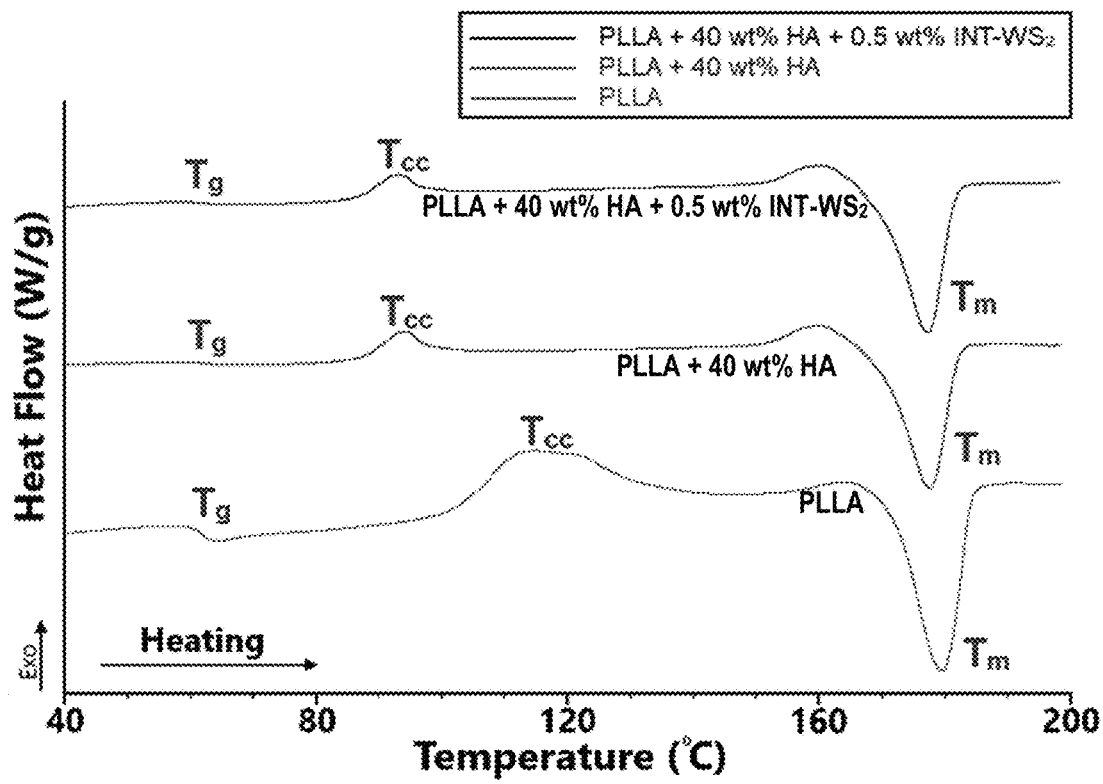
FIGS. 19A-19B depict DSC thermograms of heating (FIG. 19A) and cooling (FIG. 19B) of PLLA film and HA/INT-WS$_2$/PLLA nanocomposites.
Figure 19B:
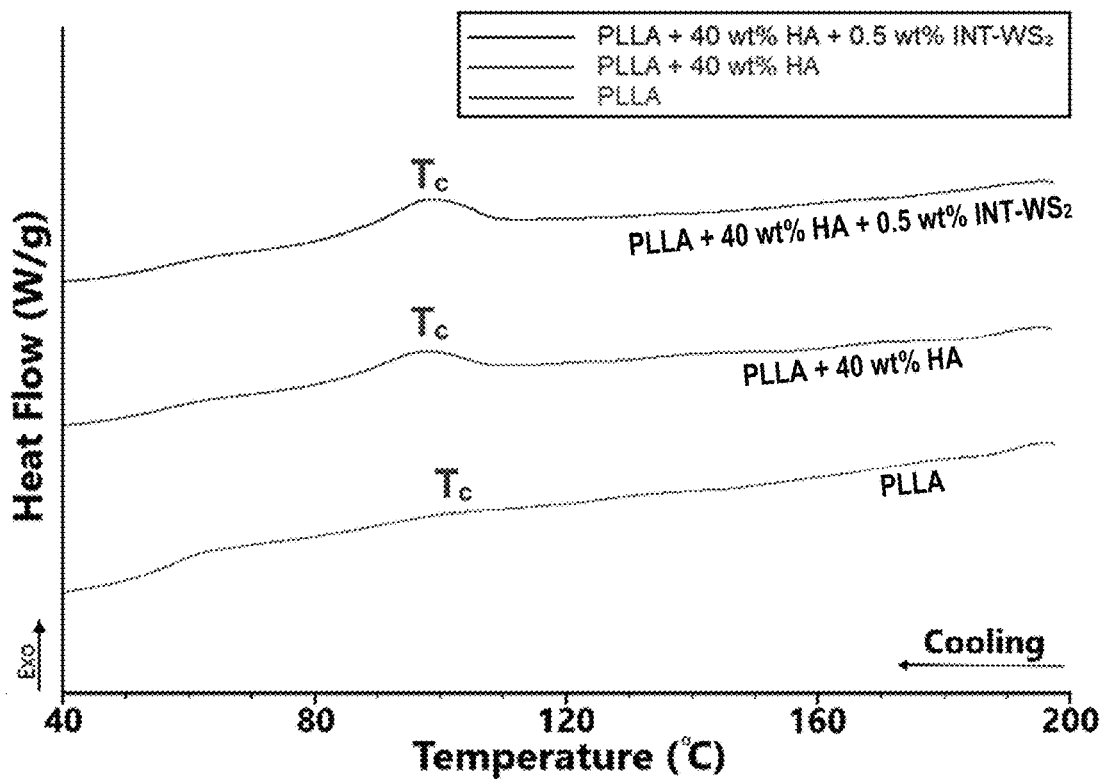

The thermal behavior of the different PLLA films and PLLA/HA/INT-WS$_2$ nanocomposites films were measured using DSC. The results are summarized in Table 8, and the heating and cooling curves are presented in FIG. 19.

The addition of 40 wt % HA nanoparticles to the PLLA film increased the glass transition temperature-T$_g$ (62.7° C.) by merely 1.9% compared to the neat PLLA film (61.5° C.). The addition of 0.5 wt % INT-WS$_2$ to the PLLA film increased T$_g$ (66.7° C.) significantly by 8.5% compared to the T$_g$ of the neat PLLA film. Therefore, the PLLA film with 0.5 wt % INT-WS$_2$ has the highest thermal deformation resistance of the films tested.

The cold crystallization temperature—$T_{cc}$ of the PLLA film with 0.5 wt % INT-WS$_2$ (107.9° C.) is lower than the $T_{cc}$ of the neat PLLA film (114.1° C.). In addition, the PLLA film with 40 wt % HA has lower $T_{cc}$ (93.6° C.) than both the neat PLLA film and the PLLA film with 0.5 wt % INT-WS$_2$, which indicates that the PLLA with 40 wt % HA NPs film consists of smaller crystallites, compared to the neat PLLA film. The lower $\Delta H_{cc}$ of PLLA film with 40 wt % HA and PLLA film with 0.5 wt % INT-WS$_2$ compared to the neat PLLA film also indicates the presence of bigger PLLA crystallites in the neat PLLA film, which is consistent with the findings from XRD (see discussion of Table 5 data, above).

The addition of 40 wt % HA nanoparticles to the PLLA reduced $T_m$ (177.6° C.) compared to the neat PLLA film (179.6° C.), while the addition of 0.5 wt % INT-WS$_2$ resulted in increased $T_m$ (181.7° C.). Therefore, the PLLA film with 0.5 wt % INT-WS$_2$ has the highest thermal stability. The $\Delta H_m$ values of the PLLA films with 40 wt % HA (33.2 J/g) and PLLA film with 0.5 wt % INT-WS$_2$ (34.3 J/g) are lower compared to the PLLA film (39.1 J/g). Therefore, the HA nanoparticles and the INT-WS$_2$ each, independently lower the energy required for breaking the polymer chain-chain interactions. The lower T, and higher $\Delta H_c$ of PLLA film with 40 wt % HA (96.9° C., 5.6 J/g) compared to the PLLA film (101.6° C., 2.0 J/g), shows that the PLLA with 40 wt % HA film has a higher cooling rate and smaller crystal nuclei. The higher T, and higher $\Delta H_c$ of PLLA film with 0.5 wt % INT-WS$_2$ (116.9° C., 34.9 J/g) compared to the PLLA film, indicate that the PLLA film with 0.5 wt % INT-WS$_2$ had lower cooling rate and even smaller crystal nuclei.

The degree of crystallinity—$X_c$ and $(1-\lambda)_c$ of the PLLA film with 40 wt % HA (32.2%, 6.0%) was higher compared to the neat PLLA film (7.5%, 2.2%), which indicated that the PLLA film with 40 wt % HA was harder and denser than the neat PLLA film. However, the $X_c$ and $(1-\lambda)_c$ of PLLA film with 0.5 wt % INT-WS$_2$ (33.5%, 36.7%) was even higher compared to the PLLA film with 40 wt % HA, therefore, the PLLA film with 0.5 wt % INT-WS$_2$ was the hardest and the densest film among the three.

However, the results of micro-hardness test and the nanoindentation tests, show that the hardest film among the three was not the PLLA film with 0.5 wt % INT-WS$_2$, but the PLLA film with 40 wt % HA. The reason for the difference between the estimated hardness trend and the mechanical measurements could possibly be linked to the nuclei size. The crystallites of the PLLA film with 0.5 wt % INT-WS$_2$ were larger than the crystallites of the PLLA film with 40 wt % HA. Although not directly relevant, these results are consistent with the Hall-Petch effect, usually associated with polycrystalline metallic films. According to this law, as the size of the crystallites is reduced, the area of their grain boundaries increase, thereby increasing the hardness of the material.

PLLA films with 40 wt % HA and 0.25-0.75 wt % INT-WS$_2$ have thermal properties ($T_g$, $T_{cc}$, $T_m$ and $T_c$) similar to the PLLA film with 40 wt % HA. Consequently, the PLLA film with 40 wt % HA and 0.25-0.75 wt % INT-WS$_2$ have smaller thermal deformation resistance, crystallite size, thermal stability and lower cooling rate compared with the PLLA film with 0.5 wt % INT-WS$_2$. However, the PLLA film with 40 wt % HA and 0.25-0.75 wt % INT-WS$_2$ had better thermal deformation resistance, smaller crystallites, smaller thermal stability and lower cooling rate compared to the neat PLLA film.

The $\Delta H_{cc}$ of PLLA film with 40 wt % HA and 0.5-0.75 wt % INT-WS$_2$ (2.5-2.4 J/g) was lower compared to the other samples, which was attributed to the smaller crystallites in the nanocomposite films, due to the combined addition of HA nanoparticles and INT-WS$_2$ to the PLLA film. The PLLA film with 40 wt % HA and 0.25 wt % INT-WS$_2$ had lower $\Delta H_{cc}$ (4.8 J/g) compared to the neat PLLA film and higher $\Delta H_{cc}$ compared to the rest of the samples. This data demonstrates that addition of a small amount of INT-WS$_2$ combined with 40 wt % HA produced smaller crystallites compared to the neat PLLA film. The $\Delta H_m$ of the PLLA film with 40 wt % HA and 0.25-0.75 wt % INT-WS$_2$ was lower compared to the other samples, thus the combined addition of HA nanoparticles and INT-WS$_2$ to the PLLA film decreased the flexibility of the polymer chains and the energy required to break the interaction between the polymer chains.

PLLA films with 40 wt % HA and 0.25-0.75 wt % INT-WS$_2$ had similar $X_c$ and $(1-\lambda)_c$ to PLLA film with 40 wt % HA, but lower $X_c$ and $(1-\lambda)_c$ compared to the PLLA film with 0.5 wt % INT-WS$_2$. The $X_c$ and $(1-\lambda)_c$ of PLLA films with 40 wt % HA and 0.5 wt % and 0.75% INT-WS$_2$ were very similar, thus they are equally hard. However, the PLLA film with 40 wt % HA and 0.25 wt % INT-WS$_2$ had lower $X_c$ but higher $(1-\lambda)_c$ compared to the PLLA film with 40 wt % HA and 0.5-0.75 wt % INT-WS$_2$. Therefore, the PLLA film with 40 wt % HA and 0.25 wt % INT-WS$_2$ was more elastic but not as hard as the PLLA films with 40 wt % HA and 0.5-0.75 wt % INT-WS$_2$. This is in agreement with the results of the mechanical properties.

TABLE 8

Thermal properties of PLLA film and HA/INT-WS$_2$/PLLA nanocomposites.

| Sample type | Tg [° C.] | Tcc [° C.] | ΔHcc [J/g] | Tm [° C.] | ΔHm [J/g] | Tc [° C.] | ΔHc [J/g] | Xc [%] | (1-λ)c [%] |
|---|---|---|---|---|---|---|---|---|---|
| PLLA film | 61.5 | 114.1 | 32.1 | 179.6 | 39.1 | 101.6 | 2.0 | 7.5 | 2.2 |
| PLLA film with 40 wt % HA | 62.7 | 93.6 | 3.2 | 177.6 | 33.2 | 96.9 | 5.6 | 32.2 | 6.0 |
| PLLA film with 0.5 wt % INT-WS$_2$ | 66.7 | 107.9 | 3.1 | 181.7 | 34.3 | 116.9 | 34.2 | 33.5 | 36.7 |
| PLLA film with 40 wt % HA and 0.25 wt % INT-WS$_2$ | 62.9 | 93.5 | 4.8 | 177.3 | 31.1 | 97.2 | 8.5 | 28.3 | 9.2 |
| PLLA film with 40 wt % HA and 0.5 wt % INT-WS$_2$ | 62.9 | 92.6 | 2.5 | 177.2 | 32.6 | 98.3 | 5.5 | 32.3 | 5.9 |
| PLLA film with 40 wt % HA and 0.75 wt % INT-WS$_2$ | 62.6 | 95.2 | 2.4 | 177.0 | 32.3 | 99.3 | 5.0 | 32.1 | 5.4 |

Micro-Raman Spectroscopy

Figure 20:
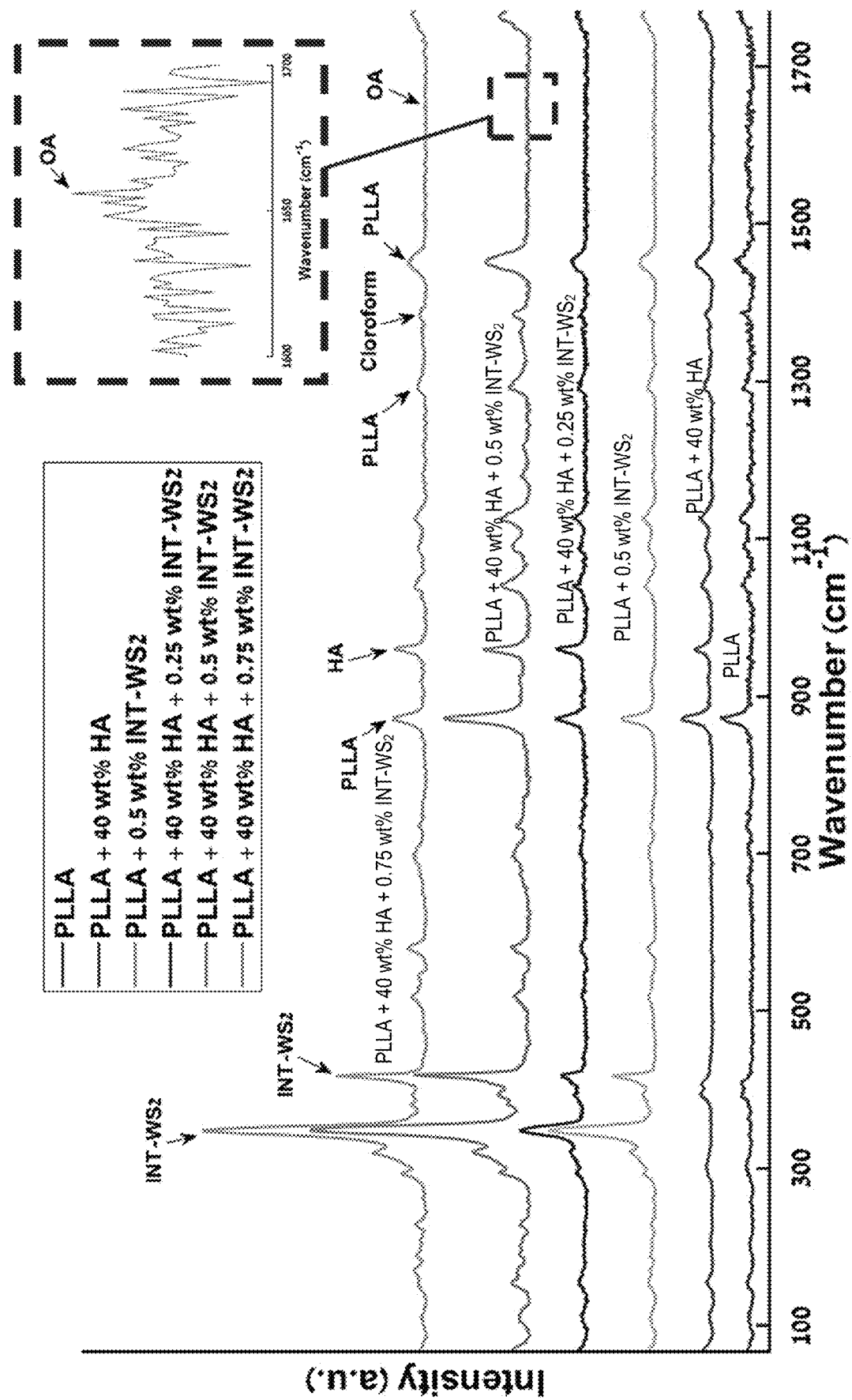
FIG. 20 depicts Raman spectra of the different PLLA films and PLLA/HA/INT-WS$_2$ nanocomposites films. The Raman peak of the oleic acid is shown in the inset.

The Raman spectra of the different PLLA films and PLLA/HA/INT-WS$_2$ nanocomposite films are presented in FIG. 20. The PLLA film with 40 wt % HA and the neat PLLA film had exactly the same pattern of peaks and at the same energy (873 cm$^{-1}$, 1452 cm$^{-1}$), except the peak of the HA at 960 cm$^{-1}$. In addition, comparing the PLLA film with 0.5 wt % INT-WS$_2$ to the neat PLLA film also showed the same pattern of peaks and intensity, except the peaks of the INT-WS$_2$ at 350 cm$^{-1}$ and 418 cm$^{-1}$. The match between the different spectra patterns was excellent, indicating that no chemical reaction took place between the different ingredients of the nanocomposite, as all the identified peaks belong to the pure reagents, with no missing peaks. Hence the chemical composition of the PLLA was not affected by the addition of the HA NPs and INT-WS$_2$, or from the production process of the film as suggested above.

The band of 1379 cm$^{-1}$ was associated with chloroform. That band was seen in the spectra of all the different PLLA films and PLLA/HA/INT-WS$_2$ nanocomposites films. The existence of this peak indicated that residual amounts of the solvent remained in the films.

The film of PLLA with 0.5 wt % INT-WS$_2$ and the films of PLLA with 40 wt % HA and 0.25-0.75 wt % INT-WS$_2$, present peaks at 350 cm$^{-1}$ and 418 cm$^{-1}$, which are associated with the E$_{2g}$ and A$_{1g}$ modes of the INT-WS$_2$.

Oleic acid was a component which was incorporated only into the films of PLLA with 40 wt % HA and 0.25-0.75 wt % INT-WS$_2$. However, the main peak associated with the oleic acid at 1655 cm$^{-1}$ is rather small and can be observed by focusing on the portion of the spectrum near this peak (dashed square) and magnifying the scale. The low intensity of the peak reflects the fact that the oleic acid concentration is very low in the films (150 µl).

Raman intensity mapping of the PLLA with 40 wt % HA and 0.5 wt % INT-WS$_2$ films were carried out (not shown).

Intensity mapping of the PLLA peak at 873 cm$^{-1}$ showed a relatively uniform Raman light scattering intensity on the entire scanned area, with minimum value of 60% with respect to the maximum (normalized) intensity. This indicates, as suggested above, that the PLLA film was uniform and that it was not affected by the addition of the solvent, HA, or and INT-WS$_2$, nor from the fabrication process of the film. The result showed also that no chemical reactions occurred between the four main components during their mixing and processing of the film. Furthermore, the intensity mapping of HA NPs at 960 cm$^{-1}$ showed a good dispersion of the HA nanoparticles in the film, which confirms the observation of a uniform HA distribution obtained via SEM imaging.

Notwithstanding the limited resolution of the technique (>1 µm), the INT-WS$_2$ were clearly seen as elongated shapes throughout the film in the Raman mapping. Obviously, the asymmetric shape of the nanotube does not reflect its genuine shape, since the coarse size of the focused laser beam (1-2 µm) is at least 10-times larger than the tube diameter (~100 nm). Moreover, the nanotubes are fully dispersed in the film. Their long axis seem to be within the film plan and oriented roughly in the x-direction. The preferred directionality of the tubes could be related to the mode of evaporation of the solvent from the casted film.

Raman mapping of oleic acid at 1655 cm$^{-1}$ presents relatively strong and uniform intensity throughout the film area, with minimum value of (normalized) intensity around 40%. Thus, it can be concluded, that the oleic acid was uniformly dispersed throughout the nanocomposite film during its preparation.

FTIR Spectroscopy

Figure 21:
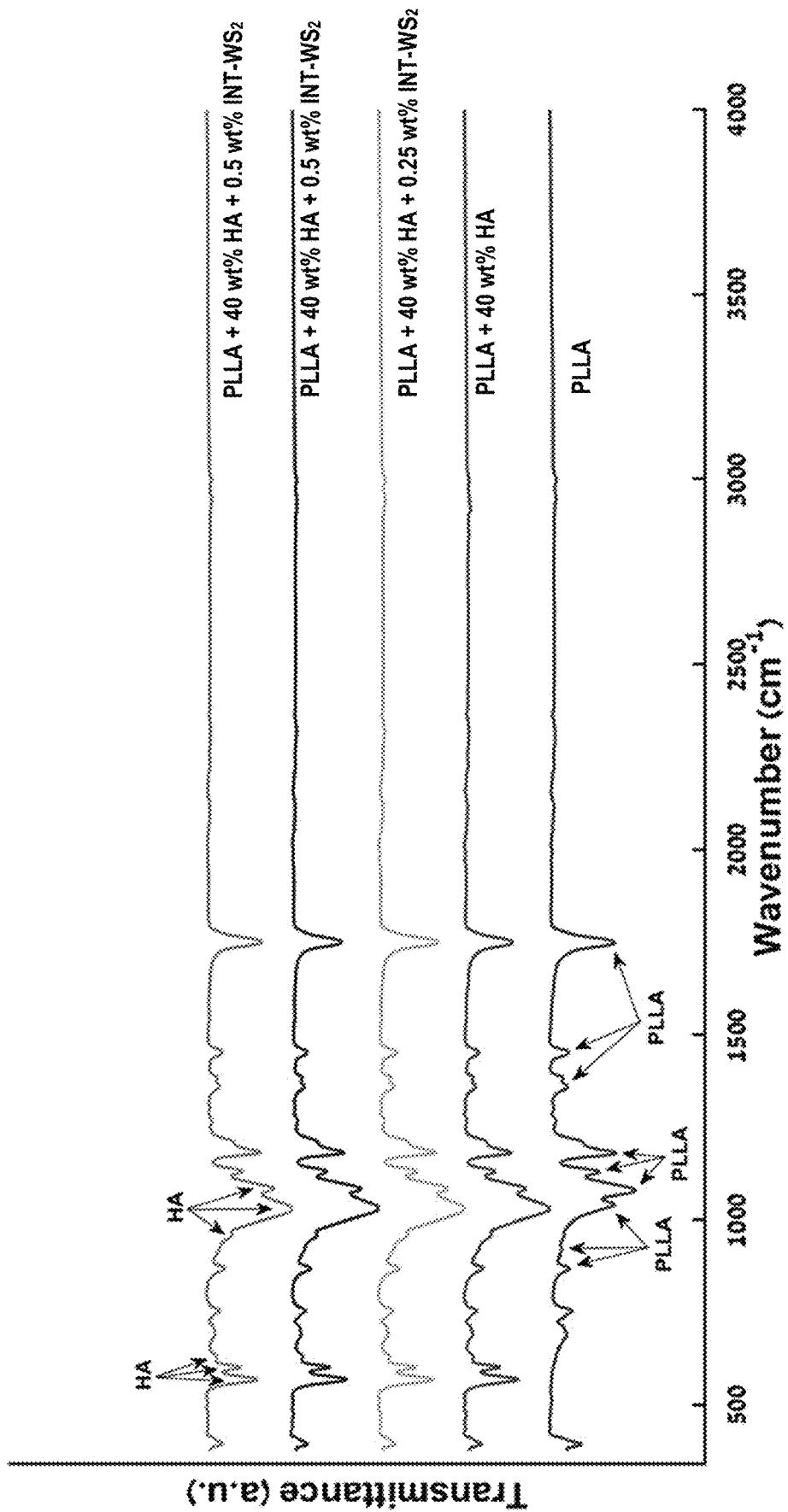
FIG. 21 depicts FTIR spectra of different PLLA/HA/INT-WS$_2$ nanocomposite films.

FTIR of different PLLA/HA/INT-WS$_2$ nanocomposite films was conducted and the results of the spectra are displayed in FIG. 21.

Visibly, PLLA peaks were observed for all different films at the same position, except for the two peaks in 1044 cm$^{-1}$ and 1086 cm$^{-1}$ which overlap with the two IR peaks of HA in 1033 cm$^{-1}$ and 1093 cm$^{-1}$. No extra peaks occur due to the addition of HA and nanotubes to the PLLA.

The nanotubes peaks (<500 cm$^{-1}$) were not observed due to the predominant PLLA peak in this region. Thus, consistently with the previous measurements, the FTIR indicates that the four components (PLLA, HA, OA(=oleic acid) and INT) are mixed together uniformly and they are compatible with each.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A composite comprising a biodegradable polymer, hydroxyapatite [Ca$_{10}$(PO$_4$)$_6$(OH)$_2$)] nanoparticles, a biocompatible surfactant and inorganic fullerene-like nanoparticles or inorganic nanotubes; wherein the inorganic fullerene-like nanoparticles or inorganic nanotubes is A$_{1-x}$B$_x$-chalcogenide where A is a metal or transition metal or an alloy of one metals or transition metals including at least one of the following: Mo, W, Re, Ti, Zr, Hf, Nb, Ta, Pt, Ru, Rh, In, Ga, InS, InSe, GaS, GaSe, WMo, TiW; and B (dopant) is a metal or transition metal selected from the following: Si, Nb, Ta, W, Mo, Sc, Y, La, Hf, Ir, Mn, Ru, Re, Os, V, Au, Rh, Pd, Cr, Co, Fe, Ni; x is between 0 to 0.003; and the chalcogenide is selected from the S, Se, Te.

2. The composite of claim 1, wherein the biodegradable polymer is poly(lactic acid) (PLA), poly(L-lactide) (PLLA) or poly-D-lactide (PDLA).

3. The composite according to claim 1, wherein the biocompatible surfactant is a fatty acid having between 12-24 carbons.

4. The composite according to claim 3 wherein the biocompatible surfactant is oleic acid.

5. The composite according to claim 1, wherein the inorganic fullerene-like nanoparticles or inorganic nanotubes are WS$_2$, MoS$_2$ or combination thereof.

6. The composite according to claim 1, wherein composite is deposited on a substrate forming a film.

7. The composite according to claim 6, wherein the substrate is biocompatible.

8. The composite according to claim 1, wherein the concentration of inorganic fullerene-like nanoparticles or inorganic nanotubes is between 0.1 wt % to 5 wt % of the composition.

9. The composite according to claim 1, wherein the concentration of hydroxyapatite nanoparticles is between 20 wt % to 60 wt % of the composite.

10. The composite of claim 9, wherein the hydroxyapatite nanoparticles and the inorganic fullerene-like nanoparticles or inorganic nanotubes within the film are dispersed in poly(L-lactide) (PLLA).

11. The composite of claim 6, wherein the film provides Young's modulus being 1.5 to 3 times higher compared to a film comprising poly(L-lactide) (PLLA) and hydroxyapatite.

12. The composite of claim 6, wherein the film provides a toughness being 2 to 10 times higher compared to a film comprising poly(L-lactide) (PLLA) and hydroxyapatite.

13. The composite of claim 6, wherein the film provides a hardness being 1.5 to 3 times higher compared to poly(L-lactide) (PLLA) film.

14. The composite of claim 6, wherein the film provides an improved hardness by 1.2 to 3, Young Modules by 1.5 to 3, Toughness by 2-5, Yield Strength by 1.2 to 3 and Strain at failure by 1.1 to 3 compared to poly(L-lactide) (PLLA) film.

15. The composite of claim 6, wherein the film provides higher thermal stability compared to a poly(L-lactide) (PLLA) film or a film comprising poly(L-lactide) (PLLA) and hydroxyapatite.

16. The composite of claim 2, wherein there is no chemical bonding between each of the poly(L-lactide) (PLLA), hydroxyapatite and the inorganic fullerene-like nanoparticles or inorganic nanotubes.

17. A method of coating a metal substrate or forming a film using the composite according to claim 1, wherein the method comprises solvent casting.

18. The method of claim 17, wherein the metal substrate is biocompatible.

19. The method of claim 18, wherein the metal substrate is titanium, alloys of titanium, Co—Cr alloys, magnesium, stainless steel, shape memory alloys of nickel-titanium, silver, tantalum, zirconium and novel ceramics or any electrical-conductive substrate.

20. An implant, a bone repair or tissue engineering comprising the use of the composite of claim 1.

* * * * *